US009284366B2

(12) United States Patent
Krainc et al.

(10) Patent No.: US 9,284,366 B2
(45) Date of Patent: Mar. 15, 2016

(54) ANTI-ACETYLATED HUNTINGTIN ANTIBODIES AND USES THEROF

(75) Inventors: Dimitri Krainc, Boston, MA (US); Hyunkyung Jeong, Cambridge, MA (US); Florian Then, Boston, MA (US)

(73) Assignee: The General Hospital Corporation, Boston, MA (US)

(*) Notice: Subject to any disclaimer, the term of this patent is extended or adjusted under 35 U.S.C. 154(b) by 1610 days.

(21) Appl. No.: 11/981,830

(22) Filed: Oct. 31, 2007

(65) Prior Publication Data

US 2009/0098150 A1 Apr. 16, 2009

Related U.S. Application Data

(60) Provisional application No. 60/856,215, filed on Nov. 2, 2006.

(51) Int. Cl.

*C07K 16/18* (2006.01)
*C12N 5/12* (2006.01)
*C07K 14/47* (2006.01)

(52) U.S. Cl.

CPC ................ *C07K 16/18* (2013.01); *C07K 14/47* (2013.01); *C07K 2317/34* (2013.01)

(58) Field of Classification Search

None

See application file for complete search history.

(56) References Cited

U.S. PATENT DOCUMENTS

2004/0142859 A1 7/2004 Steffan et al.
2006/0069157 A1 3/2006 Ferrante

OTHER PUBLICATIONS

Komatsu et al., J. Immunolog. Meth., vol. 272, 2003, pp. 161-175.*
Jeong, H. et al., "Acetylation Targets Mutant Huntingtin to Autophagosomes for Degradation," *Cell* 2009; 137(1):60-72.
Bates, E. A., Victor, M., Jones, A. K., Shi, Y. & Hart, A. C. Differential contributions of Caenorhabditis elegans histone deacetylases to huntingtin polyglutamine toxicity. J Neurosci 26, 2830-8 (2006).
Campbell, R. E. et al. A monomeric red fluorescent protein. Proc Natl Acad Sci USA 99, 7877-82 (2002).
Cong, S. Y. et al. Mutant huntingtin represses CBP, but not p300, by binding and protein degradation. Mol Cell Neurosci 30, 560-71 (2005).
Dunah, A. W. et al. Sp1 and TAFII130 transcriptional activity disrupted in early Huntington's disease. Science 296, 2238-43 (2002).
Ferrante, R. J. et al. Histone deacetylase inhibition by sodium butyrate chemotherapy ameliorates the neurodegenerative phenotype in Huntington's disease mice. J Neurosci 23, 9418-27 (2003).
Gardian, G. et al. Neuroprotective effects of phenylbutyrate in the N171-82Q transgenic mouse model of Huntington's disease. J Biol Chem 280, 556-63 (2005).
Gatchel, J. R. & Zoghbi, H. Y. Diseases of unstable repeat expansion: mechanisms and common principles. Nat Rev Genet 6, 743-55 (2005).
Goodman, R. H. & Smolik, S. CBP/p300 in cell growth, transformation, and development. Genes Dev 14, 1553-77 (2000).
Hara, T. et al. Suppression of basal autophagy in neural cells causes neurodegenerative disease in mice. Nature 441, 885-9 (2006).
Hockly, E. et al. Suberoylanilide hydroxamic acid, a histone deacetylase inhibitor, ameliorates motor deficits in a mouse model of Huntington's disease. Proc Natl Acad Sci USA 100, 2041-6 (2003).
Jiang, H. et al. Depletion of CBP is directly linked with cellular toxicity caused by mutant huntingtin. Neurobiol Dis. 23(3), 543-51 (2006).
Kabeya, Y. et al. LC3, a mammalian homologue of yeast Apg8p, is localized in autophagosome membranes after processing. Embo J 19, 5720-8 (2000).
Kazantsev, A., Preisinger, E., Dranovsky, A., Goldgaber, D. & Housman, D. Insoluble detergent-resistant aggregates form between pathological and nonpathological lengths of polyglutamine in mammalian cells. Proc Natl Acad Sci U S A 96, 11404-9 (1999).
Kegel, K. B. et al. Huntingtin expression stimulates endosomal-lysosomal activity, endosome tubulation, and autophagy. J Neurosci 20, 7268-78 (2000).
Komatsu, M. et al. Loss of autophagy in the central nervous system causes neurodegeneration in mice. Nature 441, 880-4 (2006).
Martin-Aparicio, E. et al. Proteasomal-dependent aggregate reversal and absence of cell death in a conditional mouse model of Huntington's disease. J Neurosci 21, 8772-81 (2001).
Menalled, L. B., Sison, J. D., Dragatsis, I., Zeitlin, S. & Chesselet, M. F. Time course of early motor and neuropathological anomalies in a knock-in mouse model of Huntington's disease with 140 CAG repeats. J Comp Neurol 465, 11-26 (2003).
Mizushima, N. Methods for monitoring autophagy. Int J Biochem Cell Biol 36, 2491-502 (2004).
Nucifora, F. C., Jr. et al. Interference by huntingtin and atrophin-1 with cbp-mediated transcription leading to cellular toxicity. Science 291, 2423-8 (2001).
Ravikumar, B., Duden, R. & Rubinsztein, D. C. Aggregate-prone proteins with polyglutamine and polyalanine expansions are degraded by autophagy. Hum Mol Genet 11, 1107-17 (2002).
Saudou, F., Finkbeiner, S., Devys, D. & Greenberg, M. E. Huntingtin acts in the nucleus to induce apoptosis but death does not correlate with the formation of intranuclear inclusions. Cell 95, 55-66 (1998).
Shibata, M. et al. Regulation of intracellular accumulation of mutant Huntingtin by Beclin 1. J Biol Chem 281, 14474-85 (2006).

(Continued)

*Primary Examiner* — Jeffrey Stucker
*Assistant Examiner* — Stephen Gucker
(74) *Attorney, Agent, or Firm* — Wolf, Greenfield & Sacks, P.C.

(57) ABSTRACT

This invention includes, in part, methods of preparing acetylated Huntingtin (Htt) polypeptides, acetylated Htt polypeptide antigens, and antibodies that specifically recognize acetylated epitopes on Htt polypeptides. The invention also relates, in part, to the preparation and use of antibodies that specifically recognize and bind to acetylated epitopes on acetylated Htt polypeptides when an acetylated residue on the Htt polypeptide is a lysine that corresponds to K444 residue of full-length, wild-type Htt polypeptide. In some aspects, the invention includes hybridoma cell lines that produce antibodies that specifically bind acetylated Htt polypeptide and also includes antibodies and antigen-binding fragments thereof produced using polypeptides of the invention.

7 Claims, 5 Drawing Sheets

(56) References Cited

OTHER PUBLICATIONS

Steffan, J. S. et al. Histone deacetylase inhibitors arrest polyglutamine-dependent neurodegeneration in Drosophila. Nature 413, 739-43 (2001).

Steffan, J. S. et al. The Huntington's disease protein interacts with p53 and CREB-binding protein and represses transcription. Proc Natl Acad Sci U S A 97, 6763-8 (2000).

Taylor, J. P. et al. Aberrant histone acetylation, altered transcription, and retinal degeneration in a Drosophila model of polyglutamine disease are rescued by CREB-binding protein. Genes Dev 17, 1463-8 (2003).

Trettel, F. et al. Dominant phenotypes produced by the HD mutation in STHdh(Q111) striatal cells. Hum Mol Genet 9, 2799-809 (2000).

Trottier, Y. et al. Cellular localization of the Huntington's disease protein and discrimination of the wild-type and mutated form. Nat Genet 10, 104-10 (1995).

Wheeler, V. C. et al. Length-dependent gametic CAG repeat instability in the Huntington's disease knock-in mouse. Hum Mol Genet 8, 115-22 (1999).

Yamamoto, A., Cremona, M. L. & Rothman, J. E. Autophagy-mediated clearance of huntingtin aggregates triggered by the insulin-signaling pathway. J Cell Biol 172, 719-31 (2006).

* cited by examiner peptide: 443 GKAc VLLGEEEALEDDSESR 460
Relative Abundance
100
m/z
400
600
800
1000
1200
1400
1600
1800
2000

TSA / NAM
acetyl-Htt
Htt
Htt590-97Q
Htt590-97Q-KR

TSA / NAM
acetyl-Htt
Htt
Htt480-17Q
Htt480-68Q

Htt
acetyl-Htt
β-tubulin
vector
CBP
CBP ΔQ
p300
PCAF
Tip60
HAT1
HBO1

Htt
acetyl-Htt
HA-CBP-HAT
CBP-HAT
CBP-HAT-DY

Htt
acetyl-Htt
β-tubulin
vector
HDAC1
HDAC2
HDAC3
HDAC4
HDAC5
HDAC6

Cell death (%)
60
40
20
0
p = 0.002
Htt590-97Q
Htt590-97Q-KR
Htt590-97Q + CBP-HAT
Htt590-97Q-KR + CBP-HAT Htt590-25Q
Htt590-97Q
0h 8h 16h 24h
Htt
β-tubulin Htt590-97Q + CBP-HAT
Htt590-97Q + CBP-HAT DY Htt590-97Q-KR Htt590-97Q-KR + CBP-HAT Htt protein amount (%)
100
80
60
40
20
0
8
16
24
time (h)
Htt590-97Q
Htt590-97Q-KR Htt590-97Q
untreated
DMSO
lactacystin
3-MA
Htt
acetyl-Htt
β-tubulin TSA / NAM:
Htt590-97Q
Htt590-97Q-KR
-
+
-
+
15 kDa
LC3-I
LC3-II % puncta-containing cells
100
80
60
40
20
0
p = 0.009
RFP-Htt480-68Q + GFP-LC3
RFP-Htt480-68Q-KR + GFP-LC3

Htt
acetyl-Htt
$Hdh^{Q7/Q7}$
$Hdh^{Q7/Q140}$
$Hdh^{Q140/Q140}$

Htt
acetyl-Htt
$Hdh^{Q7/Q7}$
$Hdh^{Q7/Q111}$

Htt (MAB5490)
β-tubulin
control
TSA/NAM
mt Htt
wt Htt mt Htt / wt Htt
0
0.2
0.4
0.6
0.8
1
p = 0.023
Control
TSA/NAM Fig. 5
| | | |
|---|---|---|
| Human | 433 | CSPVLSRKQKGKVLLGE |
| Mouse | 410 | CSPVLSRKQKGKVLLGE |
| Rat | 401 | CSPVLSRKQKGKVLLGE |
| Zebrafish | 375 | CSPLLLRKQKGKLLSGE |
| Pufferfish | 376 | CSPLLHRKHRGKMLSGE |
Fig. 6
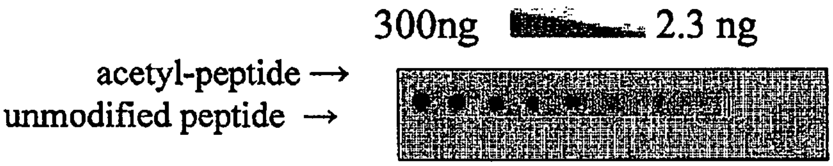
Fig. 7
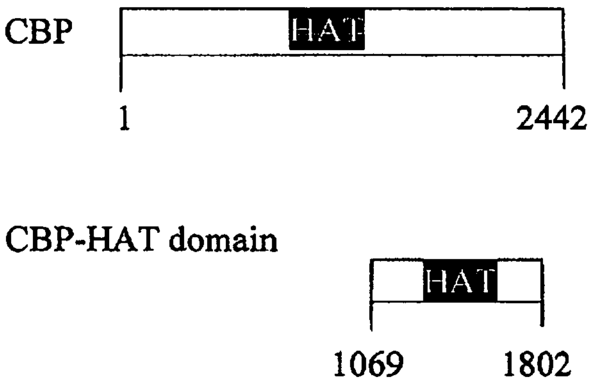
| | | |
|---|---|---|
| CBP Human | 1427 | RRVYISYLDSIHFFRPRC |
| p300 Human | 1391 | RRVYISYLDSVHFFRPKC |

ANTI-ACETYLATED HUNTINGTIN ANTIBODIES AND USES THEROF

RELATED APPLICATIONS

This application is a continuation of U.S. application Ser. No. 12/880,333, filed Sep. 13, 2010, now abandoned, which is a division of U.S. Pat. No. 7,906,120, filed Nov. 21, 2007, which claims priority from Provisional Application 60/860, 256, filed Nov. 21, 2006.

GOVERNMENT SUPPORT

This invention was made with government support under Grant No. R01 NS050352-01 awarded by the National Institutes of Health. The government has certain rights in the invention.

FIELD OF THE INVENTION

This invention relates generally to preparation of acetylated huntingtin (Htt) polypeptide antigens and antibodies that specifically recognize an acetylated epitope on Htt polypeptides. Aspects of the invention also relate, in part, to antibodies or antigen-binding fragments thereof that bind specifically to acetylated Htt polypeptides.

BACKGROUND OF THE INVENTION

Huntington's disease (HD) is one of at least nine autosomal dominant neurodegenerative diseases caused by the expansion of a glutamine repeat in disease proteins. A number of naturally occurring proteins have uninterrupted tracts of glutamine residues encoded by CAG triplet repeats. It now known that the expansion of the length of these uninterrupted tracts or regions of polyglutamine repeats in proteins is associated with specific neurodegenerative diseases. The expansion of polyglutamine tracts in proteins may become pathogenic if the polyglutamine tracts expand beyond a threshold length, which for most of the polyglutamine expansion-associated disorders is a length of approximately 35-40 residues. When the threshold is reached, the presence of the abnormal protein is associated with neurodegenerative diseases such as Huntington's disease (HD).

HD is an autosomal dominant neurodegenerative disorder caused by the expanded CAG tract in the huntingtin gene. HD is characterized clinically by progressive motor impairment, cognitive decline, and various psychiatric symptoms with the typical age of onset in the third to fifth decades. Postmortem changes in HD brains include neuronal loss and gliosis, particularly in the cortex and the striatum. (Vonsattel J P et al. J Neuropathol Exp Neurol. 57: 369-384, 1998.

The onset of Huntington's disease is characterized by choreic movements that result from the selective involvement of medium spiny neurons of the striatum. As HD progresses, more regions of the brain and spinal cord of the patient become involved. The severity of the symptoms and progression of HD varies from patient to patient, in part due to fact that the length of the expanded polyglutamine region correlates with the severity of the symptomatic presentation. The presence of a longer expanded polyglutamine repeat may indicate a more severe type of HD than the presence of a shorter expanded polyglutamine repeat. Thus, patients with longer expanded polyglutamine regions may have more severe clinical effects from the disease and may show an earlier age of onset than would patients with shorter expanded polyglutamine regions.

Previous studies in cell culture and animal models of HD have implicated histone acetyltransferase (HAT) and inhibitors of histone deacetylase (HDAC) as neuroprotective in HD, but the mechanism of protection remains unknown. Inhibitors of histone deacetylation (HDAC inhibitors) have shown promise as potential neuroprotective agents in cell culture and mouse models of HD. In addition, coactivators such as CREB-binding protein (CBP) that contain histone acetyltransferase activity (HAT) have also been shown to protect neurons from huntingtin-mediated toxicity. Mechanism of neuroprotection by compounds involved in acetylation in HD is completely unknown.

Although it is possible to diagnose HD, there are very limited treatment options available for patients diagnosed with HD. Additionally, it is not currently possible to adequately stage HD, to closely follow its onset, progression, or to monitor the effect of candidate therapeutic agents on HD. The lack of effective treatments for HD means that even with a definitive initial diagnosis, the therapeutic options are quite limited.

SUMMARY OF THE INVENTION

The present invention relates, in part, to methods and compositions for making and using antibodies that specifically bind to an acetylated epitope on Huntingtin (Htt) polypeptides. The invention, in some aspects, relates to methods making and using acetylated Htt polypeptides. In some embodiments of the invention, full-length Htt polypeptide (e.g., as set forth in Genbank Accession No. NM 002111 SEQ ID NO:1; with encoding sequence set forth as SEQ ID NO:2) or fragments of Htt polypeptide may be acetylated at one or more lysine residues. In some embodiments, an acetylated lysine residue of a full-length Htt polypeptide or fragment thereof, may be a lysine residue that corresponds to the K444 residue of wild-type, full-length Htt polypeptide.

The invention, in part, includes novel antibodies and antigen-binding fragments thereof that specifically bind acetylated Htt polypeptide. Certain antibodies of the invention specifically bind an Htt polypeptide that is acetylated at an amino acid residue that corresponds to K444 of full-length, wild-type Htt polypeptide. Certain antibodies of the invention specifically bind an acetylated Htt polypeptide that includes one or more acetylated lysines that do not correspond to K444 of full-length, wild-type Htt polypeptide. An acetylated Htt polypeptide may be a lysine-acetylated, wild-type or mutant full-length Htt polypeptide and/or may be a fragment of a full-length wild-type or mutant Htt polypeptide that includes one or more acetylated lysine residues. In some embodiments, an acetylated lysine will correspond to the K444 residue of full-length, wild-type Htt polypeptide. The invention relates in part to the production and use of antibodies that specifically bind to K444-acetylated Htt polypeptides.

The invention also relates, in part, to methods of preparing (e.g., synthesizing) acetylated Htt polypeptides and the use of such synthetic acetylated Htt polypeptides for preparing antibodies that specifically recognize acetylated Htt polypeptide. Isolated acetylated polypeptides of the invention, (e.g., K444-acetylated polypeptides, etc.) may also be used in therapeutic methods and compositions for treatment and/or prevention of Huntington's disease (HD). Such acetylated polypeptides (which may include acetylated full-length wild-type or mutant Htt polypeptides and acetylated fragments thereof), may be used in therapeutics, research, and/or diagnostics relating to HD and/or other polyglutamine expansion-associated diseases.

The invention, in some aspects, includes the use of antibodies and antigen-binding fragments thereof that specifically bind acetylated full-length Htt polypeptides, or fragments thereof, for diagnosis, treatment, and assessment of HD as well as in methods and compositions with which to identify and screen for compounds useful for the treatment or diagnosis of HD and other polyglutamine-expansion diseases.

The invention also includes, in some aspects, compositions for detecting and measuring acetylated Htt polypeptide levels, and methods and compositions for altering acetylated Htt polypeptide levels in a cell, tissue, and/or subject.

The discovery of antibodies that specifically bind to an acetylated Htt polypeptide, that is acetylated at a lysine that corresponds to K444 of full-length Htt polypeptide, facilitates analysis of diseases in which the amount of Htt polypeptide acetylation differs from normal levels. For example, it has been discovered that an increased level of acetylation of Htt polypeptide may lead to an increased clearance of mutant Htt polypeptide and may be neuroprotective in HD. Thus, onset, progression, and/or regression of HD can be monitored by monitoring levels of acetylated Htt polypeptide in a subject and the effects of candidate agents and compounds for the treatment of HD may be assessed by monitoring the level of acetylated Htt polypeptide present in a sample or subject.

According to one aspect of the invention, isolated antibodies or antigen-binding fragments thereof are provided. The antibodies and/or antigen-binding fragments thereof bind specifically to an epitope of acetylated Htt polypeptide, wherein the epitope includes an acetylated lysine. In some embodiments, the acetylated lysine corresponds to K444 of a full-length, wild-type Htt polypeptide. In some embodiments, the acetylated lysine corresponds to K6, K9, K15, K91, K92, K98, K99, K125, K155, K158, K174, K177, K178, K203, K220, K236, K251, K255, K262, K227, K345, K440, K442, K473, K700, K1062, K1186, K1188, K1190, and/or K1300 of a full-length, wild-type Htt polypeptide. In some embodiments, the antibody competitively inhibits binding of an AcK444 antibody to an epitope that includes an acetylated lysine that corresponds to K444 of a full-length, wild-type Htt polypeptide. In some embodiments, the antibody is a monoclonal antibody. In some embodiments, the antibody specifically binds the epitope with a binding affinity of about $1\times10^{-6}$, $1\times10^{-7}$, $1\times10^{-8}$, $1\times10^{-9}$M, $1\times10^{-10}$M, or $1\times10^{-11}$M or less. In some embodiments, the antibody specifically binds the epitope with a binding affinity of about $5\times10^{-10}$M or less. In some embodiments, the antibody is a polyclonal antibody. In some embodiments, the antibody is AcK444. In some embodiments, the antibody is a recombinant antibody. In some embodiments, the antibody is a mouse antibody, a fully human antibody, a chimeric antibody, or a humanized antibody. In some embodiments, the antibody or antigen-binding fragment thereof is attached to a detectable label. In some embodiments, the detectable label is a fluorescent label, an enzyme label, a radioactive label, a nuclear magnetic resonance active label, a luminescent label, or a chromophore label. In some embodiments, the Htt polypeptide is a human Htt polypeptide.

According to another aspect of the invention, a nucleic acid molecule that encodes any of the aforementioned antibodies or antigen-binding fragments thereof of the foregoing aspect of the invention is provided.

According to another aspect of the invention, a hybridoma that includes any of the aforementioned nucleic acid molecules of any of the foregoing aspects of the invention are provided.

According to yet another aspect of the invention, a hybridoma cell line that produces any of the aforementioned antibodies of any of the foregoing aspects of the invention is provided.

According to yet another aspect of the invention, an expression vector that includes an isolated nucleic acid molecule encoding any of the aforementioned antibodies or antigen-binding fragments thereof of any of the foregoing aspects of the invention is provided. According to yet another aspect of the invention, a host cell transfected with any of the aforementioned expression vectors of the foregoing aspects of the invention is provided.

According to yet another aspect of the invention, a plasmid that produces any of the aforementioned antibodies or antigen-binding fragments thereof of any of the foregoing aspects of the invention is provided.

According to yet another aspect of the invention, compositions are provided. The compositions include any of the aforementioned antibodies and/or antigen-binding fragments thereof of any of the foregoing aspects of the invention.

According to yet another aspect of the invention, isolated acetylated Htt polypeptides are provided. The isolated Htt polypeptides include an acetylated lysine residue that corresponds to an acetylated lysine residue of a full-length, wild-type, Htt polypeptide. In some embodiments, the acetylated lysine residue corresponds to the K444 residue of a full-length, wild-type, human Htt polypeptide. In certain embodiments, the acetylated lysine corresponds to K6, K9, K15, K91, K92, K98, K99, K125, K155, K158, K174, K177, K178, K203, K220, K236, K251, K255, K262, K227, K345, K440, K442, K473, K700, K1062, K1186, K1188, K1190, and/or K1300 of a full-length, wild-type Htt polypeptide. In some embodiments, the amino acid sequence of the isolated acetylated Htt polypeptide is set forth as CRKQKGKVLLG (SEQ ID NO:13). In certain embodiments, the polypeptide is immunogenic.

According to yet another aspect of the invention, compositions are provided. The compositions include any of the isolated polypeptides of the aforementioned aspect of the invention.

According to another aspect of the invention, methods of making antibodies that specifically bind to acetylated Htt. The methods include immunizing an animal with any of the abovementioned polypeptides of the foregoing aspects of the invention. In some embodiments, the methods also include removing a lymph node from the immunized animal, harvesting cells from the removed lymph node, fusing the harvested cells with myeloma cells to make hybridomas, expanding the hybridomas, identifying a hybridoma that produces an antibody that specifically binds to the immunogenic polypeptide, and collecting the antibody produced by the hybridoma. In some embodiments, the methods also include harvesting immune cells from the immunized animal, isolating the antibody that specifically binds acetylated Htt polypeptide, sequencing the antibody, preparing a cell that expresses the antibody sequence, and collecting the expressed antibody. In certain embodiments, the animal is a mouse. In some embodiments, the polypeptide has the amino acid sequence set forth as CRKQKGKVLLG (SEQ ID NO:13).

According to yet another aspect of the invention, methods of producing an antibody that specifically binds an acetylated Huntingtin (Htt) polypeptide are provided. The methods include inoculating an animal with any of the aforementioned polypeptides of any of foregoing aspects of the invention, that include an epitope that includes an acetylated lysine that corresponds to an acetylated lysine of full-length, wild-type Htt polypeptide, wherein the polypeptide elicits an immune response in the animal to produce the antibody; and isolating the antibody from the animal; wherein the antibody specifically binds to an acetylated Htt polypeptide. In some embodiments, the animal is a mouse. In some embodiments, the animal is a rabbit. In certain embodiments, the polypeptide has the amino acid sequence set forth as CRKQKGKVLLG (SEQ ID NO:13). In some embodiments, the polypeptide includes a lysine that corresponds to K444 of full-length, wild-type Htt polypeptide.

According to yet another aspect of the invention, methods of determining an amount of acetylated Htt polypeptide in a sample are provided. The methods include contacting a sample with an antibody or antigen-binding fragment thereof that binds specifically to an epitope of acetylated Htt polypeptide, wherein the epitope includes an acetylated lysine, and quantitating the amount of binding of the antibody or antigen-binding fragment to the epitope in the sample as a determination of the amount of acetylated Htt polypeptide in the sample. In certain embodiments, the acetylated lysine corresponds to K444 of a full-length, wild-type Htt polypeptide. In some embodiments, the antibody competitively inhibits binding of an Ack444 antibody to the epitope. In some embodiments, the antibody is a monoclonal antibody. In certain embodiments, antibody specifically binds the epitope with an binding affinity of about $1\times10^{-8}$, $1\times10^{-9}$M, $1\times10^{-10}$M, or $1\times10^{-11}$M or less. In some embodiments, the antibody specifically binds the epitope with a binding affinity of about $5\times10^{-10}$M or less. In some embodiments, the antibody is a polyclonal antibody. In certain embodiments, the antibody is AcK444. In some embodiments, the antibody specifically binds an epitope includes an acetylated lysine that corresponds to K444 of a full-length, wild-type Htt polypeptide with an affinity greater than the affinity of an AcK444 antibody for the epitope. In some embodiments, the antibody is a recombinant antibody. In some embodiments, the antibody or antigen-binding fragment thereof is attached to a detectable label. In certain embodiments, the detectable label is a fluorescent label, an enzyme label, a radioactive label, a nuclear magnetic resonance active label, a luminescent label, or a chromophore label. In some embodiments, the Htt polypeptide is a human Htt polypeptide. In certain embodiments, the sample is a cell sample. In some embodiments, the sample is a tissue sample. In some embodiments, the sample is an in vivo sample. In certain embodiments, the sample is obtained from a subject. In some embodiments, the subject has Huntington's disease.

According to yet another aspect of the invention, methods for evaluating a treatment for regulating Htt polypeptide acetylation levels are provided. The methods include determining a first level of acetylated Htt polypeptide from a first sample obtained from a cell culture or subject undergoing treatment for regulating Htt polypeptide acetylation levels, determining a second level of acetylated Htt polypeptide from a second sample obtained from the cell culture or subject at least one day after obtaining the first level, and comparing the first level to the second level as an evaluation of the treatment, wherein the first and second levels of acetylated Htt polypeptide are determined by any aforementioned methods of any of the foregoing aspects of the invention.

According to yet another aspect of the invention, methods of selecting a treatment for regulating mutant huntingtin polypeptide levels in a subject are provided. The methods include determining a level of acetylated Htt polypeptide from a sample obtained from the subject, and selecting the treatment for regulating mutant huntingtin polypeptide levels in the subject based at least in part on the level determined, wherein the level of acetylated Htt polypeptide is determined by any aforementioned method of any of the foregoing aspects of the invention.

According to yet another aspect of the invention, methods of assessing onset, progression, or regression of Huntington's disease (HD) are provided the methods include determining a level of acetylated Htt polypeptide from a sample obtained from a subject, and comparing the level to a control level as an assessment of onset, progression, or regression of the condition, wherein the level of acetylated Htt polypeptide is determined by any aforementioned method of any of the foregoing aspects of the invention.

According to yet another aspect of the invention, methods for identifying a compound that increases an amount of acetylated Huntingtin (Htt) polypeptide in a cell are provided. The methods include contacting a cell that includes Htt polypeptide with a compound, determining an amount of Htt polypeptide acetylation in the cell, and comparing the amount of Htt polypeptide acetylation detected in the cell to an amount of Htt polypeptide acetylation in a control cell that is not contacted with the compound, wherein an increase in the level of Htt polypeptide acetylation in the cell compared to the level in the control cell identifies the compound as a compound that increases the level of acetylated Htt polypeptide. In some embodiments, the candidate compound is an HDAC inhibitor. In some embodiments, the candidate compound is an HDAC1 inhibitor. In certain embodiments, the cell is a cultured cell. In some embodiments, the cell is an in vivo cell. In some embodiments, the cell is obtained from a subject. In some embodiments, the subject has HD. In certain embodiments, the means for determining the amount of acetylated Htt polypeptide is determined by any aforementioned method of any of the foregoing aspects of the invention.

According to yet another aspect of the invention, methods of administering a treatment for regulating mutant huntingtin polypeptide levels in a subject are provided. The methods include, determining a level of acetylated Htt polypeptide from a sample obtained from the subject, and administering a treatment for regulating mutant huntingtin polypeptide levels in the subject based at least in part on the level of acetylated Htt polypeptide determined, wherein the level of acetylated Htt polypeptide is determined by any aforementioned method of any of the foregoing aspects of the invention. In some embodiments, the treatment includes administering an effective amount of an HDAC inhibitor to the subject. In some embodiments, the HDAC inhibitor is an HDAC1 inhibitor. In certain embodiments, the treatment that includes administering an effective amount of an acetylated Htt polypeptide to the subject.

According to yet another aspect of the invention, kits for detecting the presence of acetylated Htt polypeptide are provided. The kits include a package including a container containing any of the aforementioned isolated antibody or antigen-binding fragment thereof of any of the foregoing aspects of the invention, and instructions for use of the antibody or antigen-binding fragment thereof to detect the presence of acetylated Htt polypeptide. In some embodiments, the kits also include a container containing a second antibody or antigen-binding fragment thereof that specifically binds a non-acetylated Htt polypeptide or non-K444-acetylated Htt polypeptide, and instructions for using the second antibody as a control antibody. In certain embodiments, the kits also include a container containing an antibody that specifically binds non-acetylated Htt polypeptide.

According to yet another aspect of the invention, kits for detecting and/or treating HD are provided. The kits include a package including a container containing any of the aforementioned isolated antibody or antigen-binding fragment thereof of any of the foregoing aspects of the invention, a container containing a therapeutic compound for preventing and/or treating HD, and instructions for use of the antibody or antigen-binding fragment there of to detect the presence of acetylated Htt polypeptide and for use of the therapeutic compound for preventing and/or treating HD. In some embodiments, the kits also include a container containing a second antibody or antigen-binding fragment thereof that specifically binds a non-acetylated Htt polypeptide or non-K444-acetylated Htt polypeptide, and instructions for using the second antibody as a control antibody. In some embodiments, the kits also include a container containing an antibody that specifically binds non-acetylated Htt polypeptide. In some embodiments, the therapeutic compound is an HDAC inhibitor. In certain embodiments, the HDAC inhibitor is an HDAC1 inhibitor. In some embodiments, the therapeutic compound is an acetylated Htt polypeptide.

These and other aspects of the invention will be described in further detail in connection with the detailed description of the invention.

BRIEF DESCRIPTION OF THE DRAWINGS

FIG. 1 shows an HPLC trace and western blots demonstrating human huntingtin polypeptide acetylated at lysine 444 (K444).

FIG. 2 shows graphs and western blots demonstrating that acetylation of mutant Htt polypeptide at K444 leads to increased Htt polypeptide clearance and neuroprotection. FIG. 2B shows that mutant Htt590-97Q has a longer half-life than wild type Htt590-25Q. FIG. 2C shows that co-transfection of CBP-HAT, but not the HAT-deficient mutant CBP-7HAT-DY resulted in decreased levels of mutant Htt polypeptide. FIG. 2D shows that when Htt590-97Q and Htt590-97Q-KR were overexpressed in Neuro2a cells without CBP-HAT, no significant difference in protein turnover was observed. FIG. 2E shows that acetylation-induced decrease of mutant Htt protein depends on K444. Co-expression of CBP-HAT led to markedly increased clearance of Htt590-97Q, whereas mutation of K444 prevented this effect of CBP-HAT.

FIG. 3 provides western blots and a graph demonstrating that acetylation of Htt polypeptide enhances autophagic clearance of the mutant polypeptide.

FIG. 4 shows western blots and a graph demonstrating that Htt polypeptide is acetylated in vivo. Htt polypeptide was immunoprecipitated from brain homogenates of Htt polypeptide knock-in mice and subjected to western blotting.

FIG. 5 shows an alignment of five polypeptide sequences demonstrating that lysine 444 in Htt polypeptide is a conserved residue. Full-length Htt polypeptide sequence alignment reveals conservation of K444 (arrowhead) in human (SEQ ID NO:4), mouse (SEQ ID NO:5), rat (SEQ ID NO:6), zebrafish (SEQ ID NO:7) and pufferfish (SEQ ID NO:8).

FIG. 6 provides a dot-blot assay demonstrating the specificity of rabbit polyclonal antibody against acetyl-K444 Htt polypeptide (AcK444). Nitrocellulose membrane was spotted with different amounts of acetyl-K444 polypeptide or unmodified polypeptide and probed with AcK444 antibody.

FIG. 7 provides a schematic diagram and sequences used for subcloning of CBP-HAT domain and generation of HAT-deficient CBP construct. Truncated CBP encompassing the HAT domain (CBP-HAT, aa1096-1802) was subcloned into mammalian HA-tagged expression vector (pGWI-HA). The corresponding HAT-deficient construct was generated by mutating aspartic acid residue 1435 to tyrosine (Y), analogous to the D1399Y mutation that abolishes HAT activity of p300. The protein alignment depicts the highly conserved region of the CBP and p300 HAT domains with the critical aspartic acid residue marked by an arrowhead. The CBP human sequence RRVYISYLDSIHFFRPRC is SEQ ID NO:9 and the p300 human sequence is RRVYISYLDSVHFFRPKC is SEQ ID NO:10.

DETAILED DESCRIPTION OF THE INVENTION

Figures 1A, 1B, 1C, 1D, 1E, 1F:
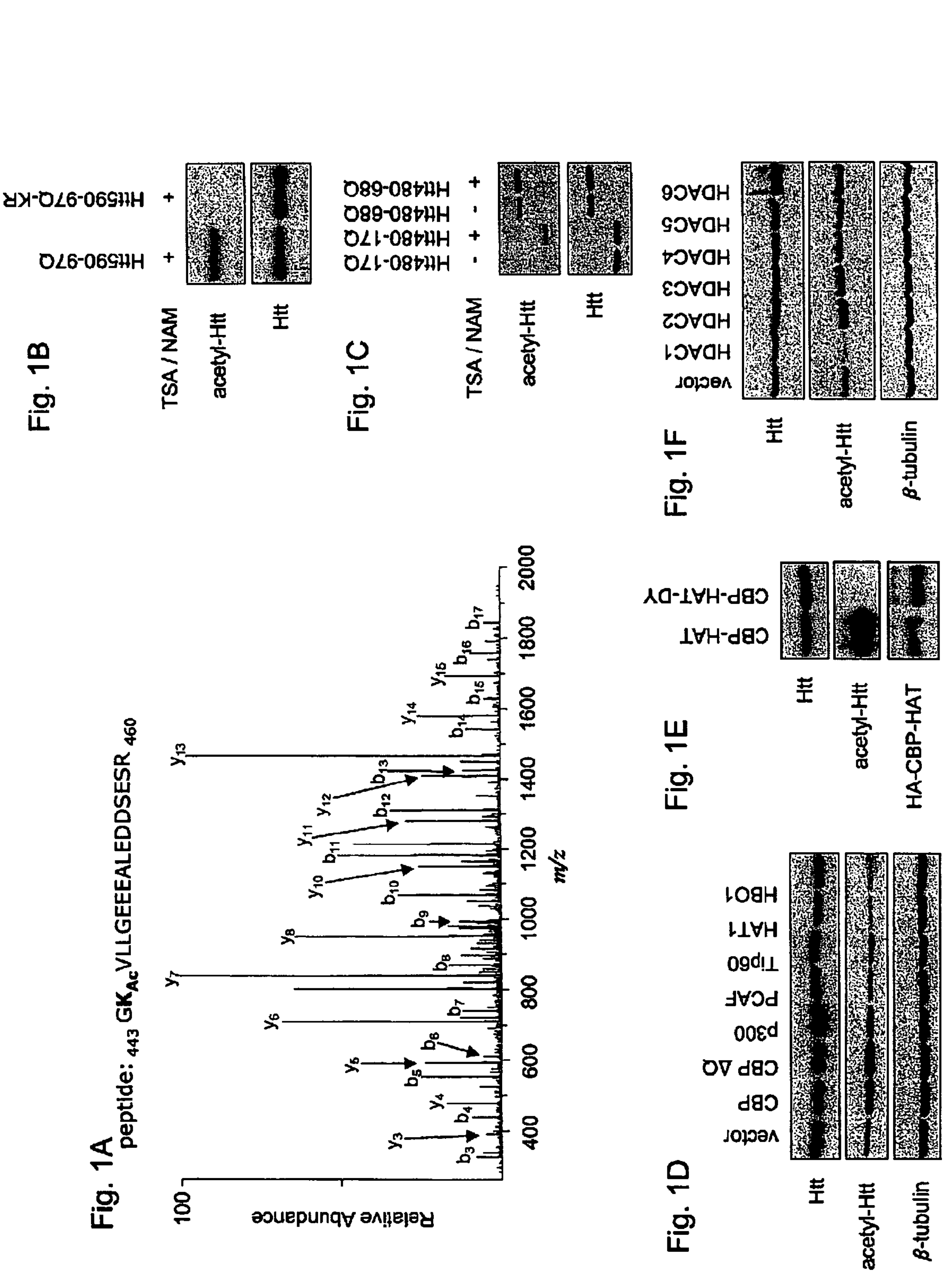
(FIG. 1A) LC-MS/MS spectrum of acetylated polypeptide $GK_{Ac}$VLLGEEEALEDDSESR (SEQ ID NO:3) obtained from Htt480-68Q-Myc. The unfragmented polypeptide as well as a series of b-ions displayed a mass change of +42 Da, indicative of acetylation.
FIG. 1B illustrates the reactivity of antibody raised against acetyl-K444 Htt (Ab AcK444). COS-7 cells were transfected with Htt590-97Q or Htt mutated at lysine 444 to arginine (Htt590-97Q-KR), treated with trichostatin A (TSA) and nicotinamide (NAM), and analyzed by western blotting. Mutation of lysine 444 completely abrogated the reactivity of AcK444 antibody.
FIG. 1C shows that treatment with HDAC inhibitors increases acetylation of Htt at K444. COS-7 cells were transfected with Htt480-17Q or Htt480-68Q and treated with TSA and NAM. Membranes were probed with AcK444, and with MAB5490 for total Htt protein.
FIG. 1D shows results when Htt480-68Q was transfected into COS-7 cells together with histone acetyltransferases (HATs): CBP, CBP lacking glutamine-rich domain (CBPΔQ), p300, P/CAF, Tip60, HAT1, and HBO1. Levels of total and acetylated Htt polypeptide are shown. Beta-tubulin was used as a loading control.
FIG. 1E shows results indicating that CBP-HAT increases acetylation of Htt. COS-7 cells were transfected with Htt480-68Q and CBP HAT-domain (CBP-HAT), or HAT-deficient CBP-HAT-DY construct. Western blot analysis was performed using Htt antibody MAB5490 and AcK444 antibody. Expression levels of CBP-HAT constructs were detected by HA-antibody.
FIG. 1F shows acetyl-Htt is deacetylated by HDAC1. Neuro2a cells were transfected with Htt480-68Q along with CBP-HAT and HDACs 1-6. Western blot shows levels of total Htt polypeptide and acetyl-Htt polypeptide. Beta-tubulin was used as loading control. All data are representative of at least three independent experiments.

The discovery of antibodies that specifically bind to an acetylated Htt polypeptide facilitates analysis of HD disease and treatments. For example, it has been discovered that an increased level of acetylation of Htt polypeptide may lead to an increased clearance of mutant Htt polypeptide and may be neuroprotective in HD. Thus, modifying the amount of acetylation of Htt polypeptide may alter the clearance of the Htt polypeptide from a cell or tissue. An increase in acetylation of Htt polypeptide may result in increased clearance of mutant Htt polypeptide and a corresponding decrease of the clinical aspects and symptoms of the disease. In addition, antibodies may be used to monitor the onset, progression, and/or regression of HD by monitoring levels of acetylated Htt polypeptide in a cell or subject and determining the effect of a candidate therapeutic compound on the level of acetylated Htt polypeptide. Such monitoring may also be used to assess the efficacy of treatments administered to an individual subject by monitoring the level of acetylated Htt polypeptide present in a sample or subject before and after administration of a treatment regimen (e.g., a therapeutic agent).

The present invention provides antibodies or antigen-binding fragments thereof that bind specifically to a K444-acetylated Htt polypeptide (e.g., Htt acetylated at the residue that corresponds to K444 in full-length Htt polypeptide), compositions containing one or a combination of such antibodies or antigen-binding fragments thereof, hybridoma cell lines that produce the antibodies, and methods of making and using acetylated Htt polypeptides and/or anti-acetylated-Htt polypeptide antibodies or antigen-binding fragments thereof for diagnosis and treatment of HD. The invention, in part also includes, acetylated Htt polypeptides, compositions comprising acetylated Htt polypeptides, and acetylated Htt polypeptide antigens (natural and synthetic) that can be used to produce antibodies. In some embodiments, polypeptides of the invention are K444-acetylated polypeptides. As used herein, the terms "protein" and "polypeptide" are used interchangeably and thus the term polypeptide may be used to refer to a full-length polypeptide and may also be used to refer to a fragment of a full-length polypeptide.

It has been determined that natural acetylation of Htt polypeptide, including, but not limited to K444 acetylation of Htt polypeptide, is correlated with the removal of mutant Htt polypeptide from a cell, tissue, and/or subject. A reduction in acetylation (e.g., K444 acetylation) of mutant Htt polypeptide has now been correlated with reduced removal of mutant Htt polypeptide from a cell, tissue, or animal. In addition, acetylation of mutant Htt polypeptide increases its clearance by autophagy. Thus, acetylation of one or more lysine residues (e.g., K444) of mutant Htt polypeptide enhances removal of the mutant Htt polypeptide from a cell.

A wild-type, full-length human Htt polypeptide has the amino acid sequence set forth as Accession No. NP_002102. An acetylated wild-type, full-length human Htt polypeptide also has the amino acid sequence set forth in Genbank Accession No. NP_002102, but is acetylated at one or more of its lysine residues. A lysine at residue K444 of full-length, wild-type Htt polypeptide may be acetylated. A nucleic acid sequence encoding human wild-type, full-length Htt is set forth as Genbank Accession No. NM_002111 (SEQ ID NO:2), the nucleic acid encoding mouse wild-type Htt polypeptide has GenBank Accession No: NM_010414 and is set forth herein as SEQ ID NO:11.

The amino acid sequence of a non-acetylated, full-length, human wild-type Htt polypeptide is set forth as SEQ ID NO:1 and the amino acid sequence of a K444-acetylated full-length, human wild-type Htt polypeptide is provided as SEQ ID NO:12. In the amino acid sequence of the wild-type human full-length Htt polypeptide, a polyglutamine repeat is located at residues 18-40 and is 23 residues in length. Mutant Htt polypeptides may include expanded polyglutamine repeats of various lengths, and fragments of wild-type or mutant Htt polypeptide will also be of shorter length than a full-length wild-type or mutant Htt polypeptide, respectively. Thus, the designation of a specific amino acid residue in a mutant or fragment of Htt polypeptide is based on the corresponding residue identity in a full-length, wild-type Htt polypeptide. Because a mutant Htt polypeptide may include an expanded polyglutamine region, the lysine residue that corresponds to residue K444 in the wild-type, full-length Htt polypeptide, may be a higher residue number in the amino acid sequence of mutant Htt polypeptide than it would be in the wild-type full-length Htt polypeptide. For example, if a polyglutamine tract in a mutant Htt polypeptide has 35 glutamine residues instead of 23 glutamines in a polyglutamine tract of a wild-type Htt polypeptide, the residue number for the lysine that corresponds to K444 of full-length, wild-type Htt polypeptide would be K456 for that mutant Htt polypeptide. To simplify the nomenclature, the K456 residue of the mutant Htt polypeptide may be referred to as the K444 residue because it corresponds to the K444 residue of a full-length, wild-type Htt polypeptide. Thus, in some embodiments, the acetylated lysine residue in a fragment of Htt polypeptide is referred to as an acetylated K444 residue—even though the fragment is not a full-length Htt polypeptide. In certain embodiments of the invention, the acetylated residue of Htt polypeptide or a fragment thereof is or corresponds to a different lysine found in full-length, wild-type Htt polypeptide. Examples of lysines that correspond to lysines in full-length Htt polypeptides that may be acetylated include, but are not limited to, K6, K9, K15, K91, K92, K98, K99, K125, K155, K158, K174, K177, K178, K203, K220, K236, K251, K255, K262, K227, K345, K440, K442, K473, K700, K1062, K1186, K1188, K1190, and K1300. In some embodiments, K9 and/or K227 or others of the aforementioned lysine positions that are acetylated may be used in methods and/or products of the invention. In some embodiments, more than one lysine (K) residue is acetylated. In some embodiments, only one lysine residue is acetylated. In certain embodiments, only a K444 residue is acetylated.

There may be allelic variation in Htt polypeptide sequences of the invention including wild-type Htt polypeptide sequences and/or mutant Htt polypeptide sequences. As used herein, the term “allelic variant” means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides with altered amino acid sequences. An allelic variant of a polypeptide is a polypeptide encoded by an allelic variant of a gene. It will be understood by those of ordinary skill in the art that such allelic variations may occur in full-length wild-type and mutant Htt polypeptides and in fragments of wild-type and mutant polypeptides. Htt polypeptides of the invention may be allelic variants of wild-type Htt or mutant Htt polypeptide sequences. One or ordinary skill in the art will be able to identify how residues of variants of wild-type and mutant Htt polypeptide correspond to residues of wild-type Htt polypeptide using routine methods.

The invention, in some aspects, includes acetylated Htt polypeptides. The term, “acetylated Htt polypeptide” means an Htt polypeptide that has been acetylated at one or more lysine residues. In some embodiments of the invention, an Htt polypeptide may be acetylated only at the residue that corresponds to the K444 residue of wild-type, full-length Htt polypeptide. In some embodiments, an acetylated Htt polypeptide is an Htt polypeptide that has been acetylated at the amino acid residue that corresponds to the amino acid residue number 444 of full-length wild-type Htt polypeptide, which is set forth herein as SEQ ID NO:1. The residue in position 444 of wild-type, full-length Htt polypeptide is a lysine, and this lysine in the wild-type, full-length polypeptide and the residue that corresponds to this position in fragments and in mutated forms of Htt may be referred to herein as “K444”. Htt in which the K444 residue is acetylated may be referred to herein as K444-acetylated Htt. As used herein the term “K444-acetylated Htt polypeptide” is an Htt polypeptide that is acetylated at the lysine that corresponds to the K444 residue of full-length, wild-type Htt polypeptide.

The use of nomenclature to describe the position of acetylated residues herein can be further exemplified with a fragment of a full-length Htt polypeptide that includes an acetylated lysine residue. One such acetylated Htt polypeptide is set forth as CRKQKGKVLLG (SEQ ID NO:13). An non-acetylated Htt polypeptide having the same amino acid sequence as SEQ ID NO:13 is set forth as CRKQKGKVLLG (SEQ ID NO:53). The lysine that is residue 7 (K7) of SEQ ID NO:13 corresponds to the lysine that is residue 444 (K444) of the wild-type, full-length Htt polypeptide amino acid sequence, thus the acetylated amino acid residue in SEQ ID NO:13 may be referred to as the K7 residue of SEQ ID NO:13, or as the residue that corresponds to the K444 residue of full-length wild-type Htt polypeptide. Those of ordinary skill in the art can readily determine the correspondence of an acetylated residue in an Htt polypeptide sequence (wild-type or mutant) with a residue in a full-length, wild-type Htt polypeptide using routine sequence comparison methods.

In some aspects, the invention may include the synthesis of acetylated full-length polypeptides or acetylated fragments thereof. Synthesis methods of the invention may include any art-known synthetic methods such as the acetylation of a existing natural or synthetic Htt polypeptide, or the incorporation of an acetylated lysine residue in an Htt polypeptide during synthesis. Incorporation of acetylated lysine may include the following acetylation step, which occurs at the ϵ-amino groups of lysines:

$$\text{Lysine+acetyl–CoA->Acetyl–Lysine+}H_2O$$

In some aspects, the invention may include the synthesis of acetylated full-length Htt polypeptides or acetylated fragments thereof.

As used herein with respect to polypeptides, proteins, or fragments thereof, “isolated” means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may be, but need not be, substantially pure. The term “substantially pure” means that the proteins or polypeptides are essentially free of other substances with which they may be found in production, nature, or in vivo systems to an extent practical and appropriate for their intended use. Substantially pure polypeptides may be obtained naturally or produced using methods described herein and may be purified with techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be associated in living systems, i.e. isolated from other proteins.

According to some aspects of the invention, fragments of full-length, wild-type or mutant Htt polypeptides are provided. Fragments of the invention are preferably fragments that retain a distinct functional capability of the polypeptide. Functional capabilities which can be retained in a fragment include interaction with antibodies, and interaction with other polypeptides or fragments thereof (e.g., interaction with the histone acetyltransferase [HAT] domain of CRB-binding protein [CBP], etc.). Polypeptide fragments can be synthesized using art-known methods, and tested for function using the methods exemplified herein.

A fragment of an acetylated Htt polypeptide may comprise at least 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, 1000, or more (including each integer in between) contiguous amino acids of Htt polypeptide having a consecutive sequence found in wild-type Htt polypeptide or a modified Htt polypeptide sequence as described herein. In some embodiments, a fragment includes a lysine residue that corresponds to K444 of full-length, wild-type Htt polypeptide. A residue that corresponds to K444 may or may not be acetylated. Fragments of acetylated Htt polypeptide can be prepared using synthetic methods known in the art or may be natural fragments of acetylated Htt polypeptides. Such fragments are useful for a variety of purposes, including in the preparation of molecules that bind specifically to synthetic and naturally acetylated Htt polypeptides and in immunoassays well known to those of ordinary skill in the art, including competitive binding immunoassays.

Non-limiting examples of fragments of Htt polypeptide that include a lysine that corresponds to the K444 of full-length, wild-type Htt are QKGKVLL (SEQ ID NO:14); KQKGKVLL 9SEQ ID NO:15); SRKQKGKVLLG (SEQ ID NO:16) KGKVLLGEEEALE (SEQ ID NO;19); QKGKVLLGEEEALE (SEQ ID NO:20); SIVELIAGGGSSCSPVLSRKQKGKVLLGEEALEDDSESRSDVSSSALTA (SEQ ID NO:21); IVELIAGGGSSCSPVLSRKQKGKVLLGEEEALEDDSESRS DVSSSALT (SEQ ID NO;22); VELIAGGGSSCSPVLSRKQKGKVLLGEEEALEDDSESRSDVSSSALTA (SEQ ID NO;23); GGSSCSPVLSRKQKGKVLLGEEEALEDDSESRSDVSSSALTA (SEQ ID NO:24); CSPV; RKQKGKVLLGEEEALEDDSERSDVSSSALTA (SEQ ID NO:25); SIVELIAGGGSSCSPVLSRKQKGKVLLGEEEALEDDS (SEQ ID NO:26); SIVELIAGGGSSCSPVLSRKQKGKVLLGEEEALEDDSESR (SEQ ID NO:27); SIVELIAGGGSSCSPVLSRKQKGKVLLGEEEALEDDSESRSDVSS (SEQ ID NO:28); SIVELIAGGGSSCSPVLSRKQKGKVLLGEEEALEDDSESRSDVSSS (SEQ ID NO:29); ELIAGGGSSCSPVLSRKQKGKVLLGEEEALEDDSESRS (SEQ ID NO:30); SCSPVLSRKQKGKVLLGEEALEDDSESRSDVSS (SEQ ID NO:31) SIVELIAGGGSSCSPVLSRKQKGKVLLGEEEALEDDSESR DVSS (SEQ ID NO:32 ); VLSRKQKGKVLLGEE (SEQ ID NO:33); CSPVLSRKQKGKVLLGEEEALEDDSESRSDVSSSALTA (SEQ ID NO:34); GGSSCSPVLSRKQKGKVLLGEEEA (SEQ ID NO:35); GSSCSPVLSRKQKGK (SEQ ID NO:36); KGKVLLGEEEALEDD (SEQ ID NO:37); SSCSPVLSRKQKGKVLLGEEEALEDDSESRSDVSSSALTA (SEQ ID NO:38); SSCSPVLSRKQKGKVLLGEEEALEDDSESR (SEQ ID NO:39); LIAGGGSSCSPVLSRKQKGKVLLGEEE (SEQ ID NO:40); VLSRKQKGKVLLGEEEALEDDSERSRSDVSSSALTA (SEQ ID NO:41); SSCSPVLSRKQKGKVLLGEEALEDDSES (SEQ ID NO:42); CSPVLSRKQKGKVLLGEEEALEDD (SEQ ID NO:43); SSCSPVLSRKQKGKVLLGE (SEQ ID NO:44); KQKGKVLLGEEEALEDD (SEQ ID NO:45); SCSPVLSRKQKGKVLLGE (SEQ ID NO:46); and VELIAGGGSSCSPVLSRKQKGKVLLGEEALEDDSESRSDVSSSAL (SEQ ID NO:47).

One of ordinary skill in the art will understand how to prepare additional fragments of full-length wild-type or mutant Htt polypeptide. An acetylated fragment of a full-length wild-type or mutant Htt polypeptide may include an acetylated lysine that corresponds to the K444 lysine of full-length wild-type Htt polypeptide and/or may include an acetylated lysine that corresponds to a different lysine of full-length wild-type Htt polypeptide. Also, in some embodiments of the invention, a fragment of Htt polypeptide may include a K444 residue and one or more additional lysine residues, and one, each, some, or none of the lysines may be acetylated.

One of ordinary skill in the art will recognize that an Htt polypeptide fragment that includes a lysine residue that corresponds to K444 of full-length, wild-type Htt polypeptide may be a polypeptide that includes a lysine residue that corresponds to the K444 residue of full-length, wild-type Htt polypeptide with an additional 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377 378, 379, 380, 381, 382, 383, 384, 385, 386, 387, 388, 389, 390, 391, 392, 392, 394, 395, 396, 397, 398, 399, 400 or more amino acids, including all integers up to the sequence of a full-length wild-type or mutant Htt polypeptide minus one amino acid. The additional amino acids may be added to either and/or both the N-terminus or the C-terminus of the lysine that corresponds to a K444 amino acid, such that the amino acid sequence corresponds to an amino acid sequence of a wild-type or mutant Htt polypeptide, or a modified wild-type or mutant Htt polypeptide.

A "modified" wild-type or mutant Htt polypeptide or fragment thereof may include deletions, point mutations, truncations, amino acid substitutions and/or additions of amino acids or non-amino acid moieties. Modifications of a polypeptide of the invention may be made by modification of the nucleic acid that encodes the polypeptide or alternatively, modifications may be made directly to the polypeptide, such as by cleavage, addition of a linker molecule, addition of a detectable moiety, such as biotin, addition of a carrier molecule, and the like. Modifications also embrace fusion proteins comprising all or part of the polypeptide's amino acid sequence.

In general, modified Htt polypeptides include polypeptides that are modified specifically to alter a feature of the polypeptide unrelated to its physiological activity. For example, cysteine residues can be substituted or deleted to prevent unwanted disulfide linkages. Polypeptide modifications can be made by selecting an amino acid substitution, deletion, and/or addition, and a modified polypeptide may be synthesized using art-known methods. Modified polypeptides then can be tested for one or more activities (e.g., antibody binding, antigenicity, etc., ability to interact with the HAT domain of CBP, etc.) to determine which modification provides a modified polypeptide with the desired properties.

The skilled artisan will also realize that conservative amino acid substitutions may be made in a polypeptide to provide functionally equivalent polypeptides, i.e., modified Htt polypeptides that retain a functional capability of a wild-type or mutant Htt polypeptide. As used herein, a "conservative amino acid substitution" refers to an amino acid substitution that does not alter the relative charge or size characteristics of the protein in which the amino acid substitution is made. Modified Htt polypeptides can be prepared according to methods for altering polypeptide sequence and known to one of ordinary skill in the art such. Exemplary functionally equivalent Htt polypeptides include conservative amino acid substitutions of an Htt polypeptide, or fragments thereof, such as a modified Htt polypeptide. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Conservative amino-acid substitutions in an Htt polypeptide typically are made by alteration of a nucleic acid encoding the polypeptide. Such substitutions can be made by a variety of methods known to one of ordinary skill in the art. For example, amino acid substitutions may be made by PCR-directed mutation, site-directed mutagenesis, or by chemical synthesis of a gene encoding the Htt polypeptide. Where amino acid substitutions are made to a small fragment of a polypeptide, the substitutions can be made by directly synthesizing the polypeptide. The activity of functionally equivalent fragments of Htt polypeptides can be tested by cloning the gene encoding the altered polypeptide into a bacterial or mammalian expression vector, introducing the vector into an appropriate host cell, expressing the altered polypeptide, and testing for a functional capability of the polypeptide as disclosed herein.

As described above, a fragment of a full-length wild-type or mutant Htt polypeptide may be a synthetic polypeptide. As used herein, the term "synthetic" means artificially prepared. A synthetic polypeptide is a polypeptide that is synthesized and is not a naturally produced polypeptide molecule (e.g., not produced in an animal or organism). It will be understood that the sequence of a natural polypeptide (e.g., an endogenous polypeptide) may be identical to the sequence of a synthetic polypeptide, but the latter will have been prepared using at least one synthetic step.

As used herein, a synthetic acetylated polypeptide is a polypeptide acetylated with a synthetic method, which may be, but is not limited to a method of the invention. An acetylated polypeptide of the invention may be a naturally acetylated polypeptide (e.g., an endogenous acetylated polypeptide) or may be a synthetic acetylated polypeptide. Although a synthetic acetylated polypeptide may differ from a natural acetylated polypeptide, an antibody raised against a synthetic polypeptide of the invention will specifically bind with high affinity the synthetic polypeptide epitope against which it was raised, and will also specifically bind with high affinity the natural epitope in a polypeptide. For example, an antibody of the invention raised against a synthetic acetylated polypeptide prepared using methods of the invention, and including the amino acid sequence CRKQKGKVLLG (SEQ ID NO:13), is able to specifically bind with high affinity to a synthetic polypeptide that comprises the amino acid sequence CRKQKGKVLLG (SEQ ID NO:13) and also is able to specifically bind to a natural polypeptide that comprises the amino acid sequence CRKGKGKVLLG (SEQ ID NO:13). Thus, even though an acetylated epitope of a synthetic polypeptide may differ slightly in amino acid sequence from the same epitope in a natural acetylated polypeptide, an antibody raised against an synthetic acetylated epitope of the invention specifically binds, in most cases, with high affinity to the natural acetylated epitope and to a synthetic acetylated epitope. Antibodies of the invention generated using a synthetic acetylated polypeptide specifically bind, in most cases, with high affinity to natural and synthetic acetylated polypeptides and are able to distinguish between natural (heterogeneous) acetylated and natural non-acetylated polypeptides and also to distinguish between synthetic acetylated and synthetic non-acetylated polypeptides.

The invention includes in one aspect, methods and compositions for preparing antibodies that specifically bind synthetic and natural acetylated Htt. The invention includes, in part, methods for preparing acetylated Htt polypeptides, including, but not limited to K444-acetylated Htt polypeptides. Acetylated Htt polypeptides may be used as antigens to make antibodies that specifically bind acetylated Htt polypeptide. Compositions useful for making an antibody of the invention may include an acetylated Htt polypeptide molecule. In embodiments of the invention, an acetylated Htt polypeptide or fragment thereof may be an acetylated full-length, wild-type or mutant Htt polypeptide, or a fragment of a wild-type or mutant full-length Htt that is an acetylated fragment.

Methods of the invention may also include the use of fragments of Htt polypeptides for the production of antibodies that specifically bind acetylated Htt polypeptides. In some embodiments, an acetylated lysine residue of an Htt polypeptide that is part of the epitope specifically recognized by the antibody is a lysine residue that corresponds to an acetylated residue of wild-type, full-length Htt polypeptide. In some embodiments, an acetylated residue corresponds to residue K444 of wild-type, full-length Htt polypeptide. In some embodiments, an antigenic polypeptide can be as small as 5 amino acids in length. For example, KGKVL (SEQ ID NO:48), KQKGK (SEQ ID NO:49), QKGKV (SEQ ID NO:50); GKVLL (SEQ ID NO:51); and KVLLG (SEQ ID NO:52) are examples of acetylated antigenic fragments that may be used to generate antibodies that specifically recognize a K444-acetylated Htt polypeptide. In some embodiments, when the size of the polypeptide antigen is less than about 8 amino acids in length, a second carrier molecule, e.g., bovine serum albumin (BSA), may be attached to the polypeptide to increase antigenicity of the polypeptide. Thus, small fragments of Htt that include the desired epitope for antibody production can be used in the production of an antibody that specifically binds to the epitope, which includes an acetylated lysine residue (e.g., a K444-acetylated residue).

In one embodiment, antibodies that specifically bind CRKQKGKVLLG (SEQ ID NO:13), are provided. For example, the antibody AcK444 specifically binds to the acetylated CRKQKGKVLLG (SEQ ID NO:13), but not to non-acetylated SEQ ID NO:53, as determined by the dot blot assay. The AcK444 antibody specifically binds wild-type and/or mutant Htt polypeptides, as long as they include an acetylated lysine residue that corresponds to the K444 residue of full-length wild-type Htt polypeptide and sufficient elements of the CRKQKGKVLLG (SEQ ID NO:13) motif. In the preparation of antibodies that specifically bind to K444-acetylated Htt, CRKQKGKVLLG (SEQ ID NO:13) or other Htt polypeptide fragments that include an acetylated K444 residue may be used. Any Htt polypeptide fragment that includes an acetylated lysine residue may be used in conjunction with a second molecule, e.g., keyhole limpet hemocyanin (KLH) or bovine serum albumin (BSA) as described above, as an antigenic polypeptide with which to prepare antibodies that specifically bind to an acetylated Htt polypeptide. In some embodiments, an antigenic polypeptide may be an Htt polypeptide fragment that includes acetylated K444, and an antibody generated from such an antigen will specifically bind to a K444-acetylated epitope of Htt polypeptide. Anti-Htt polypeptide antibodies or antigen-binding fragments thereof may be purified using art-known affinity purification and/or affinity selection methods. Affinity selection is selection of antibodies or antigen-binding fragments thereof for binding to the target material (e.g., an acetylated Htt polypeptide).

It will be understood by those of ordinary skill in the art that it is preferable that a fragment of Htt polypeptide for use as an immunogenic fragment in the methods of the invention be at least 5, 6, 7, 8, 9, 10, 11, 12, 13, 14, 15, 16, 17, 18, 19, 20 or more amino acids in length. If a fragment of Htt polypeptide includes more than one lysine residue, it is desirable that in some embodiments, only one of the lysine residues is an acetylated lysine residue. One of ordinary skill in the art will be able to use the guidance provided herein to make additional fragments of Htt polypeptide that can be used in methods of the invention.

As used herein, the term "antibody" refers to a glycoprotein that may include at least two heavy (H) chains and two light (L) chains inter-connected by disulfide bonds. Each heavy chain is comprised of a heavy chain variable region (abbreviated herein as HCVR or $V_H$) and a heavy chain constant region. The heavy chain constant region is comprised of three domains, $C_H1$, $C_H2$ and $C_H3$. Each light chain is comprised of a light chain variable region (abbreviated herein as LCVR or $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding fragment" of an antibody as used herein, refers to one or more portions of an antibody that retain the ability to specifically bind to an antigen (e.g., acetylated Htt polypeptide and in some embodiments, the acetylated Htt polypeptide is K444-acetylated Htt polypeptide or corresponding residue in an Htt polypeptide fragment). It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the $V_L$, $V_H$, $C_L$ and $C_H1$ domains; (ii) a $F(ab')_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) *Nature* 341:544-546) which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional procedures, such as proteolytic fragmentation procedures, as described in J. Goding, Monoclonal Antibodies: Principles and Practice, pp 98-118 (N.Y. Academic Press 1983), which is hereby incorporated by reference as well as by other techniques known to those with skill in the art. The fragments are screened for utility in the same manner as are intact antibodies.

Isolated antibodies of the invention encompass various antibody isotypes, such as IgG1, IgG2, IgG3, IgG4, IgM, IgA1, IgA2, IgAsec, IgD, IgE. As used herein, "isotype" refers to the antibody class (e.g., IgM or IgG1) that is encoded by heavy chain constant region genes. Antibodies of the invention can be full length or can include only an antigen-binding fragment such as the antibody constant and/or variable domain of IgG1, IgG2, IgG3, IgG4, IgM, IgA1, IgA2, IgAsec, IgD or IgE or could consist of a Fab fragment, a $F(ab')_2$ fragment, and a Fv fragment.

Antibodies of the present invention can be polyclonal, monoclonal, or a mixture of polyclonal and monoclonal antibodies. Antibodies of the invention can be produced by methods disclosed herein or by a variety of techniques known in the art. An example of a method to produce an antibody that specifically binds K444-acetylated Htt is provided in the Examples section and is discussed further herein. In some embodiments, the epitope recognized by an antibody of the invention includes acetylated lysine that corresponds to the K444 in full-length, wild-type Htt polypeptide. In some embodiments, the epitope recognized by an antibody of the invention comprises an acetylated residue that corresponds to K444 of wild-type, full-length Htt polypeptide.

Polyclonal and monoclonal antibodies may be prepared using techniques described in the Examples section and/or with alternative methods that are known in the art. The Examples section provides methods of producing a polyclonal antibody that specifically binds to K444-acetylated Htt polypeptide. The term "monoclonal antibody," as used herein, refers to a preparation of antibody molecules of single molecular composition. A monoclonal antibody displays a single binding specificity and affinity for a particular epitope. A monoclonal antibody displays a single binding specificity and affinity for a particular epitope. The term "polyclonal antibody" refers to a preparation of antibody molecules that comprises a mixture of antibodies active that specifically bind a specific antigen.

A process of monoclonal antibody production may include obtaining immune somatic cells with the potential for producing antibody, in particular B lymphocytes, which have been previously immunized with the antigen of interest either in vivo or in vitro and that are suitable for fusion with a B-cell myeloma line. Mammalian lymphocytes typically are immunized by in vivo immunization of the animal (e.g., a mouse) with the desired protein or polypeptide, e.g., with acetylated Htt polypeptide or a fragment thereof, or K444-acetylated Htt or a fragment thereof in the present invention. In some embodiments, the polypeptide is a modified polypeptide as described herein. In some embodiments the polypeptide comprises the sequence set forth as SEQ ID NO:13. Such immunizations are repeated as necessary at intervals of up to several weeks to obtain a sufficient titer of antibodies. Once immunized, animals can be used as a source of antibody-producing lymphocytes. Following the last antigen boost, the animals are sacrificed and spleen cells removed. Mouse lymphocytes give a higher percentage of stable fusions with the mouse myeloma lines described herein. Of these, the BALB/c mouse is preferred. However, other mouse strains, rat, rabbit, hamster, sheep, goats, camels, llamas, frogs, etc. may also be used as hosts for preparing antibody-producing cells. See; Goding (in Monoclonal Antibodies: Principles and Practice, 2d ed., pp. 60-61, Orlando, Fla., Academic Press, 1986). Mouse strains that have human immunoglobulin genes inserted in the genome (and which cannot produce mouse immunoglobulins) can also be used. Examples include the HuMAb mouse strains produced by Medarex/GenPharm International, and the XenoMouse strains produced by Abgenix. Such mice produce fully human immunoglobulin molecules in response to immunization.

Those antibody-producing cells that are in the dividing plasmablast stage fuse preferentially. Somatic cells may be obtained from the lymph nodes, spleens and peripheral blood of antigen-primed animals, and the lymphatic cells of choice depend to a large extent on their empirical usefulness in the particular fusion system. The antibody-secreting lymphocytes are then fused with (mouse) B cell myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature* 256:495 (1975), which is hereby incorporated by reference.

Myeloma cell lines suited for use in hybridoma-producing fusion procedures preferably are non-antibody-producing, have high fusion efficiency, and enzyme deficiencies that render them incapable of growing in certain selective media which support the growth of the desired hybridomas. Examples of such myeloma cell lines that may be used for the production of fused cell lines include, but are not limited to Ag8, P3-X63/Ag8, X63-Ag8.653, NS1/1.Ag 4.1, Sp2/0-Ag14, FO, NSO/U, MPC-11, MPC11-X45-GTG 1.7, S194/5XX0 Bul, all derived from mice; R210.RCY3, Y3-Ag 1.2.3, IR983F and 4B210 derived from rats and U-266, GM1500-GRG2, LICR-LON-HMy2, UC729-6, all derived from humans (Goding, in Monoclonal Antibodies: Principles and Practice, 2d ed., pp. 65-66, Orlando, Fla., Academic Press, 1986; Campbell, in Monoclonal Antibody Technology, Laboratory Techniques in Biochemistry and Molecular Biology Vol. 13, Burden and Von Knippenberg, eds. pp. 75-83, Amsterdam, Elsevier, 1984). Those of ordinary skill in the art will be aware of numerous routine methods to produce monoclonal antibodies.

Fusion with mammalian myeloma cells or other fusion partners capable of replicating indefinitely in cell culture is effected by standard and well-known techniques, for example, by using polyethylene glycol ("PEG") or other fusing agents (See Milstein and Kohler, *Eur. J. Immunol.* 6:511 (1976), which is hereby incorporated by reference).

An example of a procedure for raising polyclonal antibodies is provided in the Examples section herein and there are also alternative methods that are well known to those of ordinary skill in the art. As a non-limiting example, anti-acetylated Htt polyclonal antibodies may be raised by administering an acetylated Htt polypeptide subcutaneously to New Zealand white rabbits which have first been bled to obtain pre-immune serum. The acetylated Htt can be inoculated with (e.g., injected at) a total volume of 100 μl per site at six different sites, typically with one or more adjuvants. The rabbits are then bled two weeks after the first injection and periodically boosted with the same antigen three times every six weeks. A sample of serum is collected 10 days after each boost. Polyclonal antibodies are recovered from the serum, preferably by affinity chromatography using acetylated Htt to capture the antibody. This and other procedures for raising polyclonal antibodies are disclosed in E. Harlow, et al., editors, Antibodies: A Laboratory Manual (1988), which is hereby incorporated by reference. Those of ordinary skill in the art will be aware of numerous routine methods to produce polyclonal antibodies. In some embodiments, the epitope recognized by the polyclonal antibody of the invention comprises an acetylated residue that corresponds to K444 of wild-type, full-length Htt polypeptide.

In other embodiments, antibodies may be recombinant antibodies. The term "recombinant antibody", as used herein, is intended to include antibodies that are prepared, expressed, created or isolated by recombinant means, such as antibodies isolated from an animal (e.g., a mouse) that is transgenic for another species' immunoglobulin genes, genetically engineered antibodies, antibodies expressed using a recombinant expression vector transfected into a host cell, antibodies isolated from a recombinant, combinatorial antibody library, or antibodies prepared, expressed, created or isolated by any other means that involves splicing of immunoglobulin gene sequences to other DNA sequences.

The present invention further provides nucleic acid molecules encoding anti-acetylated Htt antibodies (e.g., anti-K444-acetylated Htt antibodies) and vectors comprising the nucleic acid molecules as described herein. The vectors provided can be used to transform or transfect host cells for producing anti-acetylated Htt antibodies with the specificity of antibodies described herein. In an important embodiment the antibodies produced will have the specificity of the AcK444 antibody. In some embodiments, the vectors can include an isolated nucleic acid molecule encoding a heavy chain and/or a light chain of an antibody of the invention encoded by a nucleic acid molecule. In a further embodiment, plasmids are given which produce the antibodies or antigen-binding fragments described herein.

Antibodies or antigen-binding fragments of the invention are, preferably, isolated. "Isolated", as used herein with respect to antibodies and antigen-binding fragments thereof, is intended to refer to an antibody (or antigen-binding fragment thereof) that is substantially free of other antibodies (or antigen-binding fragments) having different antigenic specificities (e.g., an isolated antibody that specifically binds to acetylated Htt polypeptide is substantially free of antibodies that specifically bind antigens other than acetylated Htt polypeptide). An isolated antibody that specifically binds to an epitope, isoform or variant of a acetylated polypeptide (e.g., acetylated Htt polypeptide) may, however, have cross-reactivity to other related antigens, e.g., a mutant form of Htt, or a polypeptide from other species (e.g., Htt species homologs). Moreover, an isolated antibody (or antigen-binding fragment thereof) may be substantially free of other cellular material and/or chemicals.

Antibodies of the invention include, but are not limited to antibodies that specifically bind to an acetylated Htt polypeptide. In certain embodiments, an antibody of the invention specifically binds Htt that is acetylated at reside that corresponds to the K444 residue of full-length, wild-type Htt polypeptide. As used herein, "specific binding" refers to antibody binding to a predetermined antigen with a preference that enables the antibody to be used to distinguish the antigen from others to an extent that permits the diagnostic and other assays described herein. Specific binding to K444-acetylated Htt polypeptide means that the antibody not only preferentially binds Htt polypeptide versus other polypeptides, but also that it preferentially binds an acetylated Htt polypeptide versus an Htt polypeptide that is not acetylated. Typically, the antibody binds with an affinity that is at least two-fold greater than its affinity for binding to antigens other than the predetermined antigen. In some embodiments, an antibody or antigen-binding fragment thereof of the invention specifically binds to K444-acetylated Htt polypeptide. It will be understood that the Htt polypeptide or fragment thereof that includes an acetylated residue that corresponds to acetylated K444 of full-length, wild-type Htt polypeptide, may be a wild-type or a mutant form of Htt polypeptide—as long as the epitope recognized by an antibody that specifically binds an acetylated Htt polypeptide residue that includes a residue corresponding to acetylated K444 residue of full-length, wild-type Htt polypeptide is present.

Anti-K444-acetylated Htt antibodies or antigen-binding fragments thereof, of the invention, can specifically bind K444-acetylated Htt polypeptide with sub-nanomolar affinity. The binding affinities can be about $1\times10^{-6}$, $1\times10^{-7}$, $1\times10^{-8}$, $1\times10^{-9}$M or less, preferably about $1\times10^{-10}$M or less, more preferably $1\times10^{-11}$M or less. In a particular embodiment the binding affinity is less than about $5\times10^{10}$M.

In some aspects of the invention, an antibody or antigen-binding fragment thereof binds to a conformational epitope within the acetylated Htt polypeptide. To determine if the selected anti-acetylated Htt antibodies bind to conformational epitopes, each antibody can be tested in assays using native protein (e.g., non-denaturing immunoprecipitation, flow cytometric analysis of cell surface binding) and denatured protein (e.g., Western blot, immunoprecipitation of denatured proteins). A comparison of the results will indicate whether the antibodies bind conformational epitopes. Antibodies that bind to native protein but not denatured protein are those antibodies that bind conformational epitopes, and are preferred antibodies.

In some embodiments of the invention, antibodies competitively inhibit the specific binding of a second antibody to its target acetylated epitope on acetylated Htt polypeptide. In some embodiments, the target epitope comprises an acetylated residue that corresponds to K444 of wild-type, full-length Htt polypeptide. In some embodiments, the second antibody is AcK444. To determine competitive inhibition, a variety of assays known to one of ordinary skill in the art can be employed. For example, competition assays can be used to determine if an antibody competitively inhibits binding to acetylated Htt (or K444-acetylated Htt) by another antibody (e.g., AcK444). These methods may include cell-based methods employing flow cytometry or solid phase binding analysis. Other assays that evaluate the ability of antibodies to cross-compete for acetylated Htt polypeptide (or K444-acetylated Htt polypeptide) molecules in solid phase or in solution phase, also can be used.

Certain antibodies competitively inhibit the specific binding of a second antibody to its target epitope on acetylated Htt polypeptide (or K444-acetylated Htt polypeptide) by at least about 10%, 20%, 30%, 40%, 50%, 60%, 70%, 80%, 90%, 95%, or 99%. Inhibition can be assessed at various molar ratios or mass ratios; for example competitive binding experiments can be conducted with a 2-fold, 3-fold, 4-fold, 5-fold, 7-fold, 10-fold or more molar excess of the first antibody over the second antibody.

Other antibodies of the invention may include antibodies that specifically bind to an epitope on acetylated Htt polypeptide defined by a second antibody. To determine the epitope, one can use standard epitope mapping methods known in the art. For example, fragments (polypeptides) of K444-acetylated Htt polypeptide antigen that bind the second antibody can be used to determine whether a candidate antibody binds the same epitope. In some embodiments, an epitope comprises an acetylated residue that corresponds to K444 of wild-type, full-length Htt polypeptide. In one embodiment, the second antibody is AcK444. For linear epitopes, overlapping polypeptides of a defined length (e.g., 5, 6, 7, 8 or more amino acids) may be synthesized. The polypeptides preferably are offset by 1 amino acid, such that a series of polypeptides covering every 4, 5, 6, 7, or 8 amino acid fragment (respectively) of the acetylated Htt polypeptide sequence are prepared. Fewer polypeptides can be prepared by using larger offsets, e.g., 2 or 3 amino acids. In addition, longer polypeptides (e.g., 9-, 10- or 11-mers) can be synthesized. Binding of polypeptides to antibodies can be determined using standard methodologies including surface plasmon resonance (BIACORE) and ELISA assays. For examination of conformational epitopes, larger acetylated Htt polypeptide fragments, including in some embodiments K444-acetylated Htt polypeptide, can be used. Other methods that use mass spectrometry to define conformational epitopes have been described and can be used (see, e.g., Baerga-Ortiz et al., *Protein Science* 11: 1300-1308, 2002 and references cited therein). Still other methods for epitope determination are provided in standard laboratory reference works, such as Unit 6.8 ("Phage Display Selection and Analysis of B-cell Epitopes") and Unit 9.8 ("Identification of Antigenic Determinants Using Synthetic Polypeptide Combinatorial Libraries") of *Current Protocols in Immunology*, Coligan et al., eds., John Wiley & Sons. Epitopes can be confirmed by introducing point mutations or deletions into a known epitope, and then testing binding with one or more antibodies to determine which mutations reduce binding of the antibodies.

An antibody or antigen-binding fragment thereof of the invention can be linked to a detectable label. A detectable label of the invention may be attached to antibodies or antigen-binding fragments thereof of the invention by standard protocols known in the art. In some embodiments, the detectable labels may be covalently attached to an anti-acetylated Htt antibody or antigen-binding fragment thereof of the invention. The covalent binding can be achieved either by direct condensation of existing side chains or by the incorporation of external bridging moieties. Many bivalent or polyvalent agents are useful in coupling protein molecules to other proteins, polypeptides or amine functions, etc. For example, the literature is replete with coupling agents such as carbodiimides, diisocyanates, glutaraldehyde, and diazobenzenes. This list is not intended to be exhaustive of the various coupling agents known in the art but, rather, is exemplary of the more common coupling agents. Additional descriptions of detectable labels useful in the invention are provided elsewhere herein.

The invention, in part, also includes nucleic acid sequences that encode polypeptide sequences for use in generating antibodies. For example, the invention includes nucleic acid sequences that encode an Htt polypeptide or fragment thereof, and includes the use of the nucleic acid sequences that may be used to produce polypeptides that can be used as antigens with which to raise antibodies that recognize acetylated Htt polypeptides.

Additional nucleic acids of the invention include nucleic acids that encode an Htt polypeptide, or an antibody or antigen-binding fragment thereof of the invention. In certain embodiments, a nucleic acid of the invention is a nucleic acid molecule that is highly homologous to a nucleic acid that encodes an Htt polypeptide or an antibody or antigen-binding fragment thereof of the invention. Preferably the homologous nucleic acid molecule comprises a nucleotide sequence that is at least about 90% identical to the nucleotide sequence that encodes the Htt polypeptide or antibody or antigen-binding fragment thereof. More preferably, the nucleotide sequence is at least about 95% identical, at least about 97% identical, at least about 98% identical, or at least about 99% identical to a nucleotide sequence that encodes an Htt polypeptide or an antibody or antigen-binding fragment thereof of the invention. The homology can be calculated using various, publicly available software tools well known to one of ordinary skill in the art. Exemplary tools include the BLAST system available from the website of the National Center for Biotechnology Information (NCBI) at the National Institutes of Health. Similarly, the amino acid sequence of a polypeptide useful in methods and compositions of the invention may be at least about 90% identical to the amino acid sequence of an Htt polypeptide. The amino acid sequence may be at least about 95% identical, at least about 97% identical, at least about 98% identical, or at least about 99% identical to an amino acid sequence of an Htt polypeptide of the invention.

One method of identifying highly homologous nucleotide sequences is via nucleic acid hybridization. Thus the invention also includes antibodies having acetylated Htt-binding properties (including but not limited to K444-acetylated Htt polypeptide-binding properties) and other functional properties described herein, and includes additional Htt polypeptides that are encoded by nucleic acid molecules that hybridize under high stringency conditions to a nucleic acid that encodes an antibody or antigen-binding fragment thereof of the invention, or an Htt polypeptide of the invention, respectively. Identification of related sequences can also be achieved using polymerase chain reaction (PCR) and other amplification techniques suitable for cloning related nucleic acid sequences. Preferably, PCR primers are selected to amplify portions of a nucleic acid sequence of interest, such as a CDR.

The term "high stringency conditions" as used herein refers to parameters with which the art is familiar. Nucleic acid hybridization parameters may be found in references that compile such methods, e.g., *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. One example of high-stringency conditions is hybridization at 65° C. in hybridization buffer (3.5×SSC, 0.02% Ficoll, 0.02% polyvinyl pyrrolidone, 0.02% Bovine Serum Albumin, 2.5 mM $NaH2PO_4$(pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, a membrane upon which the nucleic acid is transferred is washed, for example, in 2×SSC at room temperature and then at 0.1-0.5×SSC/0.1×SDS at temperatures up to 68° C.

Polypeptides and/or nucleic acids of the invention may be detectably labeled for use in methods and/or compositions of the invention. A wide variety of detectable labels are available for use in methods of the invention and may include labels that provide direct detection (e.g., fluorescence, colorimetric, or optical, etc.) or indirect detection (e.g., enzyme-generated luminescence, epitope tag such as the FLAG epitope, enzyme tag such as horseradish peroxidase, labeled antibody, etc.). A variety of methods may be used to detect a detectable label depending on the nature of the label and other assay components. Labels may be directly detected through optical or electron density, radioactive emissions, nonradiative energy transfers, etc. or indirectly detected with antibody conjugates, strepavidin-biotin conjugates, etc. Methods for using and detecting labels are well known to those of ordinary skill in the art. Methods of the invention may be used for in vivo, in vitro, and/or ex vivo imaging, including but not limited to real-time imaging. The presence of a labeled antibody in a subject can be detected by in vivo, ex vivo, or in vitro imaging using standard methods. Examples of detection methods include, but are not limited to, MRI, functional MRI, X-Ray detection, PET, CT imaging, immunohistochemistry, Western blot of tissues or cells, or by any other suitable detection method.

The term "detectable label" as used here means a molecule preferably selected from, but not limited to, fluorescent, enzyme, radioactive, metallic, biotin, chemiluminescent, and bioluminescent molecules. As used herein, a detectable label may be a colorimetric label, e.g., a chromophore molecule. In some aspects of the invention, a polypeptide or an antibody may be detectably labeled with a single or with two or more of the detectable labels set forth herein, or other art-known detectable labels.

Radioactive or isotopic labels may be, for example, $^{14}C$, $^{3}H$, $^{35}S$, $^{125}I$, and $^{32}P$. Fluorescent labels may be any compound that emits an electromagnetic radiation, preferably visible light, resulting from the absorption of incident radiation and persisting as long as the stimulating radiation is continued.

Examples of fluorescent labels that may be used on polypeptides and/or antibodies of the invention and in methods of the invention include but are not limited to 2,4-dinitrophenyl, acridine, cascade blue, rhodamine, 4-benzoylphenyl, 7-nitrobenz-2-oxa-1,3-diazole, 4,4-difluoro-4-bora-3a,4a-diaza-3-indacene and fluorescamine. Absorbance-based labels may be molecules that are detectable by the level of absorption of various electromagnetic radiation. Such molecules may be, for example, the fluorescent labels indicated above.

Chemiluminescent labels in this invention refer to compounds that emit light as a result of a non-enzymatic chemical reaction. Methods of the invention may also include the use of a luminescent detectable diagnostic molecule such as enhanced green fluorescent protein (EGFP), luciferase (Luc), or another detectable expression product.

Enzymatic methods for detection may be used including the use of alkaline phosphatase and peroxidase. Additional enzymes may also be used for detection in methods and kits of the invention.

As used herein, fluorophores include, but are not limited to amine-reactive fluorophores that cover the entire visible and near-infrared spectrum. Examples of such fluorophores include, but are not limited to, 4-methylumbelliferyl phosphate, fluorescein isothiocyanate (FITC), tetramethylrhodamine isothiocyanate (TRITC), BODIPY dyes; Oregon Green, rhodamine green dyes; the red-fluorescent Rhodamine Red-X, Texas Red dyes; and the UV light-excitable Cascade Blue, Cascade Yellow, Marina Blue, Pacific Blue and AMCA-X fluorophores. Fluorophores may also include non-fluorescent dyes used in fluorescence resonance energy transfer (FRET).

A labeled polypeptide or antibody of the invention can be prepared from standard moieties known in the art. As is recognized by one of ordinary skill in the art, the labeling process for preparing a detectable labeled polypeptide, antibody, or fragment thereof may vary according to the molecular structure of the polypeptide or antibody and the detectable label. Methods of labeling polypeptides and/or antibodies with one or more types of detectable labels are routinely used and are well understood by those of ordinary skill in the art.

In some embodiments, it is contemplated that one may wish to first derivatize a polypeptide or antibody, and then attach the detectable label to the derivatized product. Suitable cross-linking agents for use in this manner include, for example, SPDP (N-succinimidyl-3-(2-pyridyldithio)propionate), and SMPT, 4-succinimidyl-oxycarbonyl-methyl-(2-pyridyldithio)toluene. In some embodiments, a radionuclide may be coupled to a polypeptide, antibody, or antigen-binding fragment thereof by chelation.

Compositions (e.g., acetylated polypeptides, antibodies to acetylated Htt and derivatives/conjugates thereof, etc.) of the present invention have diagnostic and therapeutic utilities. For example, these molecules can be administered to cells in culture, e.g., in vitro or ex vivo, or to a sample obtained from a subject to diagnose HD. As detailed herein, the antibodies or antigen-binding fragments thereof of the invention may be used for example to isolate and identify Htt polypeptides and/or acetylated and/or non-acetylated Htt polypeptides. The antibodies may be coupled to specific diagnostic labeling agents for imaging of the mutant and/or wild-type Htt polypeptides or fragments thereof. The antibodies or antigen-binding fragments thereof of the invention may also be used for immunoprecipitation, immunoblotting Htt and/or acetylated Htt using standard methods known to those of ordinary skill in the art.

In some embodiments, an antibody or antigen-binding fragment thereof of the invention that specifically binds to an acetylated Htt polypeptide may be in solution or may be attached to a surface (e.g., a dipstick, microtiter plate, multiwell plate, plastic, slide, card, etc.). A sample from a subject may then be applied to the substrate and the substrate is then processed to assess whether specific binding occurs between the antibody and a polypeptide or other component of the sample. As used herein a substrate may be made of a material including any synthetic or natural material. Examples of substrates of the invention may include, but are not limited to: glass, plastic, nylon, metal, paper, cardboard, filter paper, filter membranes, etc., and can be in numerous forms including, but not limited to, tubes, centrifuge tubes, cuvettes, cards, slides, dipsticks, beads, coverslips, multiwell plates, Petri plates, etc. One of ordinary skill in the art will recognize that numerous additional types of surfaces can be used in the methods of the invention.

As will be understood by one of skill in the art, a binding assay using an antibody of the invention may also be performed in solution by contacting a sample from a subject with an antibody or antigen-binding fragment thereof of the invention when the antibody or antigen-binding fragment thereof, for example in a 96-well plate, a tube, a drop on a slide, etc.

As used herein the term “attached to a surface” means chemically or biologically linked to the surface and not freely removable from a surface. Examples of attachment, though not intended to be limiting are covalent binding between the substrate and an antibody, attachment via specific biological binding, or the like. For example, “attached” in this context includes chemical linkages, chemical/biological linkages, etc. As used herein the term “covalently attached” means attached via one or more covalent bonds. As used herein the term “specifically attached” means an antibody or fragment thereof is chemically or biochemically linked to a surface as described above with respect to the definition of “attached,” but excluding all non-specific binding. In the methods of the invention, an antibody that is attached to a substrate is attached such that the antibody is not removable from the substrate without specific stripping methods or solutions. Such stripping methods may include, but are not limited to, physical methods such as scraping or heating, enzymatic methods, and chemical methods, which may include but are not limited to contacting the attached antibody and substrate with a solution such that the link between the substrate and the surface is broken and the substrate is released.

In some embodiments of the invention, an antibody or antigen-binding fragment thereof is attached to a substrate, for example a dipstick, and is contacted with a sample cell or tissue from culture or from a subject. The surface of the substrate may then be processed using procedures well known to those of skill in the art, to assess whether specific binding occurred between the antibody and a polypeptide (e.g., an acetylated Htt polypeptide) in the subject’s sample. For example, procedures may include, but are not limited to, contact with a secondary antibody, or other method that indicates the presence of specific binding.

The invention, in some aspects, includes various assays to determine levels of acetylated Htt polypeptide (e.g., K444-acetylated Htt polypeptide). Methods of the invention that are useful to determine levels of acetylated Htt polypeptide in cells, tissues, subjects, and samples (e.g., from subjects, in culture, etc,), include, but are not limited to: binding assays, such as described in the examples below; specific binding assays, such as using antibodies or antigen-binding fragments thereof of the invention that bind specifically to acetylated Htt polypeptide; gel electrophoresis; mass spectrometry; NMR; and the like. Immunoassays may be used according to the invention including, but not limited to, sandwich-type assays, competitive binding assays, one-step direct tests and two-step tests such as described in the examples. Assessment of binding of antibodies that specifically bind acetylated Htt may also be done in vivo—in living subjects using art-known detectable labels and suitable in vivo methods.

Methods and assays of the invention (e.g., binding assays, gel electrophoresis; mass spectrometry; NMR; and the like) may be used to monitor changes in Htt acetylation levels in cell sample and or a subject over time. Thus, methods of the invention may be used to examine changes in Htt acetylation levels in a subject or cell sample (e.g., cell culture) over time. This allows monitoring of acetylated Htt polypeptide levels in a subject who is believed to be at risk of developing Huntington’s disease (HD) and also enables monitoring in a subject who is known to have HD. Thus, methods of the invention may be used to diagnose or assess HD in a subject and may also be used to assess the efficacy of a therapeutic treatment of HD and for the assessment of the level of acetylated Htt polypeptide a subject at various time points. For example, a level of a subject’s acetylated Htt polypeptide can be obtained prior to the start of a therapeutic regimen (either prophylactic or as a treatment of HD), during the treatment regimen and/or after a treatment regimen, thus providing information on the effectiveness of the regimen in the patient. Assessment of efficacy of candidate therapeutic agents may also be done using assays of the invention in cells from culture—e.g., as screening assays to assess candidate therapeutic agents.

It will be understood that a therapeutic regimen may be either prophylactic or a treatment of HD in a subject. Thus, methods of the invention may be used to monitor a subject’s response to prophylactic therapy and/or treatment for HD provided to a subject. Methods of the invention (e.g., binding assays, gel electrophoresis; mass spectrometry; NMR; and the like) may also be useful to monitor the onset, progression, or regression of HD in a subject. The level of acetylated Htt polypeptide may be determined in two, three, four, or more samples obtained from a subject at separate times. The level of acetylated Htt polypeptide in the samples may be compared and changes in the levels over time may be used to assess the status and stage of HD in a subject and/or the effect of a treatment strategy on HD in a subject.

One aspect of the present invention relates to the use of the antibodies and/or antigen-binding fragments thereof of the invention for detecting acetylated Htt polypeptides or fragments thereof in an in vitro or in vivo sample (e.g., histological or cytological specimens, real-time in vivo assays, biopsies and the like), and, in particular, to distinguish the level of acetylated Htt from the level of non-acetylated Htt in a sample or a subject. This method involves providing an antibody or an antigen-binding binding fragment thereof, which specifically binds to acetylated Htt polypeptide, e.g., AcK444 or other anti-acetylated Htt antibody. The anti-acetylated Htt antibody may be bound to a label that permits the detection of the acetylated Htt polypeptide. In some embodiments, a sample may be contacted with a labeled anti-acetylated Htt antibody under conditions effective to permit binding of the anti-acetylated Htt antibody to acetylated Htt polypeptide in the sample. The presence of acetylated Htt in a sample may be detected by detection of the label. In some embodiments, the contact between the anti-acetylated Htt antibody and a sample is carried out in samples from a subject. In certain embodiments, the contact between an anti-acetylated Htt antibody and a sample may be carried out in a subject. Samples to which the methods of the invention can be applied include tissue samples, cell samples, including cell culture samples, subject samples, in vivo samples, etc.

Anti-acetylated Htt antibodies of the present invention can be used in immunohistochemical techniques to examine tissue and cell specimens. In some embodiments, the samples are fresh samples. In some embodiments, slides containing cryostat sections of frozen, unfixed tissue biopsy samples or cytological smears are air dried, formalin or acetone fixed, and incubated with an antibody preparation in a humidified chamber at room temperature. The slides are then washed and further incubated with a preparation of a secondary antibody directed against the antibody. This secondary antibody may be tagged with a detectable compound, for instance a fluorescent compound such as rhodamine or fluorescein isothiocyanate, that fluoresces at a particular wavelength. The staining pattern and intensities within the sample are then determined by standard imaging methods such as microscopy and optionally photographically recorded.

As yet another alternative, computer enhanced fluorescence image analysis or flow cytometry can be used to examine tissue specimens or cells using the anti-acetylated Htt antibodies of the invention.

In some embodiments of the invention, antibodies of the present invention can be used in combination with other known antibodies to provide additional information regarding the level of acetylated Htt polypeptide as a percentage of the level of total Htt polypeptide in a sample. For example, an antibody that binds Htt polypeptide (acetylated and non-acetylated) can be used to determine the total amount or level of Htt polypeptide in a sample, can be used in conjunction with an antibody of the invention that specifically binds an acetylated Htt to determine a percentage of total Htt in a sample that is acetylated Htt polypeptide.

The step of contacting an antibody or antigen-binding fragment thereof of the invention with a sample to be tested can be carried out in a cell or tissue sample to detect the presence of acetylated Htt polypeptide in the sample. It is preferred that an antibody or antigen-binding fragment thereof of the invention recognize substantially no antigens in the sample other than acetylated Htt polypeptide. In some embodiments, it is preferred that the antibody or antigen-binding fragment thereof of the invention recognize substantially no antigens in the sample other than K444-acetylated Htt polypeptide.

Antibodies and antigen-binding fragments thereof suitable for detecting acetylated Htt polypeptide include anti-acetylated Htt antibodies, such as monoclonal or polyclonal antibodies. In addition, antibody fragments, half-antibodies, hybrid derivatives, probes, and other molecular constructs may be utilized. In some embodiments of the invention, antibodies are anti-K444-acetylated Htt antibodies.

Antibodies or antigen-binding fragments thereof of the invention may also be used in a variety of assays based upon detecting levels of acetylated Htt in cells and/or subjects. Assays include (1) characterizing the impact of acetylated Htt polypeptide levels on HD in a subject; (2) evaluating a treatment for Htt polypeptide acetylation status in a subject; (3) selecting a treatment for HD in a subject; and (4) determining onset, progression, and/or regression of HD in a subject. Thus, subjects can be characterized, treatment regimens can be monitored, treatments can be selected and diseases status can be better understood using the assays of the present invention. For example, the antibodies or antigen-binding fragments thereof of the invention are useful in one aspect in methods for measuring the level of acetylated Htt in a cell and/or subject, which is a direct indicator of the level clearance of mutant Htt polypeptide in a cell and/or subject. The impact of the level of acetylated Htt polypeptide thus can be measured due to the positive correlation between the level of acetylated Htt polypeptide and the clearance of mutant Htt polypeptide from cells and/or tissues. The level of acetylated Htt polypeptide thus may correlate with the status of HD in a subject. Relatively high levels of acetylated Htt polypeptide reflect clearance of mutant forms of Htt polypeptide and selectively low levels of acetylated Htt polypeptide reflect less clearance of mutant Htt polypeptide from cells and/or tissues.

Antibodies and antigen-binding fragments thereof of the invention may be used in assays described herein, which are carried out in cells from culture, cells in solution, in samples obtained from subjects, and/or samples in a subject (in vivo sample). As used herein, a subject is a human, non-human primate, cow, horse, pig, sheep, goat, dog, cat, or rodent. In all embodiments, human subjects are preferred. The samples used herein are any cell or tissue sample, and may include neuronal cell and/or tissue samples.

Particularly important subjects to which the present invention can be applied are subjects with HD. The term "subject with HD" as used herein, means an individual who, at the time the sample is taken, has been diagnosed as having HD. Methods and antibodies of the invention may also be used to detect abnormal levels of Htt polypeptide acetylation in subjects that are not yet diagnosed with HD. The onset, progression, and/or regression of HD may also be monitored using methods and antibodies of the invention.

Antibodies and/or antigen-binding fragments thereof of the present invention can be used to screen patients for diseases associated with the presence of reduced levels of acetylated Htt polypeptide (e.g., HD). As used herein, the term "reduced" means lower, for example reduced versus a control level. Antibodies and antigen-binding fragments thereof of the invention may be used to identify the status and/or stage of HD by assessing the level of acetylated Htt in a sample from a subject or culture that has HD. Antibodies of the invention are particularly useful in assays to differentiate whether or not a subject has a HD, because there is a reduced level of acetylated mutant Htt protein in subjects with HD and anti-acetylated Htt antibodies of the invention can be used to quantitate the amount of acetylated Htt polypeptide in cells and tissues of subjects who have HD, or who are at risk of having HD. The percent of acetylated Htt polypeptide in a sample can be used to determine the presence and/or status of HD in a cell, cell culture or subject. Antibodies of the invention can be used to obtain useful prognostic information by providing an early indicator of disease onset and/or progression.

Levels of acetylated Htt polypeptide (e.g., K444-acetylated Htt polypeptide) can be determined in a number of ways when carrying out the various methods of the invention. In one particularly important measurement, a level of acetylated Htt polypeptide is measured in relation to non-acetylated Htt polypeptide. Thus, the measurement may be a relative measure, which can be expressed, for example, as a percentage of total Htt polypeptide. Those of ordinary skill in the art will appreciate that relative amounts of acetylated and non-acetylated Htt polypeptides may be determined by measuring either the relative amount of acetylated Htt polypeptide or the relative amount of non-acetylated Htt polypeptide. In other words, if 90% of an individual's Htt polypeptide is non-acetylated Htt polypeptide (or reduced acetylated Htt polypeptide), then 10% of the individual's Htt polypeptide will be acetylated Htt polypeptide. Thus, measuring the level of acetylated Htt polypeptide may be carried out using an antibody or antigen-binding fragment thereof of the invention in methods to measure the relative amount of non-acetylated Htt polypeptide.

Another measurement of the level of acetylated Htt is a measurement of absolute levels of Htt polypeptide acetylation. This could be expressed, for example, in acetylated Htt polypeptide per unit of cells or tissue. Another measurement of the level of acetylated Htt polypeptide is a measurement of the change in the level of acetylated Htt polypeptide over time. This may be expressed in an absolute amount or may be expressed in terms of a percentage increase or decrease over time. Antibodies or antigen-binding fragments of the invention may be used in diagnostic methods alone or in conjunction with certain antibodies already known in the art. Known antibodies may include anti-Htt antibodies as well as anti-acetylation-moiety antibodies, which bind to acetylated polypeptides.

Antibodies and/or antigen-binding fragments thereof of the invention are useful to characterize Htt polypeptide acetylation levels by monitoring changes in the absolute or relative amounts of acetylated Htt polypeptide in a subject or sample (e.g., a cell culture) over time. For example, it is expected that a decrease in acetylation of mutant Htt polypeptide correlates with increasing build up of mutant Htt polypeptides in cells and/or tissues. Accordingly one can monitor levels of acetylation of mutant Htt polypeptide over time to determine if mutant Htt polypeptide clearance levels of a subject or in a culture are changing. Changes in relative or absolute acetylated Htt polypeptide of greater than 0.1% may indicate an abnormality. Preferably, the change in acetylated Htt polypeptide levels that indicates an abnormality, is greater than 0.2%, greater than 0.5%, greater than 1.0%, 2.0%, 3.0%, 4.0%, 5.0%, 7.0%, 10%, 15%, 20%, 25%, 30%, 40%, 50%, or more. Increases in amounts of acetylated Htt over time may indicate a change in HD status in a sample or subject.

Importantly, levels of acetylated Htt polypeptide can be determined using the antibodies or antigen-binding fragments thereof of the invention and are advantageously compared to controls according to the invention. The control may be a predetermined value, which can take a variety of forms. It can be a single cut-off value, such as a median or mean. It can be established based upon comparative groups, such as in groups having normal amounts of Htt acetylation and groups having abnormal amounts of Htt acetylation. Another example of comparative groups may be groups having HD or HD symptoms and groups without HD or HD symptoms. Another comparative group may be a group with a family history of HD and a group without such a family history. A predetermined value can be arranged, for example, where a tested population is divided equally (or unequally) into groups, such as a low-risk group, a medium-risk group and a high-risk group or into quadrants or quintiles, the lowest quadrant or quintile being individuals with the lowest risk and highest amounts of acetylated Htt polypeptide and the highest quadrant or quintile being individuals with the highest risk and lowest amounts of acetylated Htt polypeptide.

The predetermined value, of course, will depend upon the particular population selected. For example, an apparently healthy population will have a different 'normal' range than will a population that is known to have a condition related to abnormal Htt polypeptide acetylated. Accordingly, the predetermined value selected may take into account the category in which an individual or cell falls. Appropriate ranges and categories can be selected with no more than routine experimentation by those of ordinary skill in the art. As used herein, "abnormal" means not normal as compared to a control. By abnormally high it is meant high relative to a selected control. Typically the control will be based on apparently healthy normal individuals in an appropriate age bracket or apparently healthy cells.

It will also be understood that controls according to the invention may be, in addition to predetermined values, samples of materials tested in parallel with the experimental materials. Examples include samples from control populations or control samples generated through manufacture to be tested in parallel with the experimental samples.

Antibodies or antigen-binding fragments thereof of the invention may also be used in diagnostic methods to determine the effectiveness of treatments for HD. "Evaluation of treatment" as used herein, means the comparison of a subject's levels of acetylated Htt measured in samples obtained from the subject at different sample times, preferably at least one day apart. In some embodiments, the time to obtain the second sample from the subject is at least 5, 10, 20, 30, 40, 50, minutes after obtaining the first sample from the subject. In certain embodiments, the time to obtain the second sample from the subject is at least 1, 2, 3, 4, 5, 6, 7, 8, 9, 10, 11, 12, 13, 14, 15, 16, 17, 18, 19, 20, 21, 22, 23, 24, 36, 48, 72, 96, 120 or more hours after obtaining the first sample from the subject.

Antibodies or antigen-binding fragments thereof of the invention may be used to allow the comparison of levels of acetylated Htt in two or more samples, taken at different times, which is a measure of level of a subject's clearance of mutant Htt polypeptide and allows evaluation of a treatment of HD. The comparison of a subject's levels of acetylated Htt measured in samples obtained at different times and/or on different days provides a measure mutant Htt clearance to determine the effectiveness of any treatment for HD (or to regulate mutant Htt clearance) in a subject. Those of ordinary skill in the art will recognize that similar assessments of candidate therapeutics can be tested in vitro by assessing any change in Htt acetylation that occurs in response to contact of the cell with a candidate agent for treatment of HD.

As will be appreciated by those of ordinary skill in the art, the evaluation of a treatment also may be based upon an evaluation of symptoms or clinical end-points of HD in a subject. Thus, antibodies or antigen-binding fragments thereof of the invention may be useful for determining the onset, progression or regression of a condition that is characterized by the build up of mutant Htt polypeptides. In some instances, antibodies or antigen-binding fragments thereof of the invention can be used to detect Htt polypeptide acetylation and clearance of Htt polypeptides in subjects already diagnosed as having HD. In other instances, antibodies or antigen-binding fragments thereof of the invention can be used to obtain measurements that represent the diagnosis of HD in a subject. In some instances, a subject may be already be undergoing drug therapy for HD, while in other instances a subject may be without present HD therapy.

In this aspect of the invention, the treatments are based upon selecting subjects who have abnormally low levels of acetylated Htt polypeptide (e.g., reduced levels of acetylated mutant Htt polypeptide) and the treatment may include administration of one or more acetylated Htt polypeptides of the invention. Such subjects may already be receiving a drug for treating HD. It may be appropriate according to the invention to alter a therapeutic regimen for a subject, based upon the measurement of the level of acetylated Htt polypeptide using an antibody or antigen-binding fragment thereof of the invention. This can be understood in connection with treatment of HD. A subject may be free of any present treatment for HD but monitoring of Htt polypeptide acetylation levels using methods and/or antibodies of the invention, may identify the subject as a candidate for a treatment to increase acetylation of Htt and/or treatment to decrease deacetylation of Htt polypeptide. Thus, subjects may be selected and treated with elevated levels of the same drugs or with different therapies as a result of assays that utilize the antibodies or antigen-binding fragments thereof of the invention.

According to the present invention, some subjects may be free of symptoms otherwise calling for treatment with a particular therapy, and testing with an anti-Htt polypeptide-acetylation antibody of the invention may identify the subject as needing treatment. This means that absent the use of the antibodies or antigen-binding fragments thereof of the invention to assess levels of acetylated Htt polypeptide, the subject would not according to convention as of the date of the filing of the present application have symptoms calling for treatment with a particular therapy. As a result of measuring the level of acetylated Htt polypeptide that the subject that a subject has, the subject become a candidate for treatment with the therapy.

According to still another aspect of the invention, compounds that increase the amount of acetylation of Htt polypeptide (e.g., mutant Htt polypeptide) may be administered to prevent and/or treat Htt. Compounds useful to increase acetylation levels of Htt polypeptide and may be administered as a treatment for HD include, but are not limited to HDAC inhibitors, or analogs thereof. In some embodiments, a treatment for HD may comprise administration of an HDAC1 inhibitor, or analog thereof.

Additional treatments for HD may include administration of acetylated Htt polypeptide or acetylated fragments thereof to a subject to prevent and/or treat HD. Such treatment methods of the invention may include selecting and administering to a subject who is known to have HD, an effective amount of a therapeutic composition that includes an acetylated Htt polypeptide or an acetylated fragment thereof. Administration of acetylated Htt polypeptide or an acetylated fragment thereof may result in the administered acetylated polypeptide acting as a decoy to reduce the deacetylation of mutant Htt polypeptide, thus enhancing the clearance of mutant Htt polypeptide from the subject. In some embodiments, an administered acetylated Htt polypeptide or acetylated fragment thereof comprises an acetylated residue that corresponds to K444 of full-length, wild-type Htt polypeptide and is administered in an amount effective to increase acetylated Htt polypeptide levels and to increase clearance of mutant Htt polypeptide.

In a subject determined to have an abnormally low level of acetylation of Htt polypeptide, an effective amount of an acetylated Htt polypeptide or other treatment (e.g., a compound that increases the level of acetylation of Htt polypeptide) is that amount effective to increase the level of acetylation of mutant Htt in the subject or decrease the amount of deacetylation in the subject—each of which will increase the level of acetylated Htt polypeptide to a level than was present prior to treatment. Thus, compounds that increase acetylation levels of Htt polypeptides (e.g., HDAC inhibitors such as, but not limited to HDAC1 inhibitors or analogs thereof) may be administered in effective amounts to prevent and/or treat HD. Also, acetylated Htt polypeptides of the invention may be administered in effective amounts to prevent and/or treat HD. Typically an effective amount of a compound that increases a level of acetylated Htt (e.g., an HDAC inhibitor, such as HDAC1 inhibitors) or an effective amount of an acetylated Htt polypeptide fragment will be determined in clinical trials, establishing an effective dose for a test population versus a control population in a blind study. In some embodiments, an effective amount will be an amount that results in a desired response, e.g., an amount that diminishes or eliminates accumulation of mutant Htt polypeptide in neuronal cells and/or tissues in a subject with HD. Thus, an effective amount may be the amount that when administered reduces the amount of mutant Htt polypeptide accumulation from the amount that would occur in the subject or tissue without the administration of the acetylated Htt polypeptide of the invention. In the case of treating a particular disease or condition the desired response is inhibiting the progression of the disease or condition. This may involve only slowing the progression of the disease temporarily, although more preferably, it involves halting the progression of the disease permanently. This can be monitored by routine diagnostic methods known to one of ordinary skill in the art for any particular disease. The desired response to treatment of the disease or condition also can be delaying the onset or even preventing the onset of the disease or condition.

Effective amounts of therapeutic compounds such as an HDAC inhibitor or HDAC1 inhibitor, or an effective amount of an acetylated Htt polypeptide composition (each of which may be referred to herein as pharmaceutical or therapeutic compounds) may also be determined by assessing physiological effects of administration on a cell or subject, such as a decrease of disease symptoms following administration. Other assays will be known to one of ordinary skill in the art and can be employed for measuring the level of the response to a treatment. The amount of a treatment may be varied for example by increasing or decreasing the amount of a therapeutic composition, by changing the therapeutic composition administered, by changing the route of administration, by changing the dosage timing and so on. The effective amount will vary with the particular condition being treated, the age and physical condition of the subject being treated, the severity of the condition, the duration of the treatment, the nature of the concurrent therapy (if any), the specific route of administration, and the like factors within the knowledge and expertise of the health practitioner. For example, an effective amount may depend upon the degree to which an individual has abnormally low levels of acetylation of Htt polypeptide.

Effective amounts will also depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of an acetylated Htt polypeptide composition (alone or in combination with other therapeutic agents) be used, that is, the highest safe dose according to sound medical judgment. It will be understood by those of ordinary skill in the art, however, that a patient may insist upon a lower dose or tolerable dose for medical reasons, psychological reasons or for virtually any other reasons.

A pharmaceutical compound dosage may be adjusted by the individual physician or veterinarian, particularly in the event of any complication. A therapeutically effective amount typically varies from 0.01 mg/kg to about 1000 mg/kg, preferably from about 0.1 mg/kg to about 200 mg/kg, and most preferably from about 0.2 mg/kg to about 20 mg/kg, in one or more dose administrations daily, for one or more days.

The absolute amount will depend upon a variety of factors, including the material selected for administration, whether the administration is in single or multiple doses, and individual subject parameters including age, physical condition, size, weight, and the stage of the disease or condition. These factors are well known to those of ordinary skill in the art and can be addressed with no more than routine experimentation.

Pharmaceutical compounds of the invention may be administered alone, in combination with each other, and/or in combination with other drug therapies, or other treatment regimens that are administered to subjects with HD.

A pharmaceutical compositions used in the foregoing methods preferably are sterile and contain an effective amount of a therapeutic compound that will increase the level of acetylation of mutant Htt polypeptide for a level that produces the desired response in a unit of weight or volume suitable for administration to a patient.

The doses of acetylated Htt polypeptide, or other pharmaceutical compound of the invention administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

Various modes of administration will be known to one of ordinary skill in the art which effectively deliver an acetylated Htt polypeptide, or other pharmaceutical compound of the invention (e.g., an HDAC1 inhibitor) to a desired tissue, cell or bodily fluid. Methods for administering an acetylated Htt polypeptide, or other pharmaceutical compound of the invention may be topical, intravenous, oral, intracavity, intrathecal, intrasynovial, buccal, sublingual, intranasal, transdermal, intravitreal, subcutaneous, intramuscular and intradermal administration. The invention is not limited by the particular modes of administration disclosed herein. Standard references in the art (e.g., *Remington 's Pharmaceutical Sciences,* 18th edition, 1990) provide modes of administration and formulations for delivery of various pharmaceutical preparations and formulations in pharmaceutical carriers. Other protocols which are useful for the administration of an acetylated Htt polypeptide, or other therapeutic compound of the invention will be known to one of ordinary skill in the art, in which the dose amount, schedule of administration, sites of administration, mode of administration (e.g., intra-organ) and the like vary from those presented herein.

Administration of an acetylated Htt polypeptide, or other pharmaceutical compound of the invention to mammals other than humans, e.g., for testing purposes or veterinary therapeutic purposes, is carried out under substantially the same conditions as described above. It will be understood by one of ordinary skill in the art that this invention is applicable to both human and animal diseases which can be treated by an acetylated Htt polypeptide, or other pharmaceutical compound of the invention.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. Preferred components of the composition are described above in conjunction with the description of the acetylated Htt polypeptides of the invention.

An acetylated Htt polypeptide, or other therapeutic compound of the invention may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the acetylated Htt polypeptide, or other therapeutic compound of the invention, and with each other, in a manner such that there is no interaction which would substantially impair the desired pharmaceutical efficacy.

A pharmaceutical composition of the invention may contain suitable buffering agents, as described above, including: acetate, phosphate, citrate, glycine, borate, carbonate, bicarbonate, hydroxide (and other bases) and pharmaceutically acceptable salts of the foregoing compounds.

A pharmaceutical composition of the invention, also may contain, optionally, suitable preservatives, such as: benzalkonium chloride; chlorobutanol; parabens and thimerosal. The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration may comprise an acetylated Htt polypeptide, or other therapeutic compound of the invention. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in *Remington 's Pharmaceutical Sciences*, Mack Publishing Co., Easton, Pa.

Also within the scope of the invention are kits comprising the compositions of the invention and instructions for use. The kits can further contain at least one additional reagent, such as one or more additional antibodies of the invention (e.g., an antibody having a complementary activity which binds to an epitope in an acetylated or non-acetylated Htt polypeptide distinct from the first antibody).

Kits containing antibodies or antigen-binding fragments thereof of the invention can be prepared for in vitro diagnosis, prognosis and/or monitoring HD by the immunohistological, immunocytological and immunoserological methods described above. The components of the kits can be packaged either in aqueous medium or in lyophilized form. When the antibodies or antigen-binding fragments thereof are used in the kits in the form of conjugates in which a label moiety is attached, such as an enzyme or a radioactive metal ion, the components of such conjugates can be supplied either in fully conjugated form, in the form of intermediates or as separate moieties to be conjugated by the user or the kit. In some embodiments of a kit of the invention, an antibody or antigen-binding fragment thereof may be attached to a substrate, for example a dipstick, card, slide, plate, dish, tube, vial, etc.

A kit may comprise a carrier being compartmentalized to receive in close confinement therein one or more container means or series of container means such as test tubes, vials, flasks, bottles, syringes, or the like. A first of said container means or series of container means may contain one or more anti-acetylated Htt antibodies or antigen-binding fragments thereof or an acetylated Htt polypeptide. A second container means or series of container means may contain a label or linker-label intermediate capable of binding to the primary anti-acetylated Htt antibodies (or fragment thereof).

A kit of the invention may also include instructions. Instructions typically will be in written form and will provide guidance for carrying-out the assay embodied by the kit and for making a determination based upon that assay.

Acetylated Htt polypeptides, and antibodies and antigen-binding fragments of the invention may also be useful in methods of screening for candidate agents that modulate levels of acetylation of Htt polypeptide. Methods can include mixing the candidate agent with cells or tissues or in a subject and using the antibodies of the invention to determine the level of acetylated Htt before and after contact with the candidate agent. An increase in the amount of acetylated Htt in comparison to a control is indicative of that the candidate agent/compound is capable of increasing the level of acetylated Htt and the clearance of mutant Htt from cells, tissues, and/or subjects.

The assay mixture comprises a candidate agent. The candidate agent is preferably an antibody, a small organic compound, or a polypeptide, and accordingly can be selected from combinatorial antibody libraries, combinatorial protein libraries, or small organic molecule libraries. Typically, pluralities of reaction mixtures are run in parallel with different agent concentrations to obtain a different response to the various concentrations. Typically, one of these concentrations serves as a negative control, i.e., at zero concentration of agent or at a concentration of agent below the limits of assay detection.

Candidate agents encompass numerous chemical classes, although typically they are organic compounds, proteins or antibodies (and fragments thereof that bind antigen). In some preferred embodiments, the candidate agents are small organic compounds, i.e., those having a molecular weight of more than 50 yet less than about 2500, preferably less than about 1000 and, more preferably, less than about 500. Candidate agents comprise functional chemical groups necessary for structural interactions with polypeptides and/or nucleic acids, and typically include at least an amine, carbonyl, hydroxyl, or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as polypeptides, saccharides, fatty acids, sterols, isoprenoids, purines, pyrimidines, derivatives or structural analogs of the above, or combinations thereof and the like.

Candidate agents or compounds may include HDAC inhibitors, including, but not limited to HDAC1 inhibitors.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random or non-random polypeptides, combinatorial libraries of proteins or antibodies, and the like. Alternatively, libraries of natural compounds in the form of bacterial, fungal, plant, and animal extracts are available or readily produced. Additionally, natural and synthetically produced libraries and compounds can be readily be modified through conventional chemical, physical, and biochemical means. Further, known agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc., which may be used to facilitate optimal protein-protein and/or protein-agent binding. Such a reagent may also reduce non-specific or background interactions of the reaction components. Other reagents that improve the efficiency of the assay such as protease inhibitors, nuclease inhibitors, antimicrobial agents, and the like may also be used.

The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours. After incubation, the presence or absence of and/or the level of acetylated Htt is detected by any convenient method available to the user. For example, the level of acetylated Htt can be determined through the measure of a detectable label using standard methods and as described herein.

EXAMPLES

Example 1

Introduction

Huntington's disease (HD) is one of at least nine autosomal dominant neurodegenerative diseases caused by the expansion of a glutamine repeat in disease proteins (1). Despite major advances in our understanding of polyglutamine pathogenesis no cure is available for these devastating disorders. Numerous studies in cell culture and animal models of HD have implicated histone acetyltransferase (HAT) and inhibitors of histone deacetylase (HDAC) as neuroprotective in HD, but the mechanism of protection remains unknown (2-7). Here it is shown that mutant huntingtin protein (Htt) itself is acetylated at lysine residue 444 (K444) by CREB-binding protein (CBP). Importantly, increased acetylation at K444 facilitates autophagic clearance of mutant Htt and protects cultured neurons from Htt-mediated toxicity. In HD mouse brains, mutant but not the wild-type Htt is acetylated. Treatment of HD knock-in mice with HDAC inhibitors results in decreased levels of mutant Htt. These findings suggest that increased acetylation and subsequent clearance of mutant Htt represent a promising novel target for development of neuroprotective therapies in HD. Lysine 444 in Htt polypeptide is a conserved residue. Full-length Htt polypeptide sequence alignment (FIG. 5) reveals conservation of K444 (arrowhead) in human (SEQ ID NO:4), mouse (SEQ ID NO:5), rat (SEQ ID NO:6), zebrafish (SEQ ID NO:7) and pufferfish (SEQ ID NO:8).

Methods

Plasmid Constructs, Mutagenesis and Antibodies. Htt480-17Q and Htt480-68Q plasmids were generated by placing Htt480-17Q and Htt480-68Q cDNA (14) into pcDNA3.1(+). Sequencing analysis revealed that DNA encoding 11 amino acids (KLLEAAARACI; SEQ ID NO:54) was inserted at the 3' end of Htt480 cDNAs. The K of the inserted sequence was mutated to a Stop codon using QuikChange site-directed mutagenesis kit (Stratagene, La Jolla, Calif.). Htt590-97Q insert was generated by PCR amplification of full-length human-mouse hybrid Htt cDNA with 75Q (27) and subcloned into pcDNA3.1(−)/myc-His vector. A stop codon was introduced at the 3' end after amino acid 574 of mouse Htt and the CAG repeat sequence was replaced with a sequence containing a mixture of CAG and CAA codons encoding 97 glutamines. The resulting Htt590-97Q protein contained 59 residues of human Htt, 514 residues of mouse Htt and 97 glutamines. RFP-Htt480-68Q was generated by digesting Htt480-68Q and Htt480-68Q-KR with ApaI and EcoRI and subcloning of Htt-fragment into mRFP1 vector (28). All KR plasmids were generated by mutating lysine 444 to arginine. GFP-LC3 was a kind gift from Dr. Yoshimori (18). Full-length CBP and CBPΔQ were described previously (22). CBP-HAT construct was generated by placing PCR-amplified insert (aa1069-1802) of human CBP cDNA in frame with HA tag of pGW1-HA vector. CBP-HAT-DY was generated by mutating aspartic acid at 1435 to tyrosine (9).

Antibodies used were anti-Htt (MAB2166, MAB5490, and MAB5492, Chemicon (Millipore, Biollerica, Mass.), anti-beta-tubulin (TUB2.1, Sigma-Aldrich, St Louis, Mo.), anti-HA (Y-11, Santa Cruz Biotechnology, Santa Cruz, Calif., and HA.11, Covance, Princeton, N.J.), anti-Flag (M2, Sigma-Aldrich) and anti-LC3 (APG8b, Abgent, San Diego, Calif.).

Cell Culture and Transfection. Neuro2a, STHdh$^{Q7/Q7}$, and COS-7 cells were transfected using Lipofectamine 2000. For HDAC inhibition, TSA (1 μM) and NAM (5 mM) were applied 6 hrs and 16 hrs, respectively, prior to harvest. Unless indicated otherwise, cells were harvested 24 hrs after transfection. For the experiments with proteasome and autophagy inhibitors, Neuro2a cells were treated with lactacystin (10 μM) or 3-methyladenine (10 mM) for 12 hrs. For assessment of LC3 conversion, immortalized striatal cells (STHdh$^{Q7/Q7}$) were cultured as described (29), transfected for 48 hrs and treated with TSA (4 μM) and NAM (5 mM) 15 hrs prior to harvest.

Mass Spectrometry. Htt480-68Q was immunoprecipitated with Htt antibody (MAB5492) from transfected COS-7 cells treated with TSA (1 μM) and NAM (5 mM). Protein bands were Coomassie-stained, digested with trypsin and analyzed by mass spectrometry (LC-MS/MS). In order to detect acetylated lysine residues, MS/MS data were searched against the Htt480-68Q-Myc sequence using the SEQUEST algorithm. Mass spectrometry and sequence analysis were performed at Taplin Biological Mass Spectrometry Facility (Boston, Mass.) (Thermo Electron 7-T LTQ FT), Partners HealthCare Center for Genetics and Genomics Proteomic Facility (Cambridge, Mass.) (ThermoFinnigan DECA LCQ), and at the LNT/NIMH/NH (Finnigan LCQ Classic).

Generation and Characterization of Htt Acetyl-K444 Specific Antibody. The K444-acetylated polypeptide of Htt, CRKQKGK$_{Ac}$VLLG (SEQ ID NO: 13) (Polypeptide Synthesis Facility, Tufts University, Boston, Mass.) was used to immunize three rabbits (Covance). Serum collected after four injections was passed over unacetylated polypeptide-conjugated Sepharose (Pierce Chemical, Rockford, Ill.) and the flowthrough was passed over acetylated polypeptide-conjugated Sepharose. The acetylated polypeptide-specific antibody was eluted with 0.1M glycine, pH 2.3. The specificity of AcK444 was assessed using a dot blot assay where serial dilutions of K444-acetylated polypeptide and unacetylated polypeptide, ranging from 300 ng to 2.3 ng, were spotted on a nitrocellulose membrane and western blot analysis performed with purified AcK444 antibody.

Primary neuron culture and neuronal toxicity assay. Rat primary cortical and striatal neurons were isolated from Sprague-Dawley rats at embryonic day 19. Primary neurons were transfected using Lipofectamine 2000 on DIV 8. Neurons were fixed and double-stained with anti-Htt (MAB5492) and anti-HA (Y-11) antibodies 18 hrs after transfection. Cell death was monitored as described previously (30). At least 150 transfected cells were scored per experiment.

Determination of Htt polypeptide turnover. Neuro2a cells were transfected and treated with 5 μg/ml of cycloheximide (CHX). Cell extracts were prepared at 0, 8, 16, and 24 hrs after the CHX treatment and Htt polypeptide levels determined by western blots. For quantification, densitometric analysis was done using NIH ImageJ software.

Live-cell Imaging. COS-7 cells grown on 35 mm glass bottom culture dishes were transfected and analyzed on a Zeiss LSM 510 confocal microscope (Carl Zeiss, Jena, Germany) 24 hrs after transfection. Cells were kept at 37° C. and 5% $CO_2$ on the microscope stage and images were acquired sequentially in red and green channels using a 25× water objective.

Animal Experiments and HDAC inhibitor treatment. Brain homogenates from 12-week-old wild type, heterozygous and homozygous HD knock-in mice (19, 20) were immunoprecipitated using MAB 5490. Precipitated protein was resolved by SDS-PAGE and western blots probed with AcK444 followed by stripping and probing with MAB 5490. For HDAC inhibitor treatment, 20 heterozygous knock-in mice (Hdh$^{Q7/}$$_{Q140}$; age 12 weeks) were treated with vehicle, or TSA (2.5 μg/kg/day i.p.) and NAM (1 g/kg/day i.p.) daily for 10 days.

Brains were homogenized and 50 μg of total protein resolved by SDS-PAGE using special low-BIS gels (21) to assure appropriate resolution of wild type and mutant Htt and faithful quantification of Htt polypeptide band intensities.

Statistical analyses. The two-tailed Student's t-test was used to compare the means of two samples. Results are shown as means±SEM.

Specificity of the Anti-Acetylated Htt Polypeptide Antibody

The specificity of the rabbit polyclonal antibody against acetyl-K444 Htt polypeptide (AcK444) was determined by dot blot assay. FIG. 6 shows results of the experiment in which a nitrocellulose membrane was spotted with different amounts of acetyl-K444 polypeptide or unmodified polypeptide and probed with AcK444 antibody.

Subcloning of the CBP-HAT Domain and Generation of a HAT-Deficient CBP Construct The CBP-HAT domain was subcloned and a HAT-deficient CBP construct was generated. FIG. 7 shows results indicating that truncated CBP encompassing the HAT domain (CBP-HAT, aa1096-1802) was subcloned into mammalian HA-tagged expression vector (pGWI-HA). The corresponding HAT-deficient construct was generated by mutating aspartic acid residue 1435 to tyrosine (Y), analogous to the D1399Y mutation that abolishes HAT activity of p300. The polypeptide alignment depicts the highly conserved region of the CBP and p300 HAT domains with the critical aspartic acid residue marked by an arrowhead. The sequence RRVYISYLDSIHFFRPRC is SEQ ID NO:9 and RRVYISYLDSVHFFRPKC is SEQ ID NO:10.

Results/Discussion

To further characterize the acetylation of Htt polypeptide at K444, specific antibody against acetylated K444 was generated and affinity purified (hereafter referred to as AcK444). The specificity of AcK444 antibody was determined using a dot blot assay where a nitrocellulose membrane was spotted with serial dilutions of K444 acetyl polypeptide (CRKQKGK$_{Ac}$VLLG, SEQ ID NO: 13) and native polypeptide (CRKQKGKVLLG, SEQ ID NO:53) and probed with purified AcK444. These experiments demonstrated that the antibody reacted to K444-acetylated polypeptide, but not to the native polypeptide (FIG. 6). To further assess the specificity of the antibody, lysine 444 was mutated to arginine (R) in an expression vector encoding the N-terminal 590 amino acids of Htt with 97 glutamines (Htt590-97Q), generating Htt590-97Q-KR mutant construct. When overexpressed in COS-7 cells in the presence of HDAC inhibitors, Htt590-97Q was detected by the AcK444 antibody, but the K444R mutation completely abrogated reactivity of AcK444 to Htt, demonstrating specificity of AcK444 antibody for acetylated K444 (FIG. 1B).

Using AcK444 antibody to monitor acetylation status of Htt polypeptides, experiments were performed to examine the effects of HDAC inhibitors on acetylation of wild-type Htt with 17 glutamine repeats (Htt480-17Q) and mutant Htt polypeptide with 68 repeats (Htt480-68Q). As shown in FIG. 1C, treatment with TSA and NAM augmented the acetylation of both wild-type and mutant Htt polypeptides. Interestingly, mutant Htt displayed higher levels of acetylation compared to wild-type Htt polypeptide, both at basal level and after treatment with HDAC inhibitors.

Next, experiments were performed to identify the histone acetyltransferase (HAT) responsible for acetylation of Htt at K444. A number of known HATs were examined by co-transfection of HAT together with mutant Htt (Htt480-68Q). Although p300, P/CAF, Tip60, HAT1 or HBO1 did not alter Htt acetylation, CBP strongly increased the acetylation of mutant Htt above basal level (FIG. 1D). Expression of all HAT constructs was confirmed by western blotting. Previous studies found that Htt interacts with CBP through the acetyltransferase domain whereas glutamine-rich domain of CBP was not required for the interaction. (7) In support of this observation, it was demonstrated that deletion of glutamine-rich domain in CBP (CBPΔQ) did not alter the ability of CBP to acetylate mutant Htt (FIG. 1D). In addition to its HAT and glutamine-rich domains, CBP contains other functional domains including cysteine-histidine-rich domains, bromodomain, and CREB-binding domain (8). To examine the requirement of HAT activity for Htt acetylation separately from other CBP-mediated activities, CBP HAT domain was subcloned into a mammalian expression vector (FIG. 7). As shown in FIG. 1E, CBP-HAT construct potently induced acetylation of Htt. Next, a mutant construct was made that had inactivated CBP-HAT activity analogous to a published p300 HAT-deficient mutant where aspartic acid (D) at residue 1399 was mutated to tyrosine (Y) (9). By aligning the corresponding regions of p300 and CBP, a conserved aspartic acid was identified in CBP (aa 1435) and a D1435Y mutant of CBP-HAT was generated by site-directed mutagenesis (FIG. 7). As shown in FIG. 1E, the DY mutation completely abolished the ability of CBP-HAT to acetylate Htt polypeptide at K444, further demonstrating the requirement of functional HAT domain in CBP for acetylation of Htt polypeptide.

Having found that CBP acetylated mutant Htt, experiments were performed to examiner whether Htt polypeptide could be deacetylated by histone deacetylases (HDACs). Neuro2a cells were transfected with Htt480-68Q and CBP-HAT to increase Htt polypeptide acetylation level. A series of HDACs was cotransfected, and western blot analysis revealed that only HDAC1 reduced Htt polypeptide acetylation, whereas HDACs 2, 3, 4, 5 and 6 had no effect (FIG. 1F). Expression of HDACs was confirmed by immunoblotting. Taken together, these findings suggest that acetylation and deacetylation of Htt polypeptide is mediated by a specific subset of HATs and HDACs.

Figures 2A, 2B, 2C, 2D, 2E, 2F:
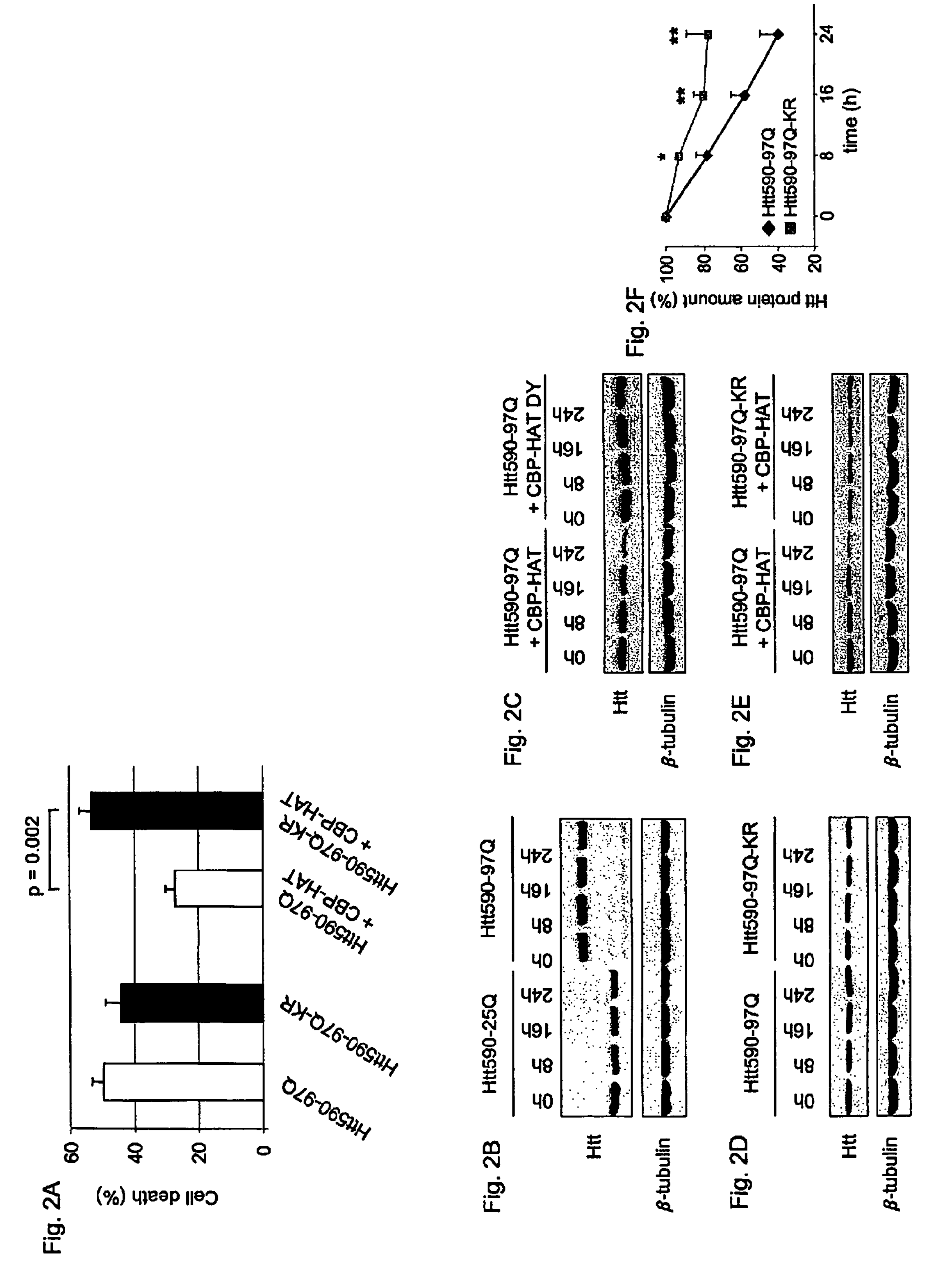
FIG. 2A shows that transfection of primary rat cortical neurons with Htt590-97Q or Htt590-97Q-KR led to more than 40% neuronal toxicity. While co-expression of CBP-HAT resulted in significant protection from Htt590-97Q mediated toxicity, mutation of K444 completely abolished the protective effects of CBP-HAT. At least 150 neurons per sample were scored. Results of three independent experiments are expressed as means+SEM (p=0.002).
FIGS. 2B-E show results of experiments to monitor Htt polypeptide turnover, Neuro2a cells were transfected with Htt constructs, treated with cycloheximide and harvested at the indicated time points. Htt polypeptide levels were determined by western blotting, and β-tubulin was used as loading control.
FIG. 2F shows results of quantitative analysis of FIG. 2E. Western blots were analyzed by densitometry and values normalized to the amount of Htt polypeptide at the time of cycloheximide treatment (100%). Mutation of lysine 444 (Htt 590-97Q-KR) significantly slowed clearance of mutant Htt polypeptide (Htt590-97Q). Values represent means of 4 independent experiments+SEM, * $p<0.05$; ** $p<0.01$ compared to native Htt polypeptide.

To elucidate the role of Htt polypeptide acetylation in HD pathogenesis, it was first investigated whether this modification modulates mutant Htt polypeptide toxicity. Previous studies in cell culture and animal models of HD demonstrated that depletion of CBP enhanced toxicity whereas overexpression of CBP suppressed toxicity by mutant Htt polypeptide (2, 6, 10). Here it was examined whether the protective effects of CBP may be related to acetylation of mutant Htt polypeptide. Rat primary cortical neurons were cotransfected with mutant Htt (Htt590-97Q) and CBP-HAT and toxicity monitored by scoring pyknotic or fragmented nuclei. Expression levels of mutant Htt polypeptide and HA-tagged CBP-HAT were determined by double staining with anti-Htt and anti-HA antibodies. When transfected along with Htt590-97Q, CBP-HAT significantly protected neurons from Htt polypeptide-induced toxicity (FIG. 2A). To examine whether the protective effect of CBP involved Htt polypeptide acetylation, acetylation-resistant mutant Htt590-97-KR was transfected together with CBP-HAT. Remarkably, neuronal toxicity mediated by Htt590-97-KR was not protected by CBP-HAT, suggesting that intact lysine at position 444 is required for the rescue by CBP (FIG. 2A). Results indicated protection of Htt polypeptide toxicity by CBP-HAT. Cortical neurons were transfected as described in FIG. 1 description and stained for Htt (MAB5492) and CBP-HAT (HA antibody). In the presence of K444, nuclei of CBP-HAT-expressing cells appeared normal (DAPI stain), whereas cells lacking CBP-HAT showed nuclear condensation. By contrast, expression of Htt590-97Q-KR led to nuclear condensation both in the presence and absence of CBP-HAT. Together, these findings suggest that acetylation of K444 by CBP contributes to protection of neurons from mutant Htt polypeptide toxicity.

In order to further elucidate the mechanism by which acetylation of Htt polypeptide leads to neuroprotection, whether the turnover of Htt polypeptide is modulated by acetylation was investigated. Toward this end, Neuro2A cells were transfected with mutant or wild-type Htt polypeptides and treated with protein synthesis inhibitor cycloheximide (CHX) followed by measurement of Htt polypeptide levels at fixed intervals after the treatment. Although the levels of wild-type Htt polypeptide (Htt590-25Q) progressively decreased, mutant Htt polypeptide (Htt590-97Q) remained stable over a period of 24 hours after CHX treatment (FIG. 2B). By contrast, cotransfection of CBP-HAT caused a decrease in the levels of mutant Htt polypeptide over time (FIG. 2C). To determine if the effect of CBP on Htt polypeptide stability was mediated by the HAT activity of CBP, HAT-deficient mutant CBP-HAT-DY was cotransfected in place of CBP-HAT. In sharp contrast to CBP-HAT, CBP-HAT-DY had no effect on mutant Htt polypeptide stability (FIG. 2C), suggesting that the reduction of Htt polypeptide levels required HAT activity of CBP. To further establish whether the effects of CBP on Htt polypeptide stability were mediated by acetylation of lysine 444, stability of Htt590-97Q was compared with that of acetylation-resistant Htt590-97Q-KR. At baseline, levels of both Htt590-97Q and Htt590-97Q-KR remained stable over a period of 24 hours (FIG. 2D), suggesting that KR mutation itself does not significantly affect Htt protein stability. By contrast, cotransfection of CBP-HAT led to progressively lower levels of Htt590-97Q, whereas the protein level of acetylation-resistant Htt590-97Q-KR remained comparatively unaltered (FIGS. 2E, 2F), strongly implicating acetylation at K444 as the cause of reduced stability of Htt polypeptide. Taken together, these results suggest that acetylation of Htt polypeptide at K444 facilitates clearance of mutant Htt polypeptide.

Figures 3A, 3B, 3C:
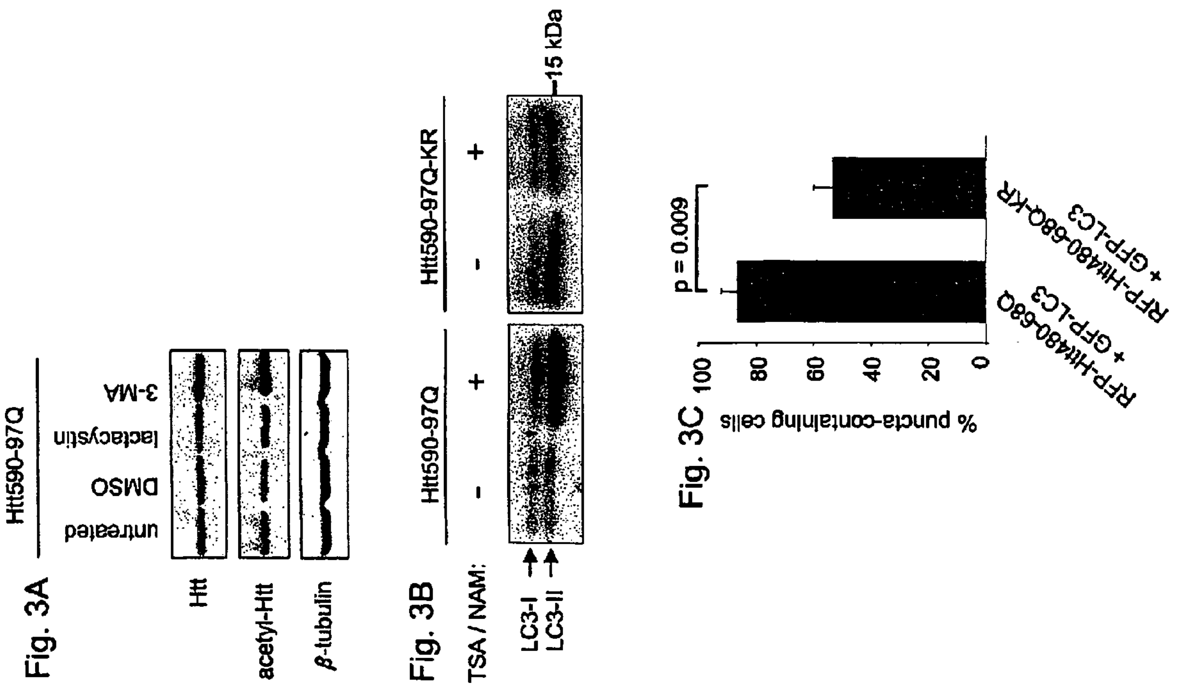
FIG. 3A shows that inhibition of autophagy leads to accumulation of acetyl-Htt polypeptide. Neuro2a cells were transfected with Htt590-97Q and treated with the proteasome inhibitor lactacystin or autophagy inhibitor 3-methyladenine (3-MA). Untreated and vehicle-treated cells served as controls. Western blot was performed to analyze levels of total Htt polypeptide and acetylated Htt polypeptide. Beta-tubulin was used as a loading control.
FIG. 3B shows that acetylation of mutant Htt leads to increased LC3-I to LC3-II conversion. Immortalized mouse striatal cells ($STHdh^{Q7/Q7}$) were transfected with the indicated Htt constructs, treated with TSA and NAM and analyzed by western blotting.
FIG. 3C shows quantitative analysis of LC3 accumulation.

Previous studies suggested that the clearance of mutant Htt polypeptide is mediated by both autophagy and ubiquitin-proteasome system (11-16). To examine which of these pathways may be responsible for clearance of acetylated Htt polypeptide, Neuro2a cells were transfected with Htt590-97Q and treated with inhibitors of proteasome or autophagy. Although the proteasome inhibitor lactacystin had no significant effect on either total Htt or acetyl-Htt level, treatment with macroautophagy inhibitor 3-methyladenine (3-MA) led to accumulation of both acetylated mutant Htt and to a lesser degree total mutant Htt (FIG. 3A), suggesting that macroautophagy plays a role in clearance of acetylated mutant Htt polypeptide. In order to further examine whether acetylated Htt polypeptide leads to activation of macroautophagy, LC3 conversion was assessed (17, 18). LC3, a mammalian homologue of yeast Atg8, is a diffusely distributed protein that upon activation by mammalian Atg7 undergoes posttranslational modification resulting in the product LC3-II, which firmly associates with the autophagosomal membrane. The amount of LC3-II, which migrates faster than LC3-I on SDS-PAGE, provides a reliable measure of autophagic activity (17). In order to assess autophagic activity in relation to Htt acetylation, immortalized striatal cells (STHdh$^{Q7/Q7}$) were transfected with Htt590-97Q or acetylation-resistant Htt590-97Q-KR, treated with TSA and NAM and analyzed by western blotting with anti-LC3 antibody (FIG. 3B). In cells transfected with Htt590-97Q, treatment with HDAC inhibitors led to a marked increase in LC3-II, indicative of activated autophagy. In contrast, cells that were transfected with Htt590-97Q-KR did not exhibit an increase of LC3-II in response to HDAC inhibitor treatment, suggesting that acetylation of Htt polypeptide at K444 was required for increased autophagic activity.

LC3, when fused to fluorescent proteins, can also be used to monitor autophagy in living cells, where activation of autophagy leads to increased appearance of LC3-positive puncta and vacuoles (17). Membrane was probed with anti-LC3 Ab to detect endogenous LC3-I and LC3-II. The results showed that acetylation of mutant Htt polypeptide at lysine 444 led to increased recruitment of LC3 to autophagic vacuoles. Htt480-68Q and Htt480-68Q-KR were fused to red fluorescent protein (RFP) and transfected into COS-7 cells together with GFP-LC3 and CBP-HAT. Living cells were sequentially scanned to detect distribution of Htt (red) and LC3 (green). The results showed that coexpression of RFP-Htt480-68Q with LC3 and CBP-HAT led to accumulation of LC3 puncta in transfected cells, indicative of active autophagy. Results showed that cells transfected with Htt RFP-Htt480-68Q-KR displayed a marked decrease in the incidence of LC3 puncta. Results of confocal microscopy demonstrated co-localization of mutant Htt polypeptide and LC3 as well as LC3-positive vacuoles that did not contain mutant Htt polypeptide. Quantitative analysis of LC3 accumulation was monitored (results shown in FIG. 3C). Cells containing >1 puncta were scored as puncta-containing cells. At least 150 cells were scored per sample, and values expressed as means+SEM of three independent experiments; p=0.009.

This approach was used to monitor the activation of autophagy in COS-7 cells transfected with GFP-tagged LC3 along with mutant Htt polypeptide and CBP-HAT. LC3-positive puncta were scored 24 hrs after transfection. 86% of cells containing mRFP-Htt480-68Q displayed more than one LC3-positive punctum or vacuole (mean=8) compared to 53% of cells expressing acetylation-resistant mRFP-Htt480-68Q-KR, most of which displayed only rare (mean=0.5) puncta or vacuoles. Mutant Htt polypeptide was found either colocalized with LC3, or LC3-positive vacuoles were observed with absent luminal Htt signal, possibly indicating clearance of mutant Htt engulfed by the LC3-positive autophagosome. These experiments in live cells further suggested that acetylation of mutant Htt polypeptide leads to increased autophagic activity and subsequent clearance of mutant Htt polypeptide.

Figures 4A, 4B, 4C, 4D:
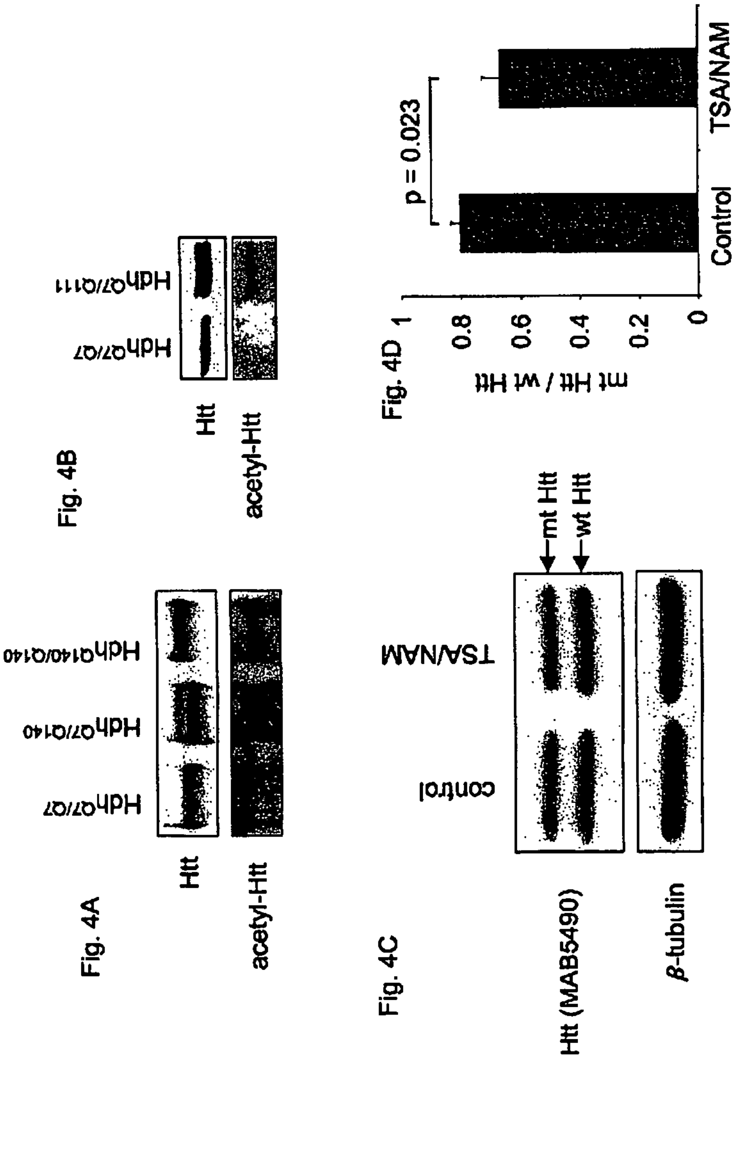
FIG. 4A shows brain samples of knock-in mice carrying an expanded polyglutamine stretch (140Q) in the HD homolog gene (Hdh) were analyzed. Comparison of wild type, ($Hdh^{Q7/Q7}$), heterozygous ($Hdh^{Q7/Q140}$) and homozygous ($Hdh^{Q140/Q140}$) animals revealed acetylated full-length Htt polypeptide only in animals that expressed mutant Htt polypeptide.
FIG. 4B shows results of lysates from a different knock-in mouse model (111Q) that were analyzed as in FIG. 4A. The comparison of wild-type ($Hdh^{Q7/Q7}$) and heterozygous ($Hdh^{Q7/Q111}$) littermates confirmed that only mutant Htt polypeptide is acetylated in vivo.
FIG. 4C shows that treatment with HDAC inhibitors decreases the amount of mutant Htt polypeptide relative to the wild type Htt polypeptide. Representative blot depicting results from a control animal and a TSA/NAM treated littermate. Heterozygous knock-in mice ($Hdh^{Q7/Q140}$) were injected with TSA and NAM or with vehicle only (control) for 10 days. Total brain homogenates were resolved by SDS-PAGE and membranes probed with Htt antibody (MAB 5490). Densitometry was performed to determine the ratio of mutant Htt polypeptide (mt Htt) over wild-type Htt polypeptide (wt Htt). Beta-tubulin was used as loading control.
FIG. 4D shows a total of 10 TSA/NAM treated mice and 10 control littermates that were used for analysis as in FIG. 4C. Densitometry revealed an average decrease of 13.1% of mt Htt polypeptide:wt Htt polypeptide ratio in TSA/NAM-treated animals. Results are shown as means of ratios+SEM; (p=0.023).

Taken together, our findings in cultured cells suggested that acetylation of mutant Htt polypeptide at K444 facilitated the clearance of mutant Htt polypeptide. In order to examine whether these observations may be confirmed in vivo, acetylation of Htt polypeptide was examined in brain samples obtained from wild-type, homozygous or heterozygous knock-in mouse models of HD, which represent the closest model of human HD in terms of Htt polypeptide expression levels and processing. Experiments were performed to test two different mouse models that carry 111Q or 140Q polyglutamine stretches in the murine HD gene homolog (19, 20). Using the AcK444 antibody, it was found that only mutant Htt polypeptide was acetylated in HD mouse brains while no acetylation of the wild-type Htt polypeptide was detected (FIG. 4A, 4B). These results are in agreement with the data obtained in cultured cells where preferential acetylation of mutant Htt polypeptide was observed (FIG. 1C).

Next, it was examined whether increased acetylation of mutant Htt polypeptide may affect its expression levels in mouse brains. To address this question, heterozygous HD mice (HdH$^{7Q/111Q}$) were treated with HDAC inhibitors (TSA and NAM) for 10 days, followed by the analysis of Htt polypeptide expression. To allow for distinct separation of mutant and wild type Htt polypeptide by SDS-PAGE (FIG. 4C) as well as reliable quantification, a protocol for western blotting of high molecular weight proteins was employed (21). In order to correct for possible transcriptional effects of HDAC inhibitors, a ratio of mutant Htt polypeptide over wild-type Htt polypeptide levels was measured to monitor the effect of HDAC inhibitors on the levels of mutant Htt polypeptide. This approach was possible because no acetylation of wild-type Htt polypeptide was detected at baseline or after the treatment with HDAC inhibitors (FIG. 4A, 4B, and data not shown). It was reasoned that the ratio of mutant Htt polypeptide over wild-type Htt polypeptide in the same heterozygous animal could provide the most reliable measure of the effects of acetylation on Htt polypeptide levels. Using this strategy, a significant decrease in the levels of mutant Htt polypeptide was detected in animals treated with HDAC inhibitors as compared to vehicle-treated littermates (FIG. 4C, 4D). These results suggest that acetylation of mutant Htt polypeptide in vivo leads to decreased levels of the mutant protein which in turn may contribute to protective effects of HDAC inhibitors in mouse models of HD.

In summary, it has now been demonstrated that mutant Htt polypeptide can be acetylated by CBP and in response to HDAC inhibitor treatment and that acetylation affects mutant Htt polypeptide clearance and toxicity. Previous studies implicated CBP as one of the important targets of mutant Htt polypeptide. For example, loss of CBP function through sequestration into mutant Htt polypeptide aggregates and interference of CBP HAT activity have been suggested as major cellular defects contributing to HD pathogenesis (6, 7, 22, 23). Studies using various cell culture models of HD demonstrated that depletion of CBP contributed to toxicity caused by mutant Htt polypeptide (24). In *C. elegans*, haplodeficiency of cbp-1 increased Htt toxicity, and HAT activity of cbp-1 was critical for protection against Htt toxicity (2). Moreover, inhibition of class I and class II HDACs by TSA reduced the degeneration of *C. elegans* neurons induced by mutant Htt in a TSA dose-dependent manner (2). In addition, pharmacological inhibition of HDAC with butyrate or SAHA and genetic reduction of HDAC activity were shown to rescue the lethality and degeneration in *Drosophila* model of HD (7). Importantly, administration of HDAC inhibitors improved survival and disease symptoms in mouse models of HD (3-5).

In this study, a novel mechanism is proposed on how CBP or HDAC inhibitor-mediated acetylation contributes to HD pathogenesis. It has now been shown that acetylation of mutant Htt by CBP or HDAC inhibitors led to increased autophagic activity and subsequent clearance of mutant Htt polypeptide. Recent studies suggested that disruption of basal autophagy resulted in abnormal accumulation of proteins and neurodegeneration (25, 26). In addition, clearance of mutant Htt polypeptide by autophagy is emerging as an important cellular defense mechanism in HD (11, 13, 15, 16). Although baseline autophagy does not appear to be sufficient to prevent accumulation of mutant Htt polypeptide and progression of the disease, the finding demonstrated that specific acetylation of mutant Htt facilitates processing of mutant huntingtin by autophagy, leading to decreased levels of mutant Htt polypeptide. Importantly, in HD knock-in mice, acetylation of mutant but not the wild type Htt polypeptide was detected. Consequently, treatment with HDAC inhibitors led to a decrease in the levels of mutant Htt polypeptide without affecting levels of normal Htt polypeptide. It may be assumed that a specific decrease in mutant Htt polypeptide, even if relatively minor, may have a dramatic impact on disease onset and progression in HD. To achieve such a therapeutic goal, without producing significant side effects, it is important to identify novel HDAC inhibitors that will selectively promote acetylation of mutant Htt polypeptide and thereby facilitate its clearance from HD brain.

References

1. Gatchel, J. R. & Zoghbi, H. Y. Diseases of unstable repeat expansion: mechanisms and common principles. Nat Rev Genet. 6, 743-55 (2005).
2. Bates, E. A., Victor, M., Jones, A. K., Shi, Y. & Hart, A. C. Differential contributions of *Caenorhabditis elegans* histone deacetylases to huntingtin polyglutamine toxicity. J Neurosci 26, 2830-8 (2006).
3. Ferrante, R. J. et al. Histone deacetylase inhibition by sodium butyrate chemotherapy ameliorates the neurodegenerative phenotype in Huntington's disease mice. J Neurosci 23, 9418-27 (2003).
4. Gardian, G. et al. Neuroprotective effects of phenylbutyrate in the N171-82Q transgenic mouse model of Huntington's disease. J Biol Chem 280, 556-63 (2005).
5. Hockly, E. et al. Suberoylanilide hydroxamic acid, a histone deacetylase inhibitor, ameliorates motor deficits in a mouse model of Huntington's disease. Proc Natl Acad Sci USA 100, 2041-6 (2003).
6. Nucifora, F. C., Jr. et al. Interference by huntingtin and atrophin-1 with cbp-mediated transcription leading to cellular toxicity. Science 291, 2423-8 (2001).
7. Steffan, J. S. et al. Histone deacetylase inhibitors arrest polyglutamine-dependent neurodegeneration in *Drosophila*. Nature 413, 739-43 (2001).
8. Goodman, R. H. & Smolik, S. CBP/p300 in cell growth, transformation, and development. Genes Dev 14, 1553-77 (2000).
9. Muraoka, M. et al. p300 gene alterations in colorectal and gastric carcinomas. Oncogene 12, 1565-9 (1996).
10. Taylor, J. P. et al. Aberrant histone acetylation, altered transcription, and retinal degeneration in a *Drosophila* model of polyglutamine disease are rescued by CREB-binding protein. Genes Dev 17, 1463-8 (2003).
11. Kegel, K. B. et al. Huntingtin expression stimulates endosomal-lysosomal activity, endosome tubulation, and autophagy. J Neurosci 20, 7268-78 (2000).
12. Martin-Aparicio, E. et al. Proteasomal-dependent aggregate reversal and absence of cell death in a conditional mouse model of Huntington's disease. J Neurosci 21, 8772-81 (2001).
13. Ravikumar, B., Duden, R. & Rubinsztein, D.C. Aggregate-prone proteins with polyglutamine and polyalanine expansions are degraded by autophagy. Hum Mol Genet. 11, 1107-17 (2002).
14. Saudou, F., Finkbeiner, S., Devys, D. & Greenberg, M. E. Huntingtin acts in the nucleus to induce apoptosis but death does not correlate with the formation of intranuclear inclusions. Cell 95, 55-66 (1998).
15. Shibata, M. et al. Regulation of intracellular accumulation of mutant Huntingtin by Beclin 1. J Biol Chem 281, 14474-85 (2006).
16. Yamamoto, A., Cremona, M. L. & Rothman, J. E. Autophagy-mediated clearance of huntingtin aggregates triggered by the insulin-signaling pathway. J Cell Biol 172, 719-31 (2006).
17. Mizushima, N. Methods for monitoring autophagy. Int J Biochem Cell Biol 36, 2491-502 (2004).
18. Kabeya, Y. et al. LC3, a mammalian homologue of yeast Apg8p, is localized in autophagosome membranes after processing. Embo J 19, 5720-8 (2000).

19. Menalled, L. B., Sison, J. D., Dragatsis, I., Zeitlin, S. & Chesselet, M. F. Time course of early motor and neuropathological anomalies in a knock-in mouse model of Huntington's disease with 140 CAG repeats. J Comp Neurol 465, 11-26 (2003).

20. Wheeler, V. C. et al. Length-dependent gametic CAG repeat instability in the Huntington's disease knock-in mouse. Hum Mol Genet. 8, 115-22 (1999).

21. Fritz, J. D., Swartz, D. R. & Greater, M. L. Factors affecting polyacrylamide gel electrophoresis and electroblotting of high-molecular-weight myofibrillar proteins. Anal Biochem 180, 205-10 (1989).

22. Kazantsev, A., Preisinger, E., Dranovsky, A., Goldgaber, D. & Housman, D. Insoluble detergent-resistant aggregates form between pathological and nonpathological lengths of polyglutamine in mammalian cells. Proc Natl Acad Sci USA 96, 11404-9 (1999).

23. Steffan, J. S. et al. The Huntington's disease protein interacts with p53 and CREB-binding protein and represses transcription. Proc Natl Acad Sci USA 97, 6763-8 (2000).

24. Cong, S.Y. et al. Mutant huntingtin represses CBP, but not p300, by binding and protein degradation. Mol Cell Neurosci 30, 560-71 (2005).

25. Hara, T. et al. Suppression of basal autophagy in neural cells causes neurodegenerative disease in mice. Nature 441, 885-9 (2006).

26. Komatsu, M. et al. Loss of autophagy in the central nervous system causes neurodegeneration in mice. Nature 441, 880-4 (2006).

27. Trottier, Y. et al. Cellular localization of the Huntington's disease protein and discrimination of the wild-type and mutated form. Nat Genet. 10, 104-10 (1995).

28. Campbell, R. E. et al. A monomeric red fluorescent protein. Proc Natl Acad Sci USA 99, 7877-82 (2002).

29. Trettel, F. et al. Dominant phenotypes produced by the HD mutation in STHdh(Q111) striatal cells. Hum Mol Genet. 9, 2799-809 (2000).

30. Dunah, A. W. et al. Sp1 and TAFII130 transcriptional activity disrupted in early Huntington's disease. Science 296, 2238-43 (2002).

Although the invention has been described in detail for the purpose of illustration, it is understood that such detail is solely for that purpose and variations can be made by those skilled in the art without departing from the spirit and scope of the invention which is defined by the following claims.

The contents of all references, patents and published patent applications cited throughout this application are incorporated herein by reference in their entirety.

We claim:

1. An isolated monoclonal antibody or antigen-binding fragment thereof that binds specifically to an epitope of acetylated human Htt polypeptide, but does not bind specifically to non-acetylated human Htt polypeptide, wherein the epitope comprises lysine K444 of human Htt polypeptide.

2. The isolated monoclonal antibody or antigen-binding fragment thereof of claim 1, wherein the epitope comprises the amino acid sequence set forth as SEQ ID NO:13.

3. The isolated monoclonal antibody or antigen-binding fragment thereof of claim 1, wherein the antibody competitively inhibits binding of an AcK444 polyclonal antibody to the epitope.

4. The isolated monoclonal antibody or antigen-binding fragment thereof of claim 1, wherein the antibody or antigen-binding fragment thereof is attached to a detectable label.

5. A hybridoma that produces the monoclonal antibody of claim 1.

6. A hybridoma cell line that produces the monoclonal antibody of claim 1.

7. A composition comprising the monoclonal antibody or antigen-binding fragment thereof of claim 1.

* * * * *

UNITED STATES PATENT AND TRADEMARK OFFICE

CERTIFICATE OF CORRECTION

PATENT NO. : 9,284,366 B2
APPLICATION NO. : 11/981830
DATED : March 15, 2016
INVENTOR(S) : Dimitri Krainc et al.

It is certified that error appears in the above-identified patent and that said Letters Patent is hereby corrected as shown below:

In the Claims:

Claim 1, starting at column 115, line 39, should read:

1. An isolated monoclonal antibody or antigen-binding fragment thereof that binds specifically to an epitope of acetylated human Htt polypeptide, but does not bind specifically to non-acetylated human Htt polypeptide, wherein the epitope comprises acetylated lysine K444 of human Htt polypeptide.

Signed and Sealed this
Seventeenth Day of May, 2016

Michelle K. Lee
*Director of the United States Patent and Trademark Office*

SEQUENCE LISTING

```
<160> NUMBER OF SEQ ID NOS: 54

<210> SEQ ID NO 1
<211> LENGTH: 3144
<212> TYPE: PRT
<213> ORGANISM: Homo sapiens

<400> SEQUENCE: 1

Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln Gln Gln
            20                  25                  30

Gln Gln Gln Gln Gln Gln Gln Gln Pro Pro Pro Pro Pro Pro Pro Pro
        35                  40                  45

Pro Pro Pro Gln Leu Pro Gln Pro Pro Pro Gln Ala Gln Pro Leu Leu
    50                  55                  60

Pro Gln Pro Gln Pro Pro Pro Pro Pro Pro Pro Pro Pro Pro Gly Pro
65                  70                  75                  80

Ala Val Ala Glu Glu Pro Leu His Arg Pro Lys Lys Glu Leu Ser Ala
                85                  90                  95

Thr Lys Lys Asp Arg Val Asn His Cys Leu Thr Ile Cys Glu Asn Ile
            100                 105                 110

Val Ala Gln Ser Val Arg Asn Ser Pro Glu Phe Gln Lys Leu Leu Gly
        115                 120                 125

Ile Ala Met Glu Leu Phe Leu Leu Cys Ser Asp Asp Ala Glu Ser Asp
    130                 135                 140

Val Arg Met Val Ala Asp Glu Cys Leu Asn Lys Val Ile Lys Ala Leu
145                 150                 155                 160

Met Asp Ser Asn Leu Pro Arg Leu Gln Leu Glu Leu Tyr Lys Glu Ile
                165                 170                 175

Lys Lys Asn Gly Ala Pro Arg Ser Leu Arg Ala Ala Leu Trp Arg Phe
            180                 185                 190

Ala Glu Leu Ala His Leu Val Arg Pro Gln Lys Cys Arg Pro Tyr Leu
```

-continued 195                 200                 205

Val Asn Leu Leu Pro Cys Leu Thr Arg Thr Ser Lys Arg Pro Glu Glu
    210                 215                 220

Ser Val Gln Glu Thr Leu Ala Ala Ala Val Pro Lys Ile Met Ala Ser
225                 230                 235                 240

Phe Gly Asn Phe Ala Asn Asp Asn Glu Ile Lys Val Leu Leu Lys Ala
                245                 250                 255

Phe Ile Ala Asn Leu Lys Ser Ser Ser Pro Thr Ile Arg Arg Thr Ala
            260                 265                 270

Ala Gly Ser Ala Val Ser Ile Cys Gln His Ser Arg Arg Thr Gln Tyr
        275                 280                 285

Phe Tyr Ser Trp Leu Leu Asn Val Leu Leu Gly Leu Leu Val Pro Val
    290                 295                 300

Glu Asp Glu His Ser Thr Leu Leu Ile Leu Gly Val Leu Leu Thr Leu
305                 310                 315                 320

Arg Tyr Leu Val Pro Leu Leu Gln Gln Gln Val Lys Asp Thr Ser Leu
                325                 330                 335

Lys Gly Ser Phe Gly Val Thr Arg Lys Glu Met Glu Val Ser Pro Ser
            340                 345                 350

Ala Glu Gln Leu Val Gln Val Tyr Glu Leu Thr Leu His His Thr Gln
        355                 360                 365

His Gln Asp His Asn Val Val Thr Gly Ala Leu Glu Leu Leu Gln Gln
    370                 375                 380

Leu Phe Arg Thr Pro Pro Pro Glu Leu Leu Gln Thr Leu Thr Ala Val
385                 390                 395                 400

Gly Gly Ile Gly Gln Leu Thr Ala Ala Lys Glu Glu Ser Gly Gly Arg
                405                 410                 415

Ser Arg Ser Gly Ser Ile Val Glu Leu Ile Ala Gly Gly Gly Ser Ser
            420                 425                 430

Cys Ser Pro Val Leu Ser Arg Lys Gln Lys Gly Lys Val Leu Leu Gly
        435                 440                 445

Glu Glu Glu Ala Leu Glu Asp Asp Ser Glu Ser Arg Ser Asp Val Ser
    450                 455                 460

Ser Ser Ala Leu Thr Ala Ser Val Lys Asp Glu Ile Ser Gly Glu Leu
465                 470                 475                 480

Ala Ala Ser Ser Gly Val Ser Thr Pro Gly Ser Ala Gly His Asp Ile
                485                 490                 495

Ile Thr Glu Gln Pro Arg Ser Gln His Thr Leu Gln Ala Asp Ser Val
            500                 505                 510

Asp Leu Ala Ser Cys Asp Leu Thr Ser Ser Ala Thr Asp Gly Asp Glu
        515                 520                 525

Glu Asp Ile Leu Ser His Ser Ser Ser Gln Val Ser Ala Val Pro Ser
    530                 535                 540

Asp Pro Ala Met Asp Leu Asn Asp Gly Thr Gln Ala Ser Ser Pro Ile
545                 550                 555                 560

Ser Asp Ser Ser Gln Thr Thr Thr Glu Gly Pro Asp Ser Ala Val Thr
                565                 570                 575

Pro Ser Asp Ser Ser Glu Ile Val Leu Asp Gly Thr Asp Asn Gln Tyr
            580                 585                 590

Leu Gly Leu Gln Ile Gly Gln Pro Gln Asp Glu Asp Glu Glu Ala Thr
        595                 600                 605

Gly Ile Leu Pro Asp Glu Ala Ser Glu Ala Phe Arg Asn Ser Ser Met
    610                 615                 620

-continued

```
Ala Leu Gln Gln Ala His Leu Leu Lys Asn Met Ser His Cys Arg Gln
625                 630                 635                 640

Pro Ser Asp Ser Ser Val Asp Lys Phe Val Leu Arg Asp Glu Ala Thr
                645                 650                 655

Glu Pro Gly Asp Gln Glu Asn Lys Pro Cys Arg Ile Lys Gly Asp Ile
            660                 665                 670

Gly Gln Ser Thr Asp Asp Asp Ser Ala Pro Leu Val His Cys Val Arg
        675                 680                 685

Leu Leu Ser Ala Ser Phe Leu Leu Thr Gly Gly Lys Asn Val Leu Val
    690                 695                 700

Pro Asp Arg Asp Val Arg Val Ser Val Lys Ala Leu Ala Leu Ser Cys
705                 710                 715                 720

Val Gly Ala Ala Val Ala Leu His Pro Glu Ser Phe Phe Ser Lys Leu
                725                 730                 735

Tyr Lys Val Pro Leu Asp Thr Thr Glu Tyr Pro Glu Glu Gln Tyr Val
            740                 745                 750

Ser Asp Ile Leu Asn Tyr Ile Asp His Gly Asp Pro Gln Val Arg Gly
        755                 760                 765

Ala Thr Ala Ile Leu Cys Gly Thr Leu Ile Cys Ser Ile Leu Ser Arg
    770                 775                 780

Ser Arg Phe His Val Gly Asp Trp Met Gly Thr Ile Arg Thr Leu Thr
785                 790                 795                 800

Gly Asn Thr Phe Ser Leu Ala Asp Cys Ile Pro Leu Leu Arg Lys Thr
                805                 810                 815

Leu Lys Asp Glu Ser Ser Val Thr Cys Lys Leu Ala Cys Thr Ala Val
            820                 825                 830

Arg Asn Cys Val Met Ser Leu Cys Ser Ser Ser Tyr Ser Glu Leu Gly
        835                 840                 845

Leu Gln Leu Ile Ile Asp Val Leu Thr Leu Arg Asn Ser Ser Tyr Trp
    850                 855                 860

Leu Val Arg Thr Glu Leu Leu Glu Thr Leu Ala Glu Ile Asp Phe Arg
865                 870                 875                 880

Leu Val Ser Phe Leu Glu Ala Lys Ala Glu Asn Leu His Arg Gly Ala
                885                 890                 895

His His Tyr Thr Gly Leu Leu Lys Leu Gln Glu Arg Val Leu Asn Asn
            900                 905                 910

Val Val Ile His Leu Leu Gly Asp Glu Asp Pro Arg Val Arg His Val
        915                 920                 925

Ala Ala Ala Ser Leu Ile Arg Leu Val Pro Lys Leu Phe Tyr Lys Cys
    930                 935                 940

Asp Gln Gly Gln Ala Asp Pro Val Val Ala Val Ala Arg Asp Gln Ser
945                 950                 955                 960

Ser Val Tyr Leu Lys Leu Leu Met His Glu Thr Gln Pro Pro Ser His
                965                 970                 975

Phe Ser Val Ser Thr Ile Thr Arg Ile Tyr Arg Gly Tyr Asn Leu Leu
            980                 985                 990

Pro Ser Ile Thr Asp Val Thr Met  Glu Asn Asn Leu Ser  Arg Val Ile
        995                 1000                 1005

Ala Ala  Val Ser His Glu Leu  Ile Thr Ser Thr Thr  Arg Ala Leu
    1010                 1015                 1020

Thr Phe  Gly Cys Cys Glu Ala  Leu Cys Leu Leu Ser  Thr Ala Phe
    1025                 1030                 1035
```

```
Pro Val  Cys Ile Trp Ser Leu  Gly Trp His Cys Gly  Val Pro Pro
    1040                 1045                 1050

Leu Ser  Ala Ser Asp Glu Ser  Arg Lys Ser Cys Thr  Val Gly Met
    1055                 1060                 1065

Ala Thr  Met Ile Leu Thr Leu  Leu Ser Ser Ala Trp  Phe Pro Leu
    1070                 1075                 1080

Asp Leu  Ser Ala His Gln Asp  Ala Leu Ile Leu Ala  Gly Asn Leu
    1085                 1090                 1095

Leu Ala  Ala Ser Ala Pro Lys  Ser Leu Arg Ser Ser  Trp Ala Ser
    1100                 1105                 1110

Glu Glu  Glu Ala Asn Pro Ala  Ala Thr Lys Gln Glu  Glu Val Trp
    1115                 1120                 1125

Pro Ala  Leu Gly Asp Arg Ala  Leu Val Pro Met Val  Glu Gln Leu
    1130                 1135                 1140

Phe Ser  His Leu Leu Lys Val  Ile Asn Ile Cys Ala  His Val Leu
    1145                 1150                 1155

Asp Asp  Val Ala Pro Gly Pro  Ala Ile Lys Ala Ala  Leu Pro Ser
    1160                 1165                 1170

Leu Thr  Asn Pro Pro Ser Leu  Ser Pro Ile Arg Arg  Lys Gly Lys
    1175                 1180                 1185

Glu Lys  Glu Pro Gly Glu Gln  Ala Ser Val Pro Leu  Ser Pro Lys
    1190                 1195                 1200

Lys Gly  Ser Glu Ala Ser Ala  Ala Ser Arg Gln Ser  Asp Thr Ser
    1205                 1210                 1215

Gly Pro  Val Thr Thr Ser Lys  Ser Ser Ser Leu Gly  Ser Phe Tyr
    1220                 1225                 1230

His Leu  Pro Ser Tyr Leu Lys  Leu His Asp Val Leu  Lys Ala Thr
    1235                 1240                 1245

His Ala  Asn Tyr Lys Val Thr  Leu Asp Leu Gln Asn  Ser Thr Glu
    1250                 1255                 1260

Lys Phe  Gly Gly Phe Leu Arg  Ser Ala Leu Asp Val  Leu Ser Gln
    1265                 1270                 1275

Ile Leu  Glu Leu Ala Thr Leu  Gln Asp Ile Gly Lys  Cys Val Glu
    1280                 1285                 1290

Glu Ile  Leu Gly Tyr Leu Lys  Ser Cys Phe Ser Arg  Glu Pro Met
    1295                 1300                 1305

Met Ala  Thr Val Cys Val Gln  Gln Leu Leu Lys Thr  Leu Phe Gly
    1310                 1315                 1320

Thr Asn  Leu Ala Ser Gln Phe  Asp Gly Leu Ser Ser  Asn Pro Ser
    1325                 1330                 1335

Lys Ser  Gln Gly Arg Ala Gln  Arg Leu Gly Ser Ser  Ser Val Arg
    1340                 1345                 1350

Pro Gly  Leu Tyr His Tyr Cys  Phe Met Ala Pro Tyr  Thr His Phe
    1355                 1360                 1365

Thr Gln  Ala Leu Ala Asp Ala  Ser Leu Arg Asn Met  Val Gln Ala
    1370                 1375                 1380

Glu Gln  Glu Asn Asp Thr Ser  Gly Trp Phe Asp Val  Leu Gln Lys
    1385                 1390                 1395

Val Ser  Thr Gln Leu Lys Thr  Asn Leu Thr Ser Val  Thr Lys Asn
    1400                 1405                 1410

Arg Ala  Asp Lys Asn Ala Ile  His Asn His Ile Arg  Leu Phe Glu
    1415                 1420                 1425

Pro Leu  Val Ile Lys Ala Leu  Lys Gln Tyr Thr Thr  Thr Thr Cys
```

-continued

```
    1430                1435                1440

Val Gln  Leu Gln Lys Gln Val  Leu Asp Leu Leu Ala  Gln Leu Val
    1445                1450                1455

Gln Leu  Arg Val Asn Tyr Cys  Leu Leu Asp Ser Asp  Gln Val Phe
    1460                1465                1470

Ile Gly  Phe Val Leu Lys Gln  Phe Glu Tyr Ile Glu  Val Gly Gln
    1475                1480                1485

Phe Arg  Glu Ser Glu Ala Ile  Ile Pro Asn Ile Phe  Phe Phe Leu
    1490                1495                1500

Val Leu  Leu Ser Tyr Glu Arg  Tyr His Ser Lys Gln  Ile Ile Gly
    1505                1510                1515

Ile Pro  Lys Ile Ile Gln Leu  Cys Asp Gly Ile Met  Ala Ser Gly
    1520                1525                1530

Arg Lys  Ala Val Thr His Ala  Ile Pro Ala Leu Gln  Pro Ile Val
    1535                1540                1545

His Asp  Leu Phe Val Leu Arg  Gly Thr Asn Lys Ala  Asp Ala Gly
    1550                1555                1560

Lys Glu  Leu Glu Thr Gln Lys  Glu Val Val Val Ser  Met Leu Leu
    1565                1570                1575

Arg Leu  Ile Gln Tyr His Gln  Val Leu Glu Met Phe  Ile Leu Val
    1580                1585                1590

Leu Gln  Gln Cys His Lys Glu  Asn Glu Asp Lys Trp  Lys Arg Leu
    1595                1600                1605

Ser Arg  Gln Ile Ala Asp Ile  Ile Leu Pro Met Leu  Ala Lys Gln
    1610                1615                1620

Gln Met  His Ile Asp Ser His  Glu Ala Leu Gly Val  Leu Asn Thr
    1625                1630                1635

Leu Phe  Glu Ile Leu Ala Pro  Ser Ser Leu Arg Pro  Val Asp Met
    1640                1645                1650

Leu Leu  Arg Ser Met Phe Val  Thr Pro Asn Thr Met  Ala Ser Val
    1655                1660                1665

Ser Thr  Val Gln Leu Trp Ile  Ser Gly Ile Leu Ala  Ile Leu Arg
    1670                1675                1680

Val Leu  Ile Ser Gln Ser Thr  Glu Asp Ile Val Leu  Ser Arg Ile
    1685                1690                1695

Gln Glu  Leu Ser Phe Ser Pro  Tyr Leu Ile Ser Cys  Thr Val Ile
    1700                1705                1710

Asn Arg  Leu Arg Asp Gly Asp  Ser Thr Ser Thr Leu  Glu Glu His
    1715                1720                1725

Ser Glu  Gly Lys Gln Ile Lys  Asn Leu Pro Glu Glu  Thr Phe Ser
    1730                1735                1740

Arg Phe  Leu Leu Gln Leu Val  Gly Ile Leu Leu Glu  Asp Ile Val
    1745                1750                1755

Thr Lys  Gln Leu Lys Val Glu  Met Ser Glu Gln Gln  His Thr Phe
    1760                1765                1770

Tyr Cys  Gln Glu Leu Gly Thr  Leu Leu Met Cys Leu  Ile His Ile
    1775                1780                1785

Phe Lys  Ser Gly Met Phe Arg  Arg Ile Thr Ala Ala  Ala Thr Arg
    1790                1795                1800

Leu Phe  Arg Ser Asp Gly Cys  Gly Gly Ser Phe Tyr  Thr Leu Asp
    1805                1810                1815

Ser Leu  Asn Leu Arg Ala Arg  Ser Met Ile Thr Thr  His Pro Ala
    1820                1825                1830
```

```
Leu Val  Leu Leu Trp Cys Gln  Ile Leu Leu Leu Val  Asn His Thr
    1835                 1840                 1845

Asp Tyr  Arg Trp Trp Ala Glu  Val Gln Gln Thr Pro  Lys Arg His
    1850                 1855                 1860

Ser Leu  Ser Ser Thr Lys Leu  Leu Ser Pro Gln Met  Ser Gly Glu
    1865                 1870                 1875

Glu Glu  Asp Ser Asp Leu Ala  Ala Lys Leu Gly Met  Cys Asn Arg
    1880                 1885                 1890

Glu Ile  Val Arg Arg Gly Ala  Leu Ile Leu Phe Cys  Asp Tyr Val
    1895                 1900                 1905

Cys Gln  Asn Leu His Asp Ser  Glu His Leu Thr Trp  Leu Ile Val
    1910                 1915                 1920

Asn His  Ile Gln Asp Leu Ile  Ser Leu Ser His Glu  Pro Pro Val
    1925                 1930                 1935

Gln Asp  Phe Ile Ser Ala Val  His Arg Asn Ser Ala  Ala Ser Gly
    1940                 1945                 1950

Leu Phe  Ile Gln Ala Ile Gln  Ser Arg Cys Glu Asn  Leu Ser Thr
    1955                 1960                 1965

Pro Thr  Met Leu Lys Lys Thr  Leu Gln Cys Leu Glu  Gly Ile His
    1970                 1975                 1980

Leu Ser  Gln Ser Gly Ala Val  Leu Thr Leu Tyr Val  Asp Arg Leu
    1985                 1990                 1995

Leu Cys  Thr Pro Phe Arg Val  Leu Ala Arg Met Val  Asp Ile Leu
    2000                 2005                 2010

Ala Cys  Arg Arg Val Glu Met  Leu Leu Ala Ala Asn  Leu Gln Ser
    2015                 2020                 2025

Ser Met  Ala Gln Leu Pro Met  Glu Glu Leu Asn Arg  Ile Gln Glu
    2030                 2035                 2040

Tyr Leu  Gln Ser Ser Gly Leu  Ala Gln Arg His Gln  Arg Leu Tyr
    2045                 2050                 2055

Ser Leu  Leu Asp Arg Phe Arg  Leu Ser Thr Met Gln  Asp Ser Leu
    2060                 2065                 2070

Ser Pro  Ser Pro Pro Val Ser  Ser His Pro Leu Asp  Gly Asp Gly
    2075                 2080                 2085

His Val  Ser Leu Glu Thr Val  Ser Pro Asp Lys Asp  Trp Tyr Val
    2090                 2095                 2100

His Leu  Val Lys Ser Gln Cys  Trp Thr Arg Ser Asp  Ser Ala Leu
    2105                 2110                 2115

Leu Glu  Gly Ala Glu Leu Val  Asn Arg Ile Pro Ala  Glu Asp Met
    2120                 2125                 2130

Asn Ala  Phe Met Met Asn Ser  Glu Phe Asn Leu Ser  Leu Leu Ala
    2135                 2140                 2145

Pro Cys  Leu Ser Leu Gly Met  Ser Glu Ile Ser Gly  Gly Gln Lys
    2150                 2155                 2160

Ser Ala  Leu Phe Glu Ala Ala  Arg Glu Val Thr Leu  Ala Arg Val
    2165                 2170                 2175

Ser Gly  Thr Val Gln Gln Leu  Pro Ala Val His His  Val Phe Gln
    2180                 2185                 2190

Pro Glu  Leu Pro Ala Glu Pro  Ala Ala Tyr Trp Ser  Lys Leu Asn
    2195                 2200                 2205

Asp Leu  Phe Gly Asp Ala Ala  Leu Tyr Gln Ser Leu  Pro Thr Leu
    2210                 2215                 2220
```

-continued

```
Ala Arg  Ala Leu Ala Gln Tyr  Leu Val Val Val Ser  Lys Leu Pro
    2225                 2230                 2235

Ser His  Leu His Leu Pro Pro  Glu Lys Glu Lys Asp  Ile Val Lys
    2240                 2245                 2250

Phe Val  Val Ala Thr Leu Glu  Ala Leu Ser Trp His  Leu Ile His
    2255                 2260                 2265

Glu Gln  Ile Pro Leu Ser Leu  Asp Leu Gln Ala Gly  Leu Asp Cys
    2270                 2275                 2280

Cys Cys  Leu Ala Leu Gln Leu  Pro Gly Leu Trp Ser  Val Val Ser
    2285                 2290                 2295

Ser Thr  Glu Phe Val Thr His  Ala Cys Ser Leu Ile  Tyr Cys Val
    2300                 2305                 2310

His Phe  Ile Leu Glu Ala Val  Ala Val Gln Pro Gly  Glu Gln Leu
    2315                 2320                 2325

Leu Ser  Pro Glu Arg Arg Thr  Asn Thr Pro Lys Ala  Ile Ser Glu
    2330                 2335                 2340

Glu Glu  Glu Glu Val Asp Pro  Asn Thr Gln Asn Pro  Lys Tyr Ile
    2345                 2350                 2355

Thr Ala  Ala Cys Glu Met Val  Ala Glu Met Val Glu  Ser Leu Gln
    2360                 2365                 2370

Ser Val  Leu Ala Leu Gly His  Lys Arg Asn Ser Gly  Val Pro Ala
    2375                 2380                 2385

Phe Leu  Thr Pro Leu Leu Arg  Asn Ile Ile Ile Ser  Leu Ala Arg
    2390                 2395                 2400

Leu Pro  Leu Val Asn Ser Tyr  Thr Arg Val Pro Pro  Leu Val Trp
    2405                 2410                 2415

Lys Leu  Gly Trp Ser Pro Lys  Pro Gly Gly Asp Phe  Gly Thr Ala
    2420                 2425                 2430

Phe Pro  Glu Ile Pro Val Glu  Phe Leu Gln Glu Lys  Glu Val Phe
    2435                 2440                 2445

Lys Glu  Phe Ile Tyr Arg Ile  Asn Thr Leu Gly Trp  Thr Ser Arg
    2450                 2455                 2460

Thr Gln  Phe Glu Glu Thr Trp  Ala Thr Leu Leu Gly  Val Leu Val
    2465                 2470                 2475

Thr Gln  Pro Leu Val Met Glu  Gln Glu Glu Ser Pro  Pro Glu Glu
    2480                 2485                 2490

Asp Thr  Glu Arg Thr Gln Ile  Asn Val Leu Ala Val  Gln Ala Ile
    2495                 2500                 2505

Thr Ser  Leu Val Leu Ser Ala  Met Thr Val Pro Val  Ala Gly Asn
    2510                 2515                 2520

Pro Ala  Val Ser Cys Leu Glu  Gln Gln Pro Arg Asn  Lys Pro Leu
    2525                 2530                 2535

Lys Ala  Leu Asp Thr Arg Phe  Gly Arg Lys Leu Ser  Ile Ile Arg
    2540                 2545                 2550

Gly Ile  Val Glu Gln Glu Ile  Gln Ala Met Val Ser  Lys Arg Glu
    2555                 2560                 2565

Asn Ile  Ala Thr His His Leu  Tyr Gln Ala Trp Asp  Pro Val Pro
    2570                 2575                 2580

Ser Leu  Ser Pro Ala Thr Thr  Gly Ala Leu Ile Ser  His Glu Lys
    2585                 2590                 2595

Leu Leu  Leu Gln Ile Asn Pro  Glu Arg Glu Leu Gly  Ser Met Ser
    2600                 2605                 2610

Tyr Lys  Leu Gly Gln Val Ser  Ile His Ser Val Trp  Leu Gly Asn
```

```
    2615                2620                2625

Ser Ile  Thr Pro Leu Arg Glu  Glu Glu Trp Asp Glu  Glu Glu Glu
    2630                2635                2640

Glu Glu  Ala Asp Ala Pro Ala  Pro Ser Ser Pro Pro  Thr Ser Pro
    2645                2650                2655

Val Asn  Ser Arg Lys His Arg  Ala Gly Val Asp Ile  His Ser Cys
    2660                2665                2670

Ser Gln  Phe Leu Leu Glu Leu  Tyr Ser Arg Trp Ile  Leu Pro Ser
    2675                2680                2685

Ser Ser  Ala Arg Arg Thr Pro  Ala Ile Leu Ile Ser  Glu Val Val
    2690                2695                2700

Arg Ser  Leu Leu Val Val Ser  Asp Leu Phe Thr Glu  Arg Asn Gln
    2705                2710                2715

Phe Glu  Leu Met Tyr Val Thr  Leu Thr Glu Leu Arg  Arg Val His
    2720                2725                2730

Pro Ser  Glu Asp Glu Ile Leu  Ala Gln Tyr Leu Val  Pro Ala Thr
    2735                2740                2745

Cys Lys  Ala Ala Ala Val Leu  Gly Met Asp Lys Ala  Val Ala Glu
    2750                2755                2760

Pro Val  Ser Arg Leu Leu Glu  Ser Thr Leu Arg Ser  Ser His Leu
    2765                2770                2775

Pro Ser  Arg Val Gly Ala Leu  His Gly Val Leu Tyr  Val Leu Glu
    2780                2785                2790

Cys Asp  Leu Leu Asp Asp Thr  Ala Lys Gln Leu Ile  Pro Val Ile
    2795                2800                2805

Ser Asp  Tyr Leu Leu Ser Asn  Leu Lys Gly Ile Ala  His Cys Val
    2810                2815                2820

Asn Ile  His Ser Gln Gln His  Val Leu Val Met Cys  Ala Thr Ala
    2825                2830                2835

Phe Tyr  Leu Ile Glu Asn Tyr  Pro Leu Asp Val Gly  Pro Glu Phe
    2840                2845                2850

Ser Ala  Ser Ile Ile Gln Met  Cys Gly Val Met Leu  Ser Gly Ser
    2855                2860                2865

Glu Glu  Ser Thr Pro Ser Ile  Ile Tyr His Cys Ala  Leu Arg Gly
    2870                2875                2880

Leu Glu  Arg Leu Leu Leu Ser  Glu Gln Leu Ser Arg  Leu Asp Ala
    2885                2890                2895

Glu Ser  Leu Val Lys Leu Ser  Val Asp Arg Val Asn  Val His Ser
    2900                2905                2910

Pro His  Arg Ala Met Ala Ala  Leu Gly Leu Met Leu  Thr Cys Met
    2915                2920                2925

Tyr Thr  Gly Lys Glu Lys Val  Ser Pro Gly Arg Thr  Ser Asp Pro
    2930                2935                2940

Asn Pro  Ala Ala Pro Asp Ser  Glu Ser Val Ile Val  Ala Met Glu
    2945                2950                2955

Arg Val  Ser Val Leu Phe Asp  Arg Ile Arg Lys Gly  Phe Pro Cys
    2960                2965                2970

Glu Ala  Arg Val Val Ala Arg  Ile Leu Pro Gln Phe  Leu Asp Asp
    2975                2980                2985

Phe Phe  Pro Pro Gln Asp Ile  Met Asn Lys Val Ile  Gly Glu Phe
    2990                2995                3000

Leu Ser  Asn Gln Gln Pro Tyr  Pro Gln Phe Met Ala  Thr Val Val
    3005                3010                3015
```

Tyr Lys Val Phe Gln Thr Leu His Ser Thr Gly Gln Ser Ser Met
3020 3025 3030

Val Arg Asp Trp Val Met Leu Ser Leu Ser Asn Phe Thr Gln Arg
3035 3040 3045

Ala Pro Val Ala Met Ala Thr Trp Ser Leu Ser Cys Phe Phe Val
3050 3055 3060

Ser Ala Ser Thr Ser Pro Trp Val Ala Ala Ile Leu Pro His Val
3065 3070 3075

Ile Ser Arg Met Gly Lys Leu Glu Gln Val Asp Val Asn Leu Phe
3080 3085 3090

Cys Leu Val Ala Thr Asp Phe Tyr Arg His Gln Ile Glu Glu Glu
3095 3100 3105

Leu Asp Arg Arg Ala Phe Gln Ser Val Leu Glu Val Val Ala Ala
3110 3115 3120

Pro Gly Ser Pro Tyr His Arg Leu Leu Thr Cys Leu Arg Asn Val
3125 3130 3135

His Lys Val Thr Thr Cys
3140

<210> SEQ ID NO 2
<211> LENGTH: 13481
<212> TYPE: DNA
<213> ORGANISM: Homo sapiens

<400> SEQUENCE: 2
gctgccggga cgggtccaag atggacggcc gctcaggttc tgcttttacc tgcggcccag 60
agccccattc attgccccgg tgctgagcgg cgccgcgagt cggcccgagg cctccgggga 120
ctgccgtgcc gggcgggaga ccgccatggc gaccctggaa aagctgatga aggccttcga 180
gtccctcaag tccttccagc agcagcagca gcagcagcag cagcagcagc agcagcagca 240
gcagcagcag cagcagcagc aacagccgcc accgccgccg ccgccgccgc cgcctcctca 300
gcttcctcag ccgccgccgc aggcacagcc gctgctgcct cagccgcagc cgcccccgcc 360
gccgcccccg ccgccacccg gcccggctgt ggctgaggag ccgctgcacc gaccaaagaa 420
agaactttca gctaccaaga aagaccgtgt gaatcattgt ctgacaatat gtgaaaacat 480
agtggcacag tctgtcagaa attctccaga atttcagaaa cttctgggca tcgctatgga 540
actttttctg ctgtgcagtg atgacgcaga gtcagatgtc aggatggtgg ctgacgaatg 600
cctcaacaaa gttatcaaag ctttgatgga ttctaatctt ccaaggttac agctcgagct 660
ctataaggaa attaaaaaga atggtgcccc tcggagtttg cgtgctgccc tgtggaggtt 720
tgctgagctg gctcacctgg ttcggcctca gaaatgcagg ccttacctgg tgaaccttct 780
gccgtgcctg actcgaacaa gcaagagacc cgaagaatca gtccaggaga ccttggctgc 840
agctgttccc aaaattatgg cttcttttgg caattttgca aatgacaatg aaattaaggt 900
tttgttaaag gccttcatag cgaacctgaa gtcaagctcc cccaccattc ggcggacagc 960
ggctggatca gcagtgagca tctgccagca ctcaagaagg acacaatatt tctatagttg 1020
gctactaaat gtgctcttag gcttactcgt tcctgtcgag gatgaacact ccactctgct 1080
gattcttggc gtgctgctca ccctgaggta tttggtgccc ttgctgcagc agcaggtcaa 1140
ggacacaagc ctgaaaggca gcttcggagt gacaaggaaa gaaatggaag tctctccttc 1200
tgcagagcag cttgtccagg tttatgaact gacgttacat catacacagc accaagacca 1260
caatgttgtg accggagccc tggagctgtt gcagcagctc ttcagaacgc ctccacccga 1320

-continued

```
gcttctgcaa accctgaccg cagtcggggg cattgggcag ctcaccgctg ctaaggagga   1380
gtctggtggc cgaagccgta gtgggagtat tgtggaactt atagctggag ggggttcctc   1440
atgcagccct gtcctttcaa gaaaacaaaa aggcaaagtg ctcttaggag aagaagaagc   1500
cttggaggat gactctgaat cgagatcgga tgtcagcagc tctgccttaa cagcctcagt   1560
gaaggatgag atcagtggag agctggctgc ttcttcaggg gtttccactc cagggtcagc   1620
aggtcatgac atcatcacag aacagccacg gtcacagcac acactgcagg cggactcagt   1680
ggatctggcc agctgtgact tgacaagctc tgccactgat ggggatgagg aggatatctt   1740
gagccacagc tccagccagg tcagcgccgt cccatctgac cctgccatgg acctgaatga   1800
tgggacccag gcctcgtcgc ccatcagcga cagctcccag accaccaccg aagggcctga   1860
ttcagctgtt accccttcag acagttctga aattgtgtta gacggtaccg acaaccagta   1920
tttgggcctg cagattggac agccccagga tgaagatgag gaagccacag gtattcttcc   1980
tgatgaagcc tcggaggcct tcaggaactc ttccatggcc cttcaacagg cacatttatt   2040
gaaaaacatg agtcactgca ggcagccttc tgacagcagt gttgataaat ttgtgttgag   2100
agatgaagct actgaaccgg gtgatcaaga aaacaagcct tgccgcatca aaggtgacat   2160
tggacagtcc actgatgatg actctgcacc tcttgtccat tgtgtccgcc ttttatctgc   2220
ttcgtttttg ctaacagggg gaaaaaatgt gctggttccg gacagggatg tgagggtcag   2280
cgtgaaggcc ctggccctca gctgtgtggg agcagctgtg gccctccacc cggaatcttt   2340
cttcagcaaa ctctataaag ttcctcttga caccacggaa taccctgagg aacagtatgt   2400
ctcagacatc ttgaactaca tcgatcatgg agacccacag gttcgaggag ccactgccat   2460
tctctgtggg accctcatct gctccatcct cagcaggtcc cgcttccacg tgggagattg   2520
gatgggcacc attagaaccc tcacaggaaa tacattttct ttggcggatt gcattccttt   2580
gctgcggaaa acactgaagg atgagtcttc tgttacttgc aagttagctt gtacagctgt   2640
gaggaactgt gtcatgagtc tctgcagcag cagctacagt gagttaggac tgcagctgat   2700
catcgatgtg ctgactctga ggaacagttc ctattggctg gtgaggacag agcttctgga   2760
aacccttgca gagattgact tcaggctggt gagctttttg gaggcaaaag cagaaaactt   2820
acacagaggg gctcatcatt atacagggct tttaaaactg caagaacgag tgctcaataa   2880
tgttgtcatc catttgcttg gagatgaaga ccccagggtg cgacatgttg ccgcagcatc   2940
actaattagg cttgtcccaa agctgtttta taaatgtgac caaggacaag ctgatccagt   3000
agtggccgtg gcaagagatc aaagcagtgt ttacctgaaa cttctcatgc atgagacgca   3060
gcctccatct catttctccg tcagcacaat aaccagaata tatagaggct ataacctact   3120
accaagcata acagacgtca ctatggaaaa taacctttca agagttattg cagcagtttc   3180
tcatgaacta atcacatcaa ccaccagagc actcacattt ggatgctgtg aagctttgtg   3240
tcttctttcc actgccttcc cagtttgcat ttggagttta ggttggcact gtggagtgcc   3300
tccactgagt gcctcagatg agtctaggaa gagctgtacc gttgggatgg ccacaatgat   3360
tctgaccctg ctctcgtcag cttggttccc attggatctc tcagcccatc aagatgcttt   3420
gattttggcc ggaaacttgc ttgcagccag tgctcccaaa tctctgagaa gttcatgggc   3480
ctctgaagaa gaagccaacc cagcagccac caagcaagag gaggtctggc cagccctggg   3540
ggaccgggcc ctggtgccca tggtggagca gctcttctct cacctgctga aggtgattaa   3600
catttgtgcc cacgtcctgg atgacgtggc tcctggaccc gcaataaagg cagccttgcc   3660
```

-continued

```
ttctctaaca aaccccccttt ctctaagtcc catccgacga aaggggaagg agaaagaacc   3720
aggagaacaa gcatctgtac cgttgagtcc caagaaaggc agtgaggcca gtgcagcttc   3780
tagacaatct gatacctcag gtcctgttac aacaagtaaa tcctcatcac tggggagttt   3840
ctatcatctt ccttcatacc tcaaactgca tgatgtcctg aaagctacac acgctaacta   3900
caaggtcacg ctggatcttc agaacagcac ggaaaagttt ggagggtttc tccgctcagc   3960
cttggatgtt ctttctcaga tactagagct ggccacactg caggacattg ggaagtgtgt   4020
tgaagagatc ctaggatacc tgaaatcctg ctttagtcga gaaccaatga tggcaactgt   4080
ttgtgttcaa caattgttga agactctctt tggcacaaac ttggcctccc agtttgatgg   4140
cttatcttcc aaccccagca agtcacaagg ccgagcacag cgccttggct cctccagtgt   4200
gaggccaggc ttgtaccact actgcttcat ggccccgtac acccacttca cccaggccct   4260
cgctgacgcc agcctgagga acatggtgca ggcggagcag gagaacgaca cctcgggatg   4320
gtttgatgtc ctccagaaag tgtctaccca gttgaagaca aacctcacga gtgtcacaaa   4380
gaaccgtgca gataagaatg ctattcataa tcacattcgt ttgtttgaac ctcttgttat   4440
aaaagcttta aaacagtaca cgactacaac atgtgtgcag ttacagaagc aggttttaga   4500
tttgctggcg cagctggttc agttacgggt taattactgt cttctggatt cagatcaggt   4560
gtttattggc tttgtattga aacagtttga atacattgaa gtgggccagt tcagggaatc   4620
agaggcaatc attccaaaca tctttttctt cttggtatta ctatcttatg aacgctatca   4680
ttcaaaacag atcattggaa ttcctaaaat cattcagctc tgtgatggca tcatggccag   4740
tggaaggaag gctgtgacac atgccatacc ggctctgcag cccatagtcc acgacctctt   4800
tgtattaaga ggaacaaata aagctgatgc aggaaaagag cttgaaaccc aaaaagaggt   4860
ggtggtgtca atgttactga gactcatcca gtaccatcag gtgttggaga tgttcattct   4920
tgtcctgcag cagtgccaca aggagaatga agacaagtgg aagcgactgt ctcgacagat   4980
agctgacatc atcctcccaa tgttagccaa acagcagatg cacattgact ctcatgaagc   5040
ccttggagtg ttaaatacat tatttgagat tttggcccct tcctccctcc gtccggtaga   5100
catgctttta cggagtatgt tcgtcactcc aaacacaatg gcgtccgtga gcactgttca   5160
actgtggata tcgggaattc tggccatttt gagggttctg atttcccagt caactgaaga   5220
tattgttctt tctcgtattc aggagctctc cttctctccg tatttaatct cctgtacagt   5280
aattaatagg ttaagagatg gggacagtac ttcaacgcta gaagaacaca gtgaagggaa   5340
acaaataaag aatttgccag aagaaacatt ttcaaggttt ctattacaac tggttggtat   5400
tcttttagaa gacattgtta caaaacagct gaaggtggaa atgagtgagc agcaacatac   5460
tttctattgc caggaactag gcacactgct aatgtgtctg atccacatct tcaagtctgg   5520
aatgttccgg agaatcacag cagctgccac taggctgttc cgcagtgatg gctgtggcgg   5580
cagtttctac accctggaca gcttgaactt gcgggctcgt tccatgatca ccacccaccc   5640
ggccctggtg ctgctctggt gtcagatact gctgcttgtc aaccacaccg actaccgctg   5700
gtgggcagaa gtgcagcaga ccccgaaaag acacagtctg tccagcacaa agttacttag   5760
tccccagatg tctggagaag aggaggattc tgacttggca gccaaacttg gaatgtgcaa   5820
tagagaaata gtacgaagag ggctctcat tctcttctgt gattatgtct gtcagaacct   5880
ccatgactcc gagcacttaa cgtggctcat tgtaaatcac attcaagatc tgatcagcct   5940
ttcccacgag cctccagtac aggacttcat cagtgccgtt catcggaact ctgctgccag   6000
cggcctgttc atccaggcaa ttcagtctcg ttgtgaaaac ctttcaactc caaccatgct   6060
```

gaagaaaact cttcagtgct tggaggggat ccatctcagc cagtcgggag ctgtgctcac 6120
gctgtatgtg gacaggcttc tgtgcacccc tttccgtgtg ctggctcgca tggtcgacat 6180
ccttgcttgt cgccgggtag aaatgcttct ggctgcaaat ttacagagca gcatggccca 6240
gttgccaatg gaagaactca acagaatcca ggaatacctt cagagcagcg ggctcgctca 6300
gagacaccaa aggctctatt ccctgctgga caggtttcgt ctctccacca tgcaagactc 6360
acttagtccc tctcctccag tctcttccca cccgctggac ggggatgggc acgtgtcact 6420
ggaaacagtg agtccggaca aagactggta cgttcatctt gtcaaatccc agtgttggac 6480
caggtcagat tctgcactgc tggaaggtgc agagctggtg aatcggattc ctgctgaaga 6540
tatgaatgcc ttcatgatga actcggagtt caacctaagc ctgctagctc catgcttaag 6600
cctagggatg agtgaaattt ctggtggcca gaagagtgcc ctttttgaag cagcccgtga 6660
ggtgactctg gcccgtgtga gcggcaccgt gcagcagctc cctgctgtcc atcatgtctt 6720
ccagcccgag ctgcctgcag agccggcggc ctactggagc aagttgaatg atctgtttgg 6780
ggatgctgca ctgtatcagt ccctgcccac tctggcccgg gccctggcac agtacctggt 6840
ggtggtctcc aaactgccca gtcatttgca ccttcctcct gagaaagaga aggacattgt 6900
gaaattcgtg gtggcaaccc ttgaggccct gtcctggcat ttgatccatg agcagatccc 6960
gctgagtctg gatctccagg cagggctgga ctgctgctgc ctggccctgc agctgcctgg 7020
cctctggagc gtggtctcct ccacagagtt tgtgacccac gcctgctccc tcatctactg 7080
tgtgcacttc atcctggagg ccgttgcagt gcagcctgga gagcagcttc ttagtccaga 7140
aagaaggaca aataccccaa aagccatcag cgaggaggag gaggaagtag atccaaacac 7200
acagaatcct aagtatatca ctgcagcctg tgagatggtg gcagaaatgg tggagtctct 7260
gcagtcggtg ttggccttgg gtcataaaag gaatagcggc gtgccggcgt ttctcacgcc 7320
attgctaagg aacatcatca tcagcctggc ccgcctgccc cttgtcaaca gctacacacg 7380
tgtgccccca ctggtgtgga agcttggatg gtcacccaaa ccgggagggg attttggcac 7440
agcattccct gagatccccg tggagttcct ccaggaaaag gaagtcttta aggagttcat 7500
ctaccgcatc aacacactag gctggaccag tcgtactcag tttgaagaaa cttgggccac 7560
cctccttggt gtcctggtga cgcagcccct cgtgatggag caggaggaga gcccaccaga 7620
agaagacaca gagaggaccc agatcaacgt cctggccgtg caggccatca cctcactggt 7680
gctcagtgca atgactgtgc ctgtggccgg caacccagct gtaagctgct tggagcagca 7740
gccccggaac aagcctctga aagctctcga caccaggttt gggaggaagc tgagcattat 7800
cagagggatt gtggagcaag agattcaagc aatggtttca aagagagaga atattgccac 7860
ccatcattta tatcaggcat gggatcctgt cccttctctg tctccggcta ctacaggtgc 7920
cctcatcagc cacgagaagc tgctgctaca gatcaacccc gagcgggagc tggggagcat 7980
gagctacaaa ctcggccagg tgtccataca ctccgtgtgg ctggggaaca gcatcacacc 8040
cctgagggag gaggaatggg acgaggaaga ggaggaggag gccgacgccc ctgcaccttc 8100
gtcaccaccc acgtctccag tcaactccag gaaacaccgg gctggagttg acatccactc 8160
ctgttcgcag tttttgcttg agttgtacag ccgctggatc ctgccgtcca gctcagccag 8220
gaggaccccg gccatcctga tcagtgaggt ggtcagatcc cttctagtgg tctcagactt 8280
gttcaccgag cgcaaccagt ttgagctgat gtatgtgacg ctgacagaac tgcgaagggt 8340
gcacccttca gaagacgaga tcctcgctca gtacctggtg cctgccacct gcaaggcagc 8400

-continued

```
tgccgtcctt gggatggaca aggccgtggc ggagcctgtc agccgcctgc tggagagcac   8460
gctcaggagc agccacctgc ccagcagggt tggagccctg cacggcgtcc tctatgtgct   8520
ggagtgcgac ctgctggacg acactgccaa gcagctcatc ccggtcatca gcgactatct   8580
cctctccaac ctgaaaggga tcgcccactg cgtgaacatt cacagccagc agcacgtact   8640
ggtcatgtgt gccactgcgt tttacctcat tgagaactat cctctggacg tagggccgga   8700
attttcagca tcaataatac agatgtgtgg ggtgatgctg tctggaagtg aggagtccac   8760
cccctccatc atttaccact gtgccctcag aggcctggag cgcctcctgc tctctgagca   8820
gctctcccgc ctggatgcag aatcgctggt caagctgagt gtggacagag tgaacgtgca   8880
cagcccgcac cgggccatgg cggctctggg cctgatgctc acctgcatgt acacaggaaa   8940
ggagaaagtc agtccgggta gaacttcaga ccctaatcct gcagcccccg acagcgagtc   9000
agtgattgtt gctatggagc gggtatctgt tctttttgat aggatcagga aaggctttcc   9060
ttgtgaagcc agagtggtgg ccaggatcct gccccagttt ctagacgact tcttcccacc   9120
ccaggacatc atgaacaaag tcatcggaga gtttctgtcc aaccagcagc catacccccca   9180
gttcatggcc accgtggtgt ataaggtgtt tcagactctg cacagcaccg ggcagtcgtc   9240
catggtccgg gactgggtca tgctgtccct ctccaacttc acgcagaggg ccccggtcgc   9300
catggccacg tggagcctct cctgcttctt tgtcagcgcg tccaccagcc cgtgggtcgc   9360
ggcgatcctc ccacatgtca tcagcaggat gggcaagctg gagcaggtgg acgtgaacct   9420
tttctgcctg gtcgccacag acttctacag acaccagata gaggaggagc tcgaccgcag   9480
ggccttccag tctgtgcttg aggtggttgc agccccagga agcccatatc accggctgct   9540
gacttgttta cgaaatgtcc acaaggtcac cacctgctga gcgccatggt gggagagact   9600
gtgaggcggc agctggggcc ggagcctttg gaagtctgcg cccttgtgcc ctgcctccac   9660
cgagccagct tggtccctat gggcttccgc acatgccgcg ggcggccagg caacgtgcgt   9720
gtctctgcca tgtggcagaa gtgctctttg tggcagtggc caggcaggga gtgtctgcag   9780
tcctggtggg gctgagcctg aggccttcca gaaagcagga gcagctgtgc tgcaccccat   9840
gtgggtgacc aggtcctttc tcctgatagt cacctgctgg ttgttgccag gttgcagctg   9900
ctcttgcatc tgggccagaa gtcctccctc ctgcaggctg gctgttggcc cctctgctgt   9960
cctgcagtag aaggtgccgt gagcaggctt tgggaacact ggcctgggtc tccctggtgg  10020
ggtgtgcatg ccacgccccg tgtctggatg cacagatgcc atggcctgtg ctgggccagt  10080
ggctgggggt gctagacacc cggcaccatt ctcccttctc tcttttcttc tcaggattta  10140
aaatttaatt atatcagtaa agagattaat tttaacgtaa ctctttctat gcccgtgtaa  10200
agtatgtgaa tcgcaaggcc tgtgctgcat gcgacagcgt ccggggtggt ggacagggcc  10260
cccggccacg ctccctctcc tgtagccact ggcatagccc tcctgagcac ccgctgacat  10320
ttccgttgta catgttcctg tttatgcatt cacaaggtga ctgggatgta gagaggcgtt  10380
agtgggcagg tggccacagc aggactgagg acaggccccc attatcctag gggtgcgctc  10440
acctgcagcc cctcctcctc gggcacagac gactgtcgtt ctccacccac cagtcaggga  10500
cagcagcctc cctgtcactc agctgagaag gccagccctc cctggctgtg agcagcctcc  10560
actgtgtcca gagacatggg cctcccactc ctgttccttg ctagccctgg ggtggcgtct  10620
gcctaggagc tggctggcag gtgttgggac ctgctgctcc atggatgcat gccctaagag  10680
tgtcactgag ctgtgttttg tctgagcctc tctcggtcaa cagcaaagct tggtgtcttg  10740
gcactgttag tgacagagcc cagcatccct tctgccccgg ttccagctga catcttgcac  10800
```

-continued

```
ggtgacccct tttagtcagg agagtgcaga tctgtgctca tcggagactg ccccacggcc  10860
ctgtcagagc cgccactcct atccccaggc caggtccctg gaccagcctc ctgtttgcag  10920
gcccagagga gccaagtcat taaaatggaa gtggattctg gatggccggg ctgctgctga  10980
tgtaggagct ggatttggga gctctgcttg ccgactggct gtgagacgag gcaggggctc  11040
tgcttcctca gccctagagg cgagccaggc aaggttggcg actgtcatgt ggcttggttt  11100
ggtcatgccc gtcgatgttt tgggtattga atgtggtaag tggaggaaat gttggaactc  11160
tgtgcaggtg ctgccttgag acccccaagc ttccacctgt ccctctccta tgtggcagct  11220
ggggagcagc tgagatgtgg acttgtatgc tgcccacata cgtgaggggg agctgaaagg  11280
gagcccctcc tctgagcagc ctctgccagg cctgtatgag gcttttccca ccagctccca  11340
acagaggcct cccccagcca ggaccacctc gtcctcgtgg cggggcagca ggagcggtag  11400
aaaggggtcc gatgtttgag gaggccctta agggaagcta ctgaattata acacgtaaga  11460
aaatcaccat tccgtattgg ttgggggctc ctgtttctca tcctagcttt ttcctggaaa  11520
gcccgctaga aggtttggga acgaggggaa agttctcaga actgttggct gctccccacc  11580
cgcctcccgc ctcccccgca ggttatgtca gcagctctga gacagcagta tcacaggcca  11640
gatgttgttc ctggctagat gtttacattt gtaagaaata acactgtgaa tgtaaaacag  11700
agccattccc ttggaatgca tatcgctggg ctcaacatag agtttgtctt cctcttgttt  11760
acgacgtgat ctaaaccagt ccttagcaag gggctcagaa caccccgctc tggcagtagg  11820
tgtcccccac ccccaaagac ctgcctgtgt gctccggaga tgaatatgag ctcattagta  11880
aaaatgactt cacccacgca tatacataaa gtatccatgc atgtgcatat agacacatct  11940
ataattttac acacacacct ctcaagacgg agatgcatgg cctctaagag tgcccgtgtc  12000
ggttcttcct ggaagttgac tttccttaga cccgccaggt caagttagcc gcgtgacgga  12060
catccaggcg tgggacgtgg tcagggcagg gctcattcat tgcccactag gatcccactg  12120
gcgaagatgg tctccatatc agctctctgc agaagggagg aagactttat catgttccta  12180
aaaatctgtg gcaagcaccc atcgtattat ccaaattttg ttgcaaatgt gattaatttg  12240
gttgtcaagt tttgggggtg ggctgtgggg agattgcttt tgttttcctg ctggtaatat  12300
cgggaaagat tttaatgaaa ccagggtaga attgtttggc aatgcactga agcgtgtttc  12360
tttcccaaaa tgtgcctccc ttccgctgcg ggcccagctg agtctatgta ggtgatgttt  12420
ccagctgcca agtgctcttt gttactgtcc accctcattt ctgccagcgc atgtgtcctt  12480
tcaaggggaa aatgtgaagc tgaacccccct ccagacaccc agaatgtagc atctgagaag  12540
gccctgtgcc ctaaaggaca cccctcgccc ccatcttcat ggagggggtc atttcagagc  12600
cctcggagcc aatgaacagc tcctcctctt ggagctgaga tgagccccac gtggagctcg  12660
ggacggatag tagacagcaa taactcggtg tgtggccgcc tggcaggtgg aacttcctcc  12720
cgttgcgggg tggagtgagg ttagttctgt gtgtctggtg ggtggagtca ggcttctctt  12780
gctacctgtg agcatccttc ccagcagaca tcctcatcgg gctttgtccc tcccccgctt  12840
cctccctctg cggggaggac ccgggaccac agctgctggc cagggtagac ttggagctgt  12900
cctccagagg ggtcacgtgt aggagtgaga agaaggaaga tcttgagagc tgctgaggga  12960
ccttggagag ctcaggatgg ctcagacgag gacactcgct tgccgggcct gggcctcctg  13020
ggaaggaggg agctgctcag aatgccgcat gacaactgaa ggcaacctgg aaggttcagg  13080
ggccgctctt cccccatgtg cctgtcacgc tctggtgcag tcaaaggaac gccttcccct  13140
```

-continued cagttgtttc taagagcaga gtctcccgct gcaatctggg tggtaactgc cagccttgga 13200
ggatcgtggc caacgtggac ctgcctacgg agggtgggct ctgacccaag tggggcctcc 13260
ttgtccaggt ctcactgctt tgcaccgtgg tcagagggac tgtcagctga gcttgagctc 13320
ccctggagcc agcagggctg tgatgggcga gtcccggagc cccacccaga cctgaatgct 13380
tctgagagca aagggaagga ctgacgagag atgtatattt aattttttaa ctgctgcaaa 13440
cattgtacat ccaaattaaa ggaaaaaaat ggaaaccatc a 13481

<210> SEQ ID NO 3
<211> LENGTH: 17
<212> TYPE: PRT
<213> ORGANISM: Homo sapiens
<220> FEATURE:
<221> NAME/KEY: Misc_feature
<222> LOCATION: (2)..(2)
<223> OTHER INFORMATION: Lys is acetylated

<400> SEQUENCE: 3

Lys Val Leu Leu Gly Glu Glu Glu Ala Leu Glu Asp Asp Ser Glu Ser
1 5 10 15

Arg

<210> SEQ ID NO 4
<211> LENGTH: 17
<212> TYPE: PRT
<213> ORGANISM: Homo sapiens

<400> SEQUENCE: 4

Cys Ser Pro Val Leu Ser Arg Lys Gln Lys Gly Lys Val Leu Leu Gly
1 5 10 15

Glu

<210> SEQ ID NO 5
<211> LENGTH: 17
<212> TYPE: PRT
<213> ORGANISM: Mus musculus

<400> SEQUENCE: 5

Cys Ser Pro Val Leu Ser Arg Lys Gln Lys Gly Lys Val Leu Leu Gly
1 5 10 15

Glu

<210> SEQ ID NO 6
<211> LENGTH: 17
<212> TYPE: PRT
<213> ORGANISM: Rat rattus

<400> SEQUENCE: 6

Cys Ser Pro Val Leu Ser Arg Lys Gln Lys Gly Lys Val Leu Leu Gly
1 5 10 15

Glu

<210> SEQ ID NO 7
<211> LENGTH: 17
<212> TYPE: PRT
<213> ORGANISM: Danio rerio

<400> SEQUENCE: 7

Cys Ser Pro Leu Leu Leu Arg Lys Gln Lys Gly Lys Leu Leu Ser Gly
1 5 10 15

Glu

<210> SEQ ID NO 8
<211> LENGTH: 17
<212> TYPE: PRT
<213> ORGANISM: Fugu rubripes

<400> SEQUENCE: 8

Cys Ser Pro Leu Leu His Arg Lys His Arg Gly Lys Met Leu Ser Gly
1 5 10 15

Glu

<210> SEQ ID NO 9
<211> LENGTH: 18
<212> TYPE: PRT
<213> ORGANISM: Homo sapiens

<400> SEQUENCE: 9

Arg Arg Val Tyr Ile Ser Tyr Leu Asp Ser Ile His Phe Phe Arg Pro
1 5 10 15

Arg Cys

<210> SEQ ID NO 10
<211> LENGTH: 18
<212> TYPE: PRT
<213> ORGANISM: Homo sapiens

<400> SEQUENCE: 10

Arg Arg Val Tyr Ile Ser Tyr Leu Asp Ser Val His Phe Phe Arg Pro
1 5 10 15

Lys Cys

<210> SEQ ID NO 11
<211> LENGTH: 10081
<212> TYPE: DNA
<213> ORGANISM: Mus musculus

<400> SEQUENCE: 11
gcactcgccg cgagggttgc cgggacgggc ccaagatggc tgagcgcctt ggttccgctt 60
ctgcctgccg cgcagagccc cattcattgc cttgctgcta agtggcgccg cgtagtgcca 120
gtaggctcca agtcttcagg gtctgtccca tcgggcagga agccgtcatg gcaaccctgg 180
aaaagctgat gaaggctttc gagtcgctca agtcgtttca gcagcaacag cagcagcagc 240
caccgccgca ggcgccgccg ccaccgccgc cgccgcctcc gcctcaaccc cctcagccgc 300
cgcctcaggg gcagccgccg ccgccaccac cgccgctgcc aggtccggca gaggaaccgc 360
tgcaccgacc aaagaaggaa ctctcagcca ccaagaaaga ccgtgtgaat cattgtctaa 420
caatatgtga aaacattgtg gcacagtctc tcagaaattc tccagaattt cagaaactct 480
tgggcatcgc tatggaactg tttctgctgt gcagtgacga tgcggagtca gatgtcagaa 540
tggtggctga tgagtgcctc aacaaagtca tcaaagcttt gatggattct aatcttccaa 600
ggctacagtt agaactctat aaggaaatta aaaagaatgg tgctcctcga agtttgcgtg 660
ctgccctgtg gaggtttgct gagctggctc acctggttcg acctcagaag tgcaggcctt 720
acctggtgaa tcttcttcca tgcctgaccc gaacaagcaa aagaccggag gaatcagttc 780
aggagacctt ggctgcagct gttcctaaaa ttatggcttc ttttggcaat ttcgcaaatg 840
acaatgaaat taaggttctg ttgaaagctt tcatagcaaa tctgaagtca agctctccca 900

-continued

```
ccgtgcggcg gacagcagcc ggctcagccg tgagcatctg ccaacattct aggaggacac    960
agtacttcta caactggctc cttaatgtcc tcctaggtct gctggttccc atggaagaag   1020
agcactccac tctcctgatc ctcggtgtgt tgctcacatt gaggtgtcta gtgcccttgc   1080
tccagcagca ggtcaaggac acaagtctaa aaggcagctt tggggtgaca cggaaagaaa   1140
tggaagtctc tccttctaca gagcagcttg tccaggttta tgaactgact ttgcatcata   1200
ctcagcacca agaccacaat gtggtgacag gggcactgga gctcctgcag cagctcttcc   1260
gtacccctcc acctgaactc ctgcaagcac tgaccacacc aggagggctt gggcagctca   1320
ctctggttca agaagaggcc cggggccgag gccgcagcgg gagcatcgtg gagcttttag   1380
ctggaggggg ttcctcgtgc agccctgtcc tctcaagaaa gcagaaaggc aaagtgctct   1440
taggagagga agaagccttg gaagatgact cggagtccag gtcagatgtc agcagctcag   1500
cctttgcagc ctctgtgaag agtgagattg gtggagagct cgctgcttct tcaggtgttt   1560
ccactcctgg ttctgttggt cacgacatca tcactgagca gcctagatcc cagcacacac   1620
ttcaagcaga ctctgtggat ttgtccggct gtgacctgac cagtgctgct actgatgggg   1680
atgaggagga catcttgagc cacagctcca gccagttcag tgctgtccca tccgaccctg   1740
ccatggacct gaatgatggg acccaggcct cctcacccat cagtgacagt tctcagacca   1800
ccactgaagg acctgattca gctgtgactc cttcggacag ttctgaaatt gtgttagatg   1860
gtgccgatag ccagtattta ggcatgcaga taggacagcc acaggaggac gatgaggagg   1920
gagctgcagg tgttctttct ggtgaagtct cagatgtttt cagaaactct tctctggccc   1980
ttcaacaggc acacttgttg gaaagaatgg gccatagcag gcagccttcc gacagcagta   2040
tagataagta tgtaacaaga gatgaggttg ctgaagccag tgatccagaa agcaagcctt   2100
gccgaatcaa aggtgacata ggacagccta atgatgatga ttctgctcct ctggtacatt   2160
gtgtccgtct tttatctgct tcctttttgt taactggtga aaagaaagca ctggttccag   2220
acagagacgt gagagtcagt gtgaaggccc tggccctcag ctgcattggt gcggctgtgg   2280
cccttcatcc agagtcgttc ttcagcagac tgtacaaagt acctcttaat accacggaaa   2340
gtactgagga acagtatgtt tctgacatct tgaactacat cgatcatgga gacccacagg   2400
tccgaggagc tactgccatt ctctgtggga cccttgtcta ctccatcctc agtaggtccc   2460
gtctccgtgt tggtgactgg ctgggcaaca tcagaaccct gacaggaaat acattttctc   2520
tggtggactg cattccttta ctgcagaaaa cgttgaagga tgaatcttct gttacttgca   2580
agttggcttg tacagctgtg aggcactgtg tcctgagtct ttgcagcagc agctacagtg   2640
acttgggatt acaactgctt attgatatgc tgcctctgaa gaacagctcc tactggctgg   2700
tgaggaccga actgctggac actctggcag agattgactt caggctcgtg agtttttttgg   2760
aggcaaaagc agaaagttta caccgagggg ctcatcatta tacagggttt ctaaaactac   2820
aagaacgagt actcaataat gtggtcattt atttgcttgg agatgaagac cccagggttc   2880
gacatgttgc tgcaacatca ttaacaaggc ttgtcccaaa gctgttttac aagtgtgacc   2940
aaggacaagc tgatccagtt gtggctgtag cgagggatca gagcagtgtc tacctgaagc   3000
tcctcatgca tgagacccag ccaccatcac acttttctgt cagcaccatc accagaatct   3060
atagaggcta tagcttactg ccaagtataa cagatgtcac catggaaaac aatctctcaa   3120
gagttgttgc cgcagtttct catgaactca ttacgtcaac aacacgggca ctcacatttg   3180
gatgctgtga agccttgtgt cttctctcag cagcctttcc agtttgcact tggagtttag   3240
gatggcactg tggagtgccc ccactgagtg cctctgatga gtccaggaag agctgcactg   3300
```

-continued

```
ttgggatggc ctccatgatt ctcaccttgc tttcatcagc ttggttccca ctggatctct   3360
cagcccatca ggatgccttg attttggctg gaaacttgct agcagcgagt gcccccaagt   3420
ctctgagaag ttcatggacc tctgaagaag aagccaactc agcagccacc agacaggagg   3480
aaatctggcc tgctctgggg gatcggactc tagtgccctt ggtggagcag cttttctccc   3540
acctgctgaa ggtgatcaat atctgtgctc atgtcttgga cgatgtgact cctggaccag   3600
caatcaaggc agccttgcct tctctaacaa accccccttc tctaagtcct attcgacgga   3660
aagggaagga gaaagaacct ggagaacaag cttctactcc aatgagtccc aagaaagttg   3720
gtgaggccag tgcagcctct cgacaatcag acacctcagg acctgtcaca gcaagtaaat   3780
catcctcact ggggagtttc taccatctcc cctcctacct caaactgcat gatgtcctga   3840
aagccactca cgccaactat aaggtcacct tagatcttca gaacagcact gaaaagtttg   3900
gggggttcct gcgctctgcc ttggacgtcc tttctcagat tctagagctg gcgacactgc   3960
aggacattgg aaagtgtgtt gaagaggtcc ttggatacct gaaatcctgc tttagtcgag   4020
aaccaatgat ggcaactgtc tgtgtgcagc agctattgaa gactctcttt gggacaaact   4080
tagcctcaca gtttgatggc ttatcttcca accccagcaa gtctcagtgc cgagctcagc   4140
gccttggctc ttcaagtgtg aggcccggct tatatcacta ctgcttcatg gcaccataca   4200
cgcacttcac acaggccttg gctgacgcaa gcctgaggaa catggtgcag gcggagcagg   4260
agcgtgatgc ctcggggtgg tttgatgtac tccagaaagt gtctgcccaa ttgaagacga   4320
acctaacaag cgtcacaaag aaccgtgcag ataagaatgc tattcataat cacattaggt   4380
tatttgagcc tcttgttata aaagcattga agcagtacac cacgacaaca tctgtacaat   4440
tgcagaagca ggttttggat ttgctggcac agctggttca gctacgggtc aattactgtc   4500
tactggattc agaccaggtg ttcatcgggt ttgtgctgaa gcagtttgag tacattgaag   4560
tgggccagtt cagggaatca gaggcaatta ttccaaatat atttttcttc ctggtattac   4620
tgtcttatga gcgctaccat tcaaaacaga tcattggaat tcctaaaatc atccagctgt   4680
gtgatggcat catggccagt ggaaggaagg ccgttacaca tgctatacct gctctgcagc   4740
ccattgtcca tgacctcttt gtgttacgag gaacaaataa agctgatgca gggaaagagc   4800
ttgagacaca gaaggaggtg gtggtctcca tgctgttacg actcatccag taccatcagg   4860
tgctggagat gttcatcctt gtcctgcagc agtgccacaa ggagaatgag gacaagtgga   4920
aacggctctc tcggcaggtc gcagacatca tcctgcccat gttggccaag cagcagatgc   4980
atattgactc tcatgaagcc cttggagtgt taaatacctt gtttgagatt ttggctcctt   5040
cctccctacg tcctgtggac atgcttttgc ggagtatgtt catcactcca agcacaatgg   5100
catctgtaag cactgtgcag ctgtggatat ctggaatcct cgccattctg agggttctca   5160
tttcccagtc aaccgaggac attgttcttt gtcgtattca ggagctctcc ttctctccac   5220
acttgctctc ctgtccagtg attaacaggt taaggggtgg aggcggtaat gtaacactag   5280
gagaatgcag cgaagggaaa caaaagagtt tgccagaaga tacattctca aggtttcttt   5340
tacagctggt tggtattctt ctagaagaca tcgttacaaa acagctcaaa gtggacatga   5400
gtgaacagca gcatacgttc tactgccaag agctaggcac actgctcatg tgtctgatcc   5460
acatattcaa atctggaatg ttccggagaa tcacagcagc tgccactaga ctcttcacca   5520
gtgatggctg tgaaggcagc ttctatactc tagagagcct gaatgcacgg gtccgatcca   5580
tggtgcccac gcacccagcc ctggtactgc tctggtgtca gatcctactt ctcatcaacc   5640
```

-continued

```
acactgacca ccggtggtgg gcagaggtgc agcagacacc caagagacac agtctgtcct   5700
gcacgaagtc acttaacccc cagaagtctg gcgaagagga ggattctggc tcggcagctc   5760
agctgggaat gtgcaataga gaaatagtgc gaagaggggc ccttattctc ttctgtgatt   5820
atgtctgtca gaatctccat gactcagaac acttaacatg gctcattgtg aatcacattc   5880
aagatctgat cagcttgtct catgagcctc cagtacaaga ctttattagt gccattcatc   5940
gtaattctgc agctagtggt ctttttatcc aggcaattca gtctcgctgt gaaaatcttt   6000
caacgccaac cactctgaag aaaacacttc agtgcttgga aggcatccat ctcagccagt   6060
ctggtgctgt gctcacacta tatgtggaca ggctcctggg cacccccttc cgtgcgctgg   6120
ctcgcatggt cgacaccctg gcctgtcgcc gggtagaaat gcttttggct gcaaatttac   6180
agagcagcat ggcccagttg ccagaggagg aactaaacag aatccaagaa cacctccaga   6240
acagtgggct tgcacaaaga caccaaaggc tctattcact gctggacaga ttccgactct   6300
ctactgtgca ggactcactt agccccttgc cccagtcac ttcccaccca ctggatgggg   6360
atgggcacac atctctggaa acagtgagtc cagacaaaga ctggtacctc cagcttgtca   6420
gatcccagtg ttggaccaga tcagattctg cactgctgga aggtgcagag ctggtcaacc   6480
gtatccctgc tgaagatatg aatgacttca tgatgagctc ggagttcaac ctaagccttt   6540
tggctccctg tttaagcctt ggcatgagcg agattgctaa tggccaaaag agtcccctct   6600
ttgaagcagc ccgtggggtg attctgaacc gggtgaccag tgttgttcag cagcttcctg   6660
ctgtccatca agtcttccag cccttcctgc ctatagagcc cacggcctac tggaacaagt   6720
tgaatgatct gcttggtgat accacatcat accagtctct gaccatactt gcccgtgccc   6780
tggcacagta cctggtggtg ctctccaaag tgcctgctca tttgcacctt cctcctgaga   6840
aggaggggga cacggtgaag tttgtggtaa tgacagttga ggccctgtca tggcatttga   6900
tccatgagca gatcccactg agtctggacc tccaagccgg gctagactgc tgctgcctgg   6960
cactacaggt gcctggcctc tggggggtgc tgtcctcccc agagtacgtg actcatgcct   7020
gctccctcat ccattgtgtg cgattcatcc tggaagccat tgcagtacaa cctggagacc   7080
agcttctcgg tcctgaaagc aggtcacata ctccaagagc tgtcagaaag gaggaagtag   7140
actcagatat acaaaacctc agtcatgtca cttcggcctg cgagatggtg gcagacatgg   7200
tggaatccct gcagtcagtg ctggccttgg gccacaagag gaacagcacc ctgccttcat   7260
ttctcacagc tgtgctgaag aacattgtta tcagtctggc ccgactcccc ctagttaaca   7320
gctatactcg tgtgcctcct ctggtatgga aactcgggtg gtcacccaag cctggagggg   7380
attttggcac agtgtttcct gagatccctg tagagttcct ccaggagaag gagatcctca   7440
aggagttcat ctaccgcatc aacaccctag ggtggaccaa tcgtacccag ttcgaagaaa   7500
cttgggccac cctccttggt gtcctggtga ctcagcccct ggtgatggaa caggaagaga   7560
gcccaccaga ggaagacaca gaaagaaccc agatccatgt cctggctgtg caggccatca   7620
cctctctagt gctcagtgca atgaccgtgc ctgtggctgg caatccagct gtaagctgct   7680
tggagcaaca gccccggaac aagccactga aggctctcga taccagattt ggaagaaagc   7740
tgagcatgat cagagggatt gtagaacaag aaatccaaga gatggtttcc cagagagaga   7800
atactgccac tcaccattct caccaggcgt gggatcctgt cccttctctg ttaccagcta   7860
ctacaggtgc tcttatcagc catgacaagc tgctgctgca gatcaaccca gagcgggagc   7920
caggcaacat gagctacaag ctgggccagg tgtccataca ctccgtgtgg ctgggaaata   7980
acatcacacc cctgagagag gaggaatggg atgaggaaga agaggaagaa agtgatgtcc   8040
```

ctgcaccaac gtcaccacct gtgtctccag tcaattccag aaaacaccgt gccggggttg 8100
atattcactc ctgttcgcag tttctgcttg aattgtacag ccgatggatc ctgccatcca 8160
gtgcagccag aaggaccccc gtcatcctga tcagtgaagt ggttcgatct cttcttgtag 8220
tgtcagactt attcaccgaa cgtacccagt ttgaaatgat gtatctgacg ctgacagaac 8280
tacggagagt gcacccttca gaagatgaga tcctcattca gtacctggtg cctgccacct 8340
gtaaggcagc tgctgtcctt ggaatggaca aaactgtggc agagccagtc agccgcctac 8400
tggagagcac actgaggagc agccacctgc ccagccagat cggagccctg cacggcatcc 8460
tctatgtgtt ggagtgtgac ctcttggatg acactgcaaa gcagctcatt ccagttgtta 8520
gtgactatct gctgtccaac ctcaaaggaa tagcccactg cgtgaacatt cacagccagc 8580
agcatgtgct ggtaatgtgt gccactgctt tctacctgat ggaaaactac cctctggatg 8640
tgggaccaga attttcagca tctgtgatac agatgtgtgg agtaatgctg tctggaagtg 8700
aggagtccac cccctccatc atttaccact gtgccctccg gggtctggag cggctcctgc 8760
tgtctgagca gctatctcgg ctagacacag agtccttggt caagctaagt gtggacagag 8820
tgaatgtaca aagcccacac agggccatgg cagccctagg cctgatgctc acctgcatgt 8880
acacaggaaa ggaaaaagcc agtccaggca gagcttctga ccccagccct gctacacctg 8940
acagcgagtc tgtgattgta gctatggagc gagtgtctgt tctctttgat aggatccgca 9000
agggatttcc ctgtgaagcc agggttgtgg caaggatcct gcctcagttc ctagatgact 9060
tctttccacc tcaagatgtc atgaacaaag tcattggaga gttcctgtcc aatcagcagc 9120
catacccaca gttcatggcc actgtagttt acaaggtttt tcagactctg cacagtgctg 9180
ggcagtcatc catggtccgg gactgggtca tgctgtccct gtccaacttc acacaaagaa 9240
ctccagttgc catggccatg tggagcctct cctgcttcct tgttagcgca tctaccagcc 9300
catgggtttc tgcgatcctt ccacatgtca tcagcaggat gggcaaactg gaacaggtgg 9360
atgtgaacct tttctgcctg gttgccacag acttctacag acaccagata gaggaggaat 9420
tcgaccgcag ggctttccag tctgtgtttg aggtggtggc tgcaccagga agtccatacc 9480
acaggctgct tgcttgtttg caaaatgttc acaaggtcac cacctgctga gtagtgcctg 9540
tgggacaaaa ggctgaaaga aggcagctgc tggggcctga gcctccagga gcctgctcca 9600
agcttctgct ggggctgcct tggccgtgca ggcttccact tgtgtcaagt ggacagccag 9660
gcaatggcag gagtgctttg caatgagggc tatgcaggga acatgcacta tgttggggtt 9720
gagcctgagt cctgggtcct ggcctcgctg cagctggtga cagtgctagg ttgaccaggt 9780
gtttgtcttt ttcctagtgt tcccctggcc atagtcgcca ggttgcagct gccctggtat 9840
gtggatcaga agtcctagct cttgccagat ggttctgagc ccgcctgctc cactgggctg 9900
gagagctccc tcccacattt acccagtagg catacctgcc acaccagtgt ctggacacaa 9960
aatgaatggt gtgtggggct gggaactggg gctgccaggt gtccagcacc attttccttt 10020
ctgtgttttc ttctcaggag ttaaaattta attatatcag taaagagatt aattttaatg 10080
t 10081

<210> SEQ ID NO 12
<211> LENGTH: 3144
<212> TYPE: PRT
<213> ORGANISM: Homo sapiens
<220> FEATURE:
<221> NAME/KEY: Misc_feature
<222> LOCATION: (444)..(444)

-continued

<223> OTHER INFORMATION: Lys is acetylated

<400> SEQUENCE: 12

```
Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln Gln Gln
            20                  25                  30

Gln Gln Gln Gln Gln Gln Gln Gln Pro Pro Pro Pro Pro Pro Pro Pro
        35                  40                  45

Pro Pro Pro Gln Leu Pro Gln Pro Pro Pro Gln Ala Gln Pro Leu Leu
    50                  55                  60

Pro Gln Pro Gln Pro Pro Pro Pro Pro Pro Pro Pro Pro Pro Gly Pro
65                  70                  75                  80

Ala Val Ala Glu Glu Pro Leu His Arg Pro Lys Lys Glu Leu Ser Ala
                85                  90                  95

Thr Lys Lys Asp Arg Val Asn His Cys Leu Thr Ile Cys Glu Asn Ile
            100                 105                 110

Val Ala Gln Ser Val Arg Asn Ser Pro Glu Phe Gln Lys Leu Leu Gly
        115                 120                 125

Ile Ala Met Glu Leu Phe Leu Leu Cys Ser Asp Asp Ala Glu Ser Asp
    130                 135                 140

Val Arg Met Val Ala Asp Glu Cys Leu Asn Lys Val Ile Lys Ala Leu
145                 150                 155                 160

Met Asp Ser Asn Leu Pro Arg Leu Gln Leu Glu Leu Tyr Lys Glu Ile
                165                 170                 175

Lys Lys Asn Gly Ala Pro Arg Ser Leu Arg Ala Ala Leu Trp Arg Phe
            180                 185                 190

Ala Glu Leu Ala His Leu Val Arg Pro Gln Lys Cys Arg Pro Tyr Leu
        195                 200                 205

Val Asn Leu Leu Pro Cys Leu Thr Arg Thr Ser Lys Arg Pro Glu Glu
    210                 215                 220

Ser Val Gln Glu Thr Leu Ala Ala Ala Val Pro Lys Ile Met Ala Ser
225                 230                 235                 240

Phe Gly Asn Phe Ala Asn Asp Asn Glu Ile Lys Val Leu Leu Lys Ala
                245                 250                 255

Phe Ile Ala Asn Leu Lys Ser Ser Ser Pro Thr Ile Arg Arg Thr Ala
            260                 265                 270

Ala Gly Ser Ala Val Ser Ile Cys Gln His Ser Arg Arg Thr Gln Tyr
        275                 280                 285

Phe Tyr Ser Trp Leu Leu Asn Val Leu Leu Gly Leu Leu Val Pro Val
    290                 295                 300

Glu Asp Glu His Ser Thr Leu Leu Ile Leu Gly Val Leu Leu Thr Leu
305                 310                 315                 320

Arg Tyr Leu Val Pro Leu Leu Gln Gln Gln Val Lys Asp Thr Ser Leu
                325                 330                 335

Lys Gly Ser Phe Gly Val Thr Arg Lys Glu Met Glu Val Ser Pro Ser
            340                 345                 350

Ala Glu Gln Leu Val Gln Val Tyr Glu Leu Thr Leu His His Thr Gln
        355                 360                 365

His Gln Asp His Asn Val Val Thr Gly Ala Leu Glu Leu Leu Gln Gln
    370                 375                 380

Leu Phe Arg Thr Pro Pro Pro Glu Leu Leu Gln Thr Leu Thr Ala Val
385                 390                 395                 400
```

-continued

Gly Gly Ile Gly Gln Leu Thr Ala Ala Lys Glu Glu Ser Gly Gly Arg
405 410 415

Ser Arg Ser Gly Ser Ile Val Glu Leu Ile Ala Gly Gly Gly Ser Ser
420 425 430

Cys Ser Pro Val Leu Ser Arg Lys Gln Lys Gly Lys Val Leu Leu Gly
435 440 445

Glu Glu Glu Ala Leu Glu Asp Asp Ser Glu Ser Arg Ser Asp Val Ser
450 455 460

Ser Ser Ala Leu Thr Ala Ser Val Lys Asp Glu Ile Ser Gly Glu Leu
465 470 475 480

Ala Ala Ser Ser Gly Val Ser Thr Pro Gly Ser Ala Gly His Asp Ile
485 490 495

Ile Thr Glu Gln Pro Arg Ser Gln His Thr Leu Gln Ala Asp Ser Val
500 505 510

Asp Leu Ala Ser Cys Asp Leu Thr Ser Ser Ala Thr Asp Gly Asp Glu
515 520 525

Glu Asp Ile Leu Ser His Ser Ser Ser Gln Val Ser Ala Val Pro Ser
530 535 540

Asp Pro Ala Met Asp Leu Asn Asp Gly Thr Gln Ala Ser Ser Pro Ile
545 550 555 560

Ser Asp Ser Ser Gln Thr Thr Thr Glu Gly Pro Asp Ser Ala Val Thr
565 570 575

Pro Ser Asp Ser Ser Glu Ile Val Leu Asp Gly Thr Asp Asn Gln Tyr
580 585 590

Leu Gly Leu Gln Ile Gly Gln Pro Gln Asp Glu Asp Glu Glu Ala Thr
595 600 605

Gly Ile Leu Pro Asp Glu Ala Ser Glu Ala Phe Arg Asn Ser Ser Met
610 615 620

Ala Leu Gln Gln Ala His Leu Leu Lys Asn Met Ser His Cys Arg Gln
625 630 635 640

Pro Ser Asp Ser Ser Val Asp Lys Phe Val Leu Arg Asp Glu Ala Thr
645 650 655

Glu Pro Gly Asp Gln Glu Asn Lys Pro Cys Arg Ile Lys Gly Asp Ile
660 665 670

Gly Gln Ser Thr Asp Asp Asp Ser Ala Pro Leu Val His Cys Val Arg
675 680 685

Leu Leu Ser Ala Ser Phe Leu Leu Thr Gly Gly Lys Asn Val Leu Val
690 695 700

Pro Asp Arg Asp Val Arg Val Ser Val Lys Ala Leu Ala Leu Ser Cys
705 710 715 720

Val Gly Ala Ala Val Ala Leu His Pro Glu Ser Phe Phe Ser Lys Leu
725 730 735

Tyr Lys Val Pro Leu Asp Thr Thr Glu Tyr Pro Glu Glu Gln Tyr Val
740 745 750

Ser Asp Ile Leu Asn Tyr Ile Asp His Gly Asp Pro Gln Val Arg Gly
755 760 765

Ala Thr Ala Ile Leu Cys Gly Thr Leu Ile Cys Ser Ile Leu Ser Arg
770 775 780

Ser Arg Phe His Val Gly Asp Trp Met Gly Thr Ile Arg Thr Leu Thr
785 790 795 800

Gly Asn Thr Phe Ser Leu Ala Asp Cys Ile Pro Leu Leu Arg Lys Thr
805 810 815

Leu Lys Asp Glu Ser Ser Val Thr Cys Lys Leu Ala Cys Thr Ala Val

```
            820                 825                 830

Arg Asn Cys Val Met Ser Leu Cys Ser Ser Ser Tyr Ser Glu Leu Gly
        835                 840                 845

Leu Gln Leu Ile Ile Asp Val Leu Thr Leu Arg Asn Ser Ser Tyr Trp
    850                 855                 860

Leu Val Arg Thr Glu Leu Leu Glu Thr Leu Ala Glu Ile Asp Phe Arg
865                 870                 875                 880

Leu Val Ser Phe Leu Glu Ala Lys Ala Glu Asn Leu His Arg Gly Ala
                885                 890                 895

His His Tyr Thr Gly Leu Leu Lys Leu Gln Glu Arg Val Leu Asn Asn
            900                 905                 910

Val Val Ile His Leu Leu Gly Asp Glu Asp Pro Arg Val Arg His Val
        915                 920                 925

Ala Ala Ala Ser Leu Ile Arg Leu Val Pro Lys Leu Phe Tyr Lys Cys
    930                 935                 940

Asp Gln Gly Gln Ala Asp Pro Val Val Ala Val Ala Arg Asp Gln Ser
945                 950                 955                 960

Ser Val Tyr Leu Lys Leu Leu Met His Glu Thr Gln Pro Pro Ser His
                965                 970                 975

Phe Ser Val Ser Thr Ile Thr Arg Ile Tyr Arg Gly Tyr Asn Leu Leu
            980                 985                 990

Pro Ser Ile Thr Asp Val Thr Met  Glu Asn Asn Leu Ser  Arg Val Ile
        995                 1000                1005

Ala Ala  Val Ser His Glu Leu  Ile Thr Ser Thr Thr  Arg Ala Leu
    1010                1015                1020

Thr Phe  Gly Cys Cys Glu Ala  Leu Cys Leu Leu Ser  Thr Ala Phe
    1025                1030                1035

Pro Val  Cys Ile Trp Ser Leu  Gly Trp His Cys Gly  Val Pro Pro
    1040                1045                1050

Leu Ser  Ala Ser Asp Glu Ser  Arg Lys Ser Cys Thr  Val Gly Met
    1055                1060                1065

Ala Thr  Met Ile Leu Thr Leu  Leu Ser Ser Ala Trp  Phe Pro Leu
    1070                1075                1080

Asp Leu  Ser Ala His Gln Asp  Ala Leu Ile Leu Ala  Gly Asn Leu
    1085                1090                1095

Leu Ala  Ala Ser Ala Pro Lys  Ser Leu Arg Ser Ser  Trp Ala Ser
    1100                1105                1110

Glu Glu  Glu Ala Asn Pro Ala  Ala Thr Lys Gln Glu  Glu Val Trp
    1115                1120                1125

Pro Ala  Leu Gly Asp Arg Ala  Leu Val Pro Met Val  Glu Gln Leu
    1130                1135                1140

Phe Ser  His Leu Leu Lys Val  Ile Asn Ile Cys Ala  His Val Leu
    1145                1150                1155

Asp Asp  Val Ala Pro Gly Pro  Ala Ile Lys Ala Ala  Leu Pro Ser
    1160                1165                1170

Leu Thr  Asn Pro Pro Ser Leu  Ser Pro Ile Arg Arg  Lys Gly Lys
    1175                1180                1185

Glu Lys  Glu Pro Gly Glu Gln  Ala Ser Val Pro Leu  Ser Pro Lys
    1190                1195                1200

Lys Gly  Ser Glu Ala Ser Ala  Ala Ser Arg Gln Ser  Asp Thr Ser
    1205                1210                1215

Gly Pro  Val Thr Thr Ser Lys  Ser Ser Ser Leu Gly  Ser Phe Tyr
    1220                1225                1230
```

-continued

```
His Leu  Pro Ser Tyr Leu Lys  Leu His Asp Val Leu  Lys Ala Thr
    1235                 1240                 1245

His Ala  Asn Tyr Lys Val Thr  Leu Asp Leu Gln Asn  Ser Thr Glu
    1250                 1255                 1260

Lys Phe  Gly Gly Phe Leu Arg  Ser Ala Leu Asp Val  Leu Ser Gln
    1265                 1270                 1275

Ile Leu  Glu Leu Ala Thr Leu  Gln Asp Ile Gly Lys  Cys Val Glu
    1280                 1285                 1290

Glu Ile  Leu Gly Tyr Leu Lys  Ser Cys Phe Ser Arg  Glu Pro Met
    1295                 1300                 1305

Met Ala  Thr Val Cys Val Gln  Gln Leu Leu Lys Thr  Leu Phe Gly
    1310                 1315                 1320

Thr Asn  Leu Ala Ser Gln Phe  Asp Gly Leu Ser Ser  Asn Pro Ser
    1325                 1330                 1335

Lys Ser  Gln Gly Arg Ala Gln  Arg Leu Gly Ser Ser  Ser Val Arg
    1340                 1345                 1350

Pro Gly  Leu Tyr His Tyr Cys  Phe Met Ala Pro Tyr  Thr His Phe
    1355                 1360                 1365

Thr Gln  Ala Leu Ala Asp Ala  Ser Leu Arg Asn Met  Val Gln Ala
    1370                 1375                 1380

Glu Gln  Glu Asn Asp Thr Ser  Gly Trp Phe Asp Val  Leu Gln Lys
    1385                 1390                 1395

Val Ser  Thr Gln Leu Lys Thr  Asn Leu Thr Ser Val  Thr Lys Asn
    1400                 1405                 1410

Arg Ala  Asp Lys Asn Ala Ile  His Asn His Ile Arg  Leu Phe Glu
    1415                 1420                 1425

Pro Leu  Val Ile Lys Ala Leu  Lys Gln Tyr Thr Thr  Thr Thr Cys
    1430                 1435                 1440

Val Gln  Leu Gln Lys Gln Val  Leu Asp Leu Leu Ala  Gln Leu Val
    1445                 1450                 1455

Gln Leu  Arg Val Asn Tyr Cys  Leu Leu Asp Ser Asp  Gln Val Phe
    1460                 1465                 1470

Ile Gly  Phe Val Leu Lys Gln  Phe Glu Tyr Ile Glu  Val Gly Gln
    1475                 1480                 1485

Phe Arg  Glu Ser Glu Ala Ile  Ile Pro Asn Ile Phe  Phe Phe Leu
    1490                 1495                 1500

Val Leu  Leu Ser Tyr Glu Arg  Tyr His Ser Lys Gln  Ile Ile Gly
    1505                 1510                 1515

Ile Pro  Lys Ile Ile Gln Leu  Cys Asp Gly Ile Met  Ala Ser Gly
    1520                 1525                 1530

Arg Lys  Ala Val Thr His Ala  Ile Pro Ala Leu Gln  Pro Ile Val
    1535                 1540                 1545

His Asp  Leu Phe Val Leu Arg  Gly Thr Asn Lys Ala  Asp Ala Gly
    1550                 1555                 1560

Lys Glu  Leu Glu Thr Gln Lys  Glu Val Val Val Ser  Met Leu Leu
    1565                 1570                 1575

Arg Leu  Ile Gln Tyr His Gln  Val Leu Glu Met Phe  Ile Leu Val
    1580                 1585                 1590

Leu Gln  Gln Cys His Lys Glu  Asn Glu Asp Lys Trp  Lys Arg Leu
    1595                 1600                 1605

Ser Arg  Gln Ile Ala Asp Ile  Ile Leu Pro Met Leu  Ala Lys Gln
    1610                 1615                 1620
```

Gln Met His Ile Asp Ser His Glu Ala Leu Gly Val Leu Asn Thr
1625 1630 1635

Leu Phe Glu Ile Leu Ala Pro Ser Ser Leu Arg Pro Val Asp Met
1640 1645 1650

Leu Leu Arg Ser Met Phe Val Thr Pro Asn Thr Met Ala Ser Val
1655 1660 1665

Ser Thr Val Gln Leu Trp Ile Ser Gly Ile Leu Ala Ile Leu Arg
1670 1675 1680

Val Leu Ile Ser Gln Ser Thr Glu Asp Ile Val Leu Ser Arg Ile
1685 1690 1695

Gln Glu Leu Ser Phe Ser Pro Tyr Leu Ile Ser Cys Thr Val Ile
1700 1705 1710

Asn Arg Leu Arg Asp Gly Asp Ser Thr Ser Thr Leu Glu Glu His
1715 1720 1725

Ser Glu Gly Lys Gln Ile Lys Asn Leu Pro Glu Glu Thr Phe Ser
1730 1735 1740

Arg Phe Leu Leu Gln Leu Val Gly Ile Leu Leu Glu Asp Ile Val
1745 1750 1755

Thr Lys Gln Leu Lys Val Glu Met Ser Glu Gln Gln His Thr Phe
1760 1765 1770

Tyr Cys Gln Glu Leu Gly Thr Leu Leu Met Cys Leu Ile His Ile
1775 1780 1785

Phe Lys Ser Gly Met Phe Arg Arg Ile Thr Ala Ala Ala Thr Arg
1790 1795 1800

Leu Phe Arg Ser Asp Gly Cys Gly Gly Ser Phe Tyr Thr Leu Asp
1805 1810 1815

Ser Leu Asn Leu Arg Ala Arg Ser Met Ile Thr Thr His Pro Ala
1820 1825 1830

Leu Val Leu Leu Trp Cys Gln Ile Leu Leu Leu Val Asn His Thr
1835 1840 1845

Asp Tyr Arg Trp Trp Ala Glu Val Gln Gln Thr Pro Lys Arg His
1850 1855 1860

Ser Leu Ser Ser Thr Lys Leu Leu Ser Pro Gln Met Ser Gly Glu
1865 1870 1875

Glu Glu Asp Ser Asp Leu Ala Ala Lys Leu Gly Met Cys Asn Arg
1880 1885 1890

Glu Ile Val Arg Arg Gly Ala Leu Ile Leu Phe Cys Asp Tyr Val
1895 1900 1905

Cys Gln Asn Leu His Asp Ser Glu His Leu Thr Trp Leu Ile Val
1910 1915 1920

Asn His Ile Gln Asp Leu Ile Ser Leu Ser His Glu Pro Pro Val
1925 1930 1935

Gln Asp Phe Ile Ser Ala Val His Arg Asn Ser Ala Ala Ser Gly
1940 1945 1950

Leu Phe Ile Gln Ala Ile Gln Ser Arg Cys Glu Asn Leu Ser Thr
1955 1960 1965

Pro Thr Met Leu Lys Lys Thr Leu Gln Cys Leu Glu Gly Ile His
1970 1975 1980

Leu Ser Gln Ser Gly Ala Val Leu Thr Leu Tyr Val Asp Arg Leu
1985 1990 1995

Leu Cys Thr Pro Phe Arg Val Leu Ala Arg Met Val Asp Ile Leu
2000 2005 2010

Ala Cys Arg Arg Val Glu Met Leu Leu Ala Ala Asn Leu Gln Ser

```
    2015                2020                2025

Ser Met  Ala Gln Leu Pro Met  Glu Glu Leu Asn Arg  Ile Gln Glu
    2030                2035                2040

Tyr Leu  Gln Ser Ser Gly Leu  Ala Gln Arg His Gln  Arg Leu Tyr
    2045                2050                2055

Ser Leu  Leu Asp Arg Phe Arg  Leu Ser Thr Met Gln  Asp Ser Leu
    2060                2065                2070

Ser Pro  Ser Pro Pro Val Ser  Ser His Pro Leu Asp  Gly Asp Gly
    2075                2080                2085

His Val  Ser Leu Glu Thr Val  Ser Pro Asp Lys Asp  Trp Tyr Val
    2090                2095                2100

His Leu  Val Lys Ser Gln Cys  Trp Thr Arg Ser Asp  Ser Ala Leu
    2105                2110                2115

Leu Glu  Gly Ala Glu Leu Val  Asn Arg Ile Pro Ala  Glu Asp Met
    2120                2125                2130

Asn Ala  Phe Met Met Asn Ser  Glu Phe Asn Leu Ser  Leu Leu Ala
    2135                2140                2145

Pro Cys  Leu Ser Leu Gly Met  Ser Glu Ile Ser Gly  Gly Gln Lys
    2150                2155                2160

Ser Ala  Leu Phe Glu Ala Ala  Arg Glu Val Thr Leu  Ala Arg Val
    2165                2170                2175

Ser Gly  Thr Val Gln Gln Leu  Pro Ala Val His His  Val Phe Gln
    2180                2185                2190

Pro Glu  Leu Pro Ala Glu Pro  Ala Ala Tyr Trp Ser  Lys Leu Asn
    2195                2200                2205

Asp Leu  Phe Gly Asp Ala Ala  Leu Tyr Gln Ser Leu  Pro Thr Leu
    2210                2215                2220

Ala Arg  Ala Leu Ala Gln Tyr  Leu Val Val Val Ser  Lys Leu Pro
    2225                2230                2235

Ser His  Leu His Leu Pro Pro  Glu Lys Glu Lys Asp  Ile Val Lys
    2240                2245                2250

Phe Val  Val Ala Thr Leu Glu  Ala Leu Ser Trp His  Leu Ile His
    2255                2260                2265

Glu Gln  Ile Pro Leu Ser Leu  Asp Leu Gln Ala Gly  Leu Asp Cys
    2270                2275                2280

Cys Cys  Leu Ala Leu Gln Leu  Pro Gly Leu Trp Ser  Val Val Ser
    2285                2290                2295

Ser Thr  Glu Phe Val Thr His  Ala Cys Ser Leu Ile  Tyr Cys Val
    2300                2305                2310

His Phe  Ile Leu Glu Ala Val  Ala Val Gln Pro Gly  Glu Gln Leu
    2315                2320                2325

Leu Ser  Pro Glu Arg Arg Thr  Asn Thr Pro Lys Ala  Ile Ser Glu
    2330                2335                2340

Glu Glu  Glu Glu Val Asp Pro  Asn Thr Gln Asn Pro  Lys Tyr Ile
    2345                2350                2355

Thr Ala  Ala Cys Glu Met Val  Ala Glu Met Val Glu  Ser Leu Gln
    2360                2365                2370

Ser Val  Leu Ala Leu Gly His  Lys Arg Asn Ser Gly  Val Pro Ala
    2375                2380                2385

Phe Leu  Thr Pro Leu Leu Arg  Asn Ile Ile Ile Ser  Leu Ala Arg
    2390                2395                2400

Leu Pro  Leu Val Asn Ser Tyr  Thr Arg Val Pro Pro  Leu Val Trp
    2405                2410                2415
```

```
Lys Leu Gly Trp Ser Pro Lys Pro Gly Gly Asp Phe Gly Thr Ala
    2420                2425                2430

Phe Pro Glu Ile Pro Val Glu Phe Leu Gln Glu Lys Glu Val Phe
    2435                2440                2445

Lys Glu Phe Ile Tyr Arg Ile Asn Thr Leu Gly Trp Thr Ser Arg
    2450                2455                2460

Thr Gln Phe Glu Glu Thr Trp Ala Thr Leu Leu Gly Val Leu Val
    2465                2470                2475

Thr Gln Pro Leu Val Met Glu Gln Glu Glu Ser Pro Pro Glu Glu
    2480                2485                2490

Asp Thr Glu Arg Thr Gln Ile Asn Val Leu Ala Val Gln Ala Ile
    2495                2500                2505

Thr Ser Leu Val Leu Ser Ala Met Thr Val Pro Val Ala Gly Asn
    2510                2515                2520

Pro Ala Val Ser Cys Leu Glu Gln Gln Pro Arg Asn Lys Pro Leu
    2525                2530                2535

Lys Ala Leu Asp Thr Arg Phe Gly Arg Lys Leu Ser Ile Ile Arg
    2540                2545                2550

Gly Ile Val Glu Gln Glu Ile Gln Ala Met Val Ser Lys Arg Glu
    2555                2560                2565

Asn Ile Ala Thr His His Leu Tyr Gln Ala Trp Asp Pro Val Pro
    2570                2575                2580

Ser Leu Ser Pro Ala Thr Thr Gly Ala Leu Ile Ser His Glu Lys
    2585                2590                2595

Leu Leu Leu Gln Ile Asn Pro Glu Arg Glu Leu Gly Ser Met Ser
    2600                2605                2610

Tyr Lys Leu Gly Gln Val Ser Ile His Ser Val Trp Leu Gly Asn
    2615                2620                2625

Ser Ile Thr Pro Leu Arg Glu Glu Glu Trp Asp Glu Glu Glu Glu
    2630                2635                2640

Glu Glu Ala Asp Ala Pro Ala Pro Ser Ser Pro Pro Thr Ser Pro
    2645                2650                2655

Val Asn Ser Arg Lys His Arg Ala Gly Val Asp Ile His Ser Cys
    2660                2665                2670

Ser Gln Phe Leu Leu Glu Leu Tyr Ser Arg Trp Ile Leu Pro Ser
    2675                2680                2685

Ser Ser Ala Arg Arg Thr Pro Ala Ile Leu Ile Ser Glu Val Val
    2690                2695                2700

Arg Ser Leu Leu Val Val Ser Asp Leu Phe Thr Glu Arg Asn Gln
    2705                2710                2715

Phe Glu Leu Met Tyr Val Thr Leu Thr Glu Leu Arg Arg Val His
    2720                2725                2730

Pro Ser Glu Asp Glu Ile Leu Ala Gln Tyr Leu Val Pro Ala Thr
    2735                2740                2745

Cys Lys Ala Ala Ala Val Leu Gly Met Asp Lys Ala Val Ala Glu
    2750                2755                2760

Pro Val Ser Arg Leu Leu Glu Ser Thr Leu Arg Ser Ser His Leu
    2765                2770                2775

Pro Ser Arg Val Gly Ala Leu His Gly Val Leu Tyr Val Leu Glu
    2780                2785                2790

Cys Asp Leu Leu Asp Asp Thr Ala Lys Gln Leu Ile Pro Val Ile
    2795                2800                2805
```

```
Ser Asp  Tyr Leu Leu Ser Asn  Leu Lys Gly Ile Ala  His Cys Val
    2810                2815                2820

Asn Ile  His Ser Gln Gln His  Val Leu Val Met Cys  Ala Thr Ala
    2825                2830                2835

Phe Tyr  Leu Ile Glu Asn Tyr  Pro Leu Asp Val Gly  Pro Glu Phe
    2840                2845                2850

Ser Ala  Ser Ile Ile Gln Met  Cys Gly Val Met Leu  Ser Gly Ser
    2855                2860                2865

Glu Glu  Ser Thr Pro Ser Ile  Ile Tyr His Cys Ala  Leu Arg Gly
    2870                2875                2880

Leu Glu  Arg Leu Leu Leu Ser  Glu Gln Leu Ser Arg  Leu Asp Ala
    2885                2890                2895

Glu Ser  Leu Val Lys Leu Ser  Val Asp Arg Val Asn  Val His Ser
    2900                2905                2910

Pro His  Arg Ala Met Ala Ala  Leu Gly Leu Met Leu  Thr Cys Met
    2915                2920                2925

Tyr Thr  Gly Lys Glu Lys Val  Ser Pro Gly Arg Thr  Ser Asp Pro
    2930                2935                2940

Asn Pro  Ala Ala Pro Asp Ser  Glu Ser Val Ile Val  Ala Met Glu
    2945                2950                2955

Arg Val  Ser Val Leu Phe Asp  Arg Ile Arg Lys Gly  Phe Pro Cys
    2960                2965                2970

Glu Ala  Arg Val Val Ala Arg  Ile Leu Pro Gln Phe  Leu Asp Asp
    2975                2980                2985

Phe Phe  Pro Pro Gln Asp Ile  Met Asn Lys Val Ile  Gly Glu Phe
    2990                2995                3000

Leu Ser  Asn Gln Gln Pro Tyr  Pro Gln Phe Met Ala  Thr Val Val
    3005                3010                3015

Tyr Lys  Val Phe Gln Thr Leu  His Ser Thr Gly Gln  Ser Ser Met
    3020                3025                3030

Val Arg  Asp Trp Val Met Leu  Ser Leu Ser Asn Phe  Thr Gln Arg
    3035                3040                3045

Ala Pro  Val Ala Met Ala Thr  Trp Ser Leu Ser Cys  Phe Phe Val
    3050                3055                3060

Ser Ala  Ser Thr Ser Pro Trp  Val Ala Ala Ile Leu  Pro His Val
    3065                3070                3075

Ile Ser  Arg Met Gly Lys Leu  Glu Gln Val Asp Val  Asn Leu Phe
    3080                3085                3090

Cys Leu  Val Ala Thr Asp Phe  Tyr Arg His Gln Ile  Glu Glu Glu
    3095                3100                3105

Leu Asp  Arg Arg Ala Phe Gln  Ser Val Leu Glu Val  Val Ala Ala
    3110                3115                3120

Pro Gly  Ser Pro Tyr His Arg  Leu Leu Thr Cys Leu  Arg Asn Val
    3125                3130                3135

His Lys  Val Thr Thr Cys
    3140
```

<210> SEQ ID NO 13
<211> LENGTH: 11
<212> TYPE: PRT
<213> ORGANISM: Homo sapiens
<220> FEATURE:
<221> NAME/KEY: Misc_feature
<222> LOCATION: (7)..(7)
<223> OTHER INFORMATION: Lys is acetylated

<400> SEQUENCE: 13

Cys Arg Lys Gln Lys Gly Lys Val Leu Leu Gly
1 5 10

<210> SEQ ID NO 14
<211> LENGTH: 7
<212> TYPE: PRT
<213> ORGANISM: Homo sapiens

<400> SEQUENCE: 14

Gln Lys Gly Lys Val Leu Leu
1 5

<210> SEQ ID NO 15
<211> LENGTH: 8
<212> TYPE: PRT
<213> ORGANISM: Homo sapiens

<400> SEQUENCE: 15

Lys Gln Lys Gly Lys Val Leu Leu
1 5

<210> SEQ ID NO 16
<211> LENGTH: 11
<212> TYPE: PRT
<213> ORGANISM: Homo sapiens

<400> SEQUENCE: 16

Ser Arg Lys Gln Lys Gly Lys Val Leu Leu Gly
1 5 10

<210> SEQ ID NO 17
<211> LENGTH: 13
<212> TYPE: PRT
<213> ORGANISM: Homo sapiens

<400> SEQUENCE: 17

Lys Gly Lys Val Leu Leu Gly Glu Glu Glu Ala Leu Glu
1 5 10

<210> SEQ ID NO 18
<211> LENGTH: 15
<212> TYPE: PRT
<213> ORGANISM: Homo sapiens

<400> SEQUENCE: 18

Gln Lys Gly Lys Val Leu Leu Gly Glu Glu Glu Ala Leu Glu Asp
1 5 10 15

<210> SEQ ID NO 19
<211> LENGTH: 10
<212> TYPE: PRT
<213> ORGANISM: Homo sapiens

<400> SEQUENCE: 19

Gly Lys Val Leu Leu Gly Glu Glu Glu Ala
1 5 10

<210> SEQ ID NO 20
<211> LENGTH: 14
<212> TYPE: PRT
<213> ORGANISM: Homo sapiens

<400> SEQUENCE: 20

```
Gln Lys Gly Lys Val Leu Leu Gly Glu Glu Glu Ala Leu Glu
1               5                   10


<210> SEQ ID NO 21
<211> LENGTH: 50
<212> TYPE: PRT
<213> ORGANISM: Homo sapiens

<400> SEQUENCE: 21

Ser Ile Val Glu Leu Ile Ala Gly Gly Gly Ser Ser Cys Ser Pro Val
1               5                   10                  15

Leu Ser Arg Lys Gln Lys Gly Lys Val Leu Leu Gly Glu Glu Glu Ala
            20                  25                  30

Leu Glu Asp Asp Ser Glu Ser Arg Ser Asp Val Ser Ser Ser Ala Leu
        35                  40                  45

Thr Ala
    50


<210> SEQ ID NO 22
<211> LENGTH: 48
<212> TYPE: PRT
<213> ORGANISM: Homo sapiens

<400> SEQUENCE: 22

Ile Val Glu Leu Ile Ala Gly Gly Gly Ser Ser Cys Ser Pro Val Leu
1               5                   10                  15

Ser Arg Lys Gln Lys Gly Lys Val Leu Leu Gly Glu Glu Glu Ala Leu
            20                  25                  30

Glu Asp Asp Ser Glu Ser Arg Ser Asp Val Ser Ser Ser Ala Leu Thr
        35                  40                  45


<210> SEQ ID NO 23
<211> LENGTH: 48
<212> TYPE: PRT
<213> ORGANISM: Homo sapiens

<400> SEQUENCE: 23

Val Glu Leu Ile Ala Gly Gly Gly Ser Ser Cys Ser Pro Val Leu Ser
1               5                   10                  15

Arg Lys Gln Lys Gly Lys Val Leu Leu Gly Glu Glu Glu Ala Leu Glu
            20                  25                  30

Asp Asp Ser Glu Ser Arg Ser Asp Val Ser Ser Ser Ala Leu Thr Ala
        35                  40                  45


<210> SEQ ID NO 24
<211> LENGTH: 42
<212> TYPE: PRT
<213> ORGANISM: Homo sapiens

<400> SEQUENCE: 24

Gly Gly Ser Ser Cys Ser Pro Val Leu Ser Arg Lys Gln Lys Gly Lys
1               5                   10                  15

Val Leu Leu Gly Glu Glu Glu Ala Leu Glu Asp Asp Ser Glu Ser Arg
            20                  25                  30

Ser Asp Val Ser Ser Ser Ala Leu Thr Ala
        35                  40


<210> SEQ ID NO 25
<211> LENGTH: 38
<212> TYPE: PRT
<213> ORGANISM: Homo sapiens
```

<400> SEQUENCE: 25

```
Cys Ser Pro Val Leu Ser Arg Lys Gln Lys Gly Lys Val Leu Leu Gly
1               5                   10                  15

Glu Glu Glu Ala Leu Glu Asp Asp Ser Glu Ser Arg Ser Asp Val Ser
            20                  25                  30

Ser Ser Ala Leu Thr Ala
        35
```

<210> SEQ ID NO 26
<211> LENGTH: 37
<212> TYPE: PRT
<213> ORGANISM: Homo sapiens

<400> SEQUENCE: 26

```
Ser Ile Val Glu Leu Ile Ala Gly Gly Gly Ser Ser Cys Ser Pro Val
1               5                   10                  15

Leu Ser Arg Lys Gln Lys Gly Lys Val Leu Leu Gly Glu Glu Glu Ala
            20                  25                  30

Leu Glu Asp Asp Ser
        35
```

<210> SEQ ID NO 27
<211> LENGTH: 40
<212> TYPE: PRT
<213> ORGANISM: Homo sapiens

<400> SEQUENCE: 27

```
Ser Ile Val Glu Leu Ile Ala Gly Gly Gly Ser Ser Cys Ser Pro Val
1               5                   10                  15

Leu Ser Arg Lys Gln Lys Gly Lys Val Leu Leu Gly Glu Glu Glu Ala
            20                  25                  30

Leu Glu Asp Asp Ser Glu Ser Arg
        35                  40
```

<210> SEQ ID NO 28
<211> LENGTH: 45
<212> TYPE: PRT
<213> ORGANISM: Homo sapiens

<400> SEQUENCE: 28

```
Ser Ile Val Glu Leu Ile Ala Gly Gly Gly Ser Ser Cys Ser Pro Val
1               5                   10                  15

Leu Ser Arg Lys Gln Lys Gly Lys Val Leu Leu Gly Glu Glu Glu Ala
            20                  25                  30

Leu Glu Asp Asp Ser Glu Ser Arg Ser Asp Val Ser Ser
        35                  40                  45
```

<210> SEQ ID NO 29
<211> LENGTH: 46
<212> TYPE: PRT
<213> ORGANISM: Homo sapiens

<400> SEQUENCE: 29

```
Ser Ile Val Glu Leu Ile Ala Gly Gly Gly Ser Ser Cys Ser Pro Val
1               5                   10                  15

Leu Ser Arg Lys Gln Lys Gly Lys Val Leu Leu Gly Glu Glu Glu Ala
            20                  25                  30

Leu Glu Asp Asp Ser Glu Ser Arg Ser Asp Val Ser Ser Ser
        35                  40                  45
```

<210> SEQ ID NO 30
<211> LENGTH: 38
<212> TYPE: PRT
<213> ORGANISM: Homo sapiens

<400> SEQUENCE: 30

```
Glu Leu Ile Ala Gly Gly Gly Ser Ser Cys Ser Pro Val Leu Ser Arg
1               5                   10                  15

Lys Gln Lys Gly Lys Val Leu Leu Gly Glu Glu Glu Ala Leu Glu Asp
            20                  25                  30

Asp Ser Glu Ser Arg Ser
        35
```

<210> SEQ ID NO 31
<211> LENGTH: 34
<212> TYPE: PRT
<213> ORGANISM: Homo sapiens

<400> SEQUENCE: 31

```
Ser Cys Ser Pro Val Leu Ser Arg Lys Gln Lys Gly Lys Val Leu Leu
1               5                   10                  15

Gly Glu Glu Glu Ala Leu Glu Asp Asp Ser Glu Ser Arg Ser Asp Val
            20                  25                  30

Ser Ser
```

<210> SEQ ID NO 32
<211> LENGTH: 45
<212> TYPE: PRT
<213> ORGANISM: Homo sapiens

<400> SEQUENCE: 32

```
Ser Ile Val Glu Leu Ile Ala Gly Gly Gly Ser Ser Cys Ser Pro Val
1               5                   10                  15

Leu Ser Arg Lys Gln Lys Gly Lys Val Leu Leu Gly Glu Glu Glu Ala
            20                  25                  30

Leu Glu Asp Asp Ser Glu Ser Arg Ser Asp Val Ser Ser
        35                  40                  45
```

<210> SEQ ID NO 33
<211> LENGTH: 15
<212> TYPE: PRT
<213> ORGANISM: Homo sapiens

<400> SEQUENCE: 33

```
Val Leu Ser Arg Lys Gln Lys Gly Lys Val Leu Leu Gly Glu Glu
1               5                   10                  15
```

<210> SEQ ID NO 34
<211> LENGTH: 38
<212> TYPE: PRT
<213> ORGANISM: Homo sapiens

<400> SEQUENCE: 34

```
Cys Ser Pro Val Leu Ser Arg Lys Gln Lys Gly Lys Val Leu Leu Gly
1               5                   10                  15

Glu Glu Glu Ala Leu Glu Asp Asp Ser Glu Ser Arg Ser Asp Val Ser
            20                  25                  30

Ser Ser Ala Leu Thr Ala
        35
```

<210> SEQ ID NO 35
<211> LENGTH: 24
<212> TYPE: PRT
<213> ORGANISM: Homo sapiens

<400> SEQUENCE: 35

```
Gly Gly Ser Ser Cys Ser Pro Val Leu Ser Arg Lys Gln Lys Gly Lys
1               5                   10                  15

Val Leu Leu Gly Glu Glu Glu Ala
            20
```

<210> SEQ ID NO 36
<211> LENGTH: 15
<212> TYPE: PRT
<213> ORGANISM: Homo sapiens

<400> SEQUENCE: 36

```
Gly Ser Ser Cys Ser Pro Val Leu Ser Arg Lys Gln Lys Gly Lys
1               5                   10                  15
```

<210> SEQ ID NO 37
<211> LENGTH: 15
<212> TYPE: PRT
<213> ORGANISM: Homo sapiens

<400> SEQUENCE: 37

```
Lys Gly Lys Val Leu Leu Gly Glu Glu Glu Ala Leu Glu Asp Asp
1               5                   10                  15
```

<210> SEQ ID NO 38
<211> LENGTH: 40
<212> TYPE: PRT
<213> ORGANISM: Homo sapiens

<400> SEQUENCE: 38

```
Ser Ser Cys Ser Pro Val Leu Ser Arg Lys Gln Lys Gly Lys Val Leu
1               5                   10                  15

Leu Gly Glu Glu Glu Ala Leu Glu Asp Asp Ser Glu Ser Arg Ser Asp
            20                  25                  30

Val Ser Ser Ser Ala Leu Thr Ala
        35                  40
```

<210> SEQ ID NO 39
<211> LENGTH: 30
<212> TYPE: PRT
<213> ORGANISM: Homo sapiens

<400> SEQUENCE: 39

```
Ser Ser Cys Ser Pro Val Leu Ser Arg Lys Gln Lys Gly Lys Val Leu
1               5                   10                  15

Leu Gly Glu Glu Glu Ala Leu Glu Asp Asp Ser Glu Ser Arg
            20                  25                  30
```

<210> SEQ ID NO 40
<211> LENGTH: 27
<212> TYPE: PRT
<213> ORGANISM: Homo sapiens

<400> SEQUENCE: 40

```
Leu Ile Ala Gly Gly Gly Ser Ser Cys Ser Pro Val Leu Ser Arg Lys
1               5                   10                  15

Gln Lys Gly Lys Val Leu Leu Gly Glu Glu Glu
```

```
            20                  25


<210> SEQ ID NO 41
<211> LENGTH: 35
<212> TYPE: PRT
<213> ORGANISM: Homo sapiens

<400> SEQUENCE: 41

Val Leu Ser Arg Lys Gln Lys Gly Lys Val Leu Leu Gly Glu Glu Glu
1               5                   10                  15

Ala Leu Glu Asp Asp Ser Glu Ser Arg Ser Asp Val Ser Ser Ser Ala
            20                  25                  30

Leu Thr Ala
        35


<210> SEQ ID NO 42
<211> LENGTH: 29
<212> TYPE: PRT
<213> ORGANISM: Homo sapiens

<400> SEQUENCE: 42

Ser Ser Cys Ser Pro Val Leu Ser Arg Lys Gln Lys Gly Lys Val Leu
1               5                   10                  15

Leu Gly Glu Glu Glu Ala Leu Glu Asp Asp Ser Glu Ser
            20                  25


<210> SEQ ID NO 43
<211> LENGTH: 24
<212> TYPE: PRT
<213> ORGANISM: Homo sapiens

<400> SEQUENCE: 43

Cys Ser Pro Val Leu Ser Arg Lys Gln Lys Gly Lys Val Leu Leu Gly
1               5                   10                  15

Glu Glu Glu Ala Leu Glu Asp Asp
            20


<210> SEQ ID NO 44
<211> LENGTH: 19
<212> TYPE: PRT
<213> ORGANISM: Homo sapiens

<400> SEQUENCE: 44

Ser Ser Cys Ser Pro Val Leu Ser Arg Lys Gln Lys Gly Lys Val Leu
1               5                   10                  15

Leu Gly Glu


<210> SEQ ID NO 45
<211> LENGTH: 17
<212> TYPE: PRT
<213> ORGANISM: Homo sapiens

<400> SEQUENCE: 45

Lys Gln Lys Gly Lys Val Leu Leu Gly Glu Glu Glu Ala Leu Glu Asp
1               5                   10                  15

Asp


<210> SEQ ID NO 46
<211> LENGTH: 18
<212> TYPE: PRT
<213> ORGANISM: Homo sapiens
```

<400> SEQUENCE: 46

Ser Cys Ser Pro Val Leu Ser Arg Lys Gln Lys Gly Lys Val Leu Leu
1               5                   10                  15

Gly Glu

<210> SEQ ID NO 47
<211> LENGTH: 46
<212> TYPE: PRT
<213> ORGANISM: Homo sapiens

<400> SEQUENCE: 47

Val Glu Leu Ile Ala Gly Gly Gly Ser Ser Cys Ser Pro Val Leu Ser
1               5                   10                  15

Arg Lys Gln Lys Gly Lys Val Leu Leu Gly Glu Glu Glu Ala Leu Glu
            20                  25                  30

Asp Asp Ser Glu Ser Arg Ser Asp Val Ser Ser Ser Ala Leu
        35                  40                  45

<210> SEQ ID NO 48
<211> LENGTH: 5
<212> TYPE: PRT
<213> ORGANISM: Homo sapiens
<220> FEATURE:
<221> NAME/KEY: Misc_feature
<222> LOCATION: (3)..(3)
<223> OTHER INFORMATION: Lys is acetylated

<400> SEQUENCE: 48

Lys Gly Lys Val Leu
1               5

<210> SEQ ID NO 49
<211> LENGTH: 5
<212> TYPE: PRT
<213> ORGANISM: Homo sapiens
<220> FEATURE:
<221> NAME/KEY: Misc_feature
<222> LOCATION: (5)..(5)
<223> OTHER INFORMATION: Lys is acetylated

<400> SEQUENCE: 49

Lys Gln Lys Gly Lys
1               5

<210> SEQ ID NO 50
<211> LENGTH: 5
<212> TYPE: PRT
<213> ORGANISM: Homo sapiens
<220> FEATURE:
<221> NAME/KEY: Misc_feature
<222> LOCATION: (4)..(4)
<223> OTHER INFORMATION: Lys is acetylated

<400> SEQUENCE: 50

Gln Lys Gly Lys Val
1               5

<210> SEQ ID NO 51
<211> LENGTH: 5
<212> TYPE: PRT
<213> ORGANISM: Homo sapiens
<220> FEATURE:
<221> NAME/KEY: Misc_feature
<222> LOCATION: (2)..(2)
<223> OTHER INFORMATION: Lys  is acetylated -continued

```
<400> SEQUENCE: 51

Gly Lys Val Leu Leu
1               5


<210> SEQ ID NO 52
<211> LENGTH: 5
<212> TYPE: PRT
<213> ORGANISM: Homo sapiens
<220> FEATURE:
<221> NAME/KEY: Misc_feature
<222> LOCATION: (1)..(1)
<223> OTHER INFORMATION: Lys is acetylated

<400> SEQUENCE: 52

Lys Val Leu Leu Gly
1               5


<210> SEQ ID NO 53
<211> LENGTH: 11
<212> TYPE: PRT
<213> ORGANISM: Homo sapiens

<400> SEQUENCE: 53

Cys Arg Lys Gln Lys Gly Lys Val Leu Leu Gly
1               5                   10


<210> SEQ ID NO 54
<211> LENGTH: 11
<212> TYPE: PRT
<213> ORGANISM: Homo sapiens

<400> SEQUENCE: 54

Lys Leu Leu Glu Ala Ala Ala Arg Ala Cys Ile
1               5                   10
```